(12) United States Patent
Toner et al.

(10) Patent No.: US 8,304,230 B2
(45) Date of Patent: Nov. 6, 2012

(54) MICROFLUIDIC DEVICE FOR CELL SEPARATION AND USES THEREOF

(75) Inventors: Mehmet Toner, Wellesley, MA (US); George Truskey, Durham, NC (US); Ravi Kapur, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 1174 days.

(21) Appl. No.: 11/726,230

(22) Filed: Mar. 21, 2007

(65) Prior Publication Data

US 2007/0172903 A1   Jul. 26, 2007

Related U.S. Application Data

(62) Division of application No. 10/529,453, filed as application No. PCT/US03/30965 on Sep. 29, 2003.

(60) Provisional application No. 60/414,065, filed on Sep. 27, 2002, provisional application No. 60/414,258, filed on Sep. 27, 2002, provisional application No. 60/414,102, filed on Sep. 27, 2002.

(51) Int. Cl.
*C12M 1/34* (2006.01)
*C12M 3/00* (2006.01)

(52) U.S. Cl. ............ 435/288.5; 435/283.1; 435/287.1; 435/287.2; 435/288.7; 436/518; 422/50; 422/414; 422/68.1

(58) Field of Classification Search ............ 435/283.1, 435/287.1, 287.2, 288.7; 436/518; 422/50, 422/61, 68.1
See application file for complete search history.

(56) References Cited

U.S. PATENT DOCUMENTS

| | | | |
|---|---|---|---|
| 3,560,754 | A | 2/1971 | Kamentsky |
| 3,906,929 | A | 9/1975 | Augspurger |
| 3,924,947 | A | 12/1975 | Hogg |
| 4,009,435 | A | 2/1977 | Hogg |
| 4,055,799 | A | 10/1977 | Coster et al. |
| 4,115,534 | A | 9/1978 | Ithakissios |

(Continued)

FOREIGN PATENT DOCUMENTS

CA   2466896 A1   3/2003

(Continued)

OTHER PUBLICATIONS

"Micromechanics Imitate Blood Vessels" *Design News* 15 (Mar. 22, 1993).

(Continued)

*Primary Examiner* — Melanie J Yu
(74) *Attorney, Agent, or Firm* — Fish & Richardson P.C.

(57) ABSTRACT

The invention features methods for separating cells from a sample (e.g., separating fetal red blood cells from maternal blood). The method begins with the introduction of a sample including cells into one or more microfluidic channels. In one embodiment, the device includes at least two processing steps. For example, a mixture of cells is introduced into a microfluidic channel that selectively allows the passage of a desired type of cell, and the population of cells enriched in the desired type is then introduced into a second microfluidic channel that allows the passage of the desired cell to produce a population of cells further enriched in the desired type. The selection of cells is based on a property of the cells in the mixture, for example, size, shape, deformability, surface characteristics (e.g., cell surface receptors or antigens and membrane permeability), or intracellular properties (e.g., expression of a particular enzyme).

32 Claims, 25 Drawing Sheets

U.S. PATENT DOCUMENTS

| | | |
|---|---|---|
| 4,190,535 A | 2/1980 | Luderer et al. |
| 4,415,405 A | 11/1983 | Ruddle et al. |
| 4,434,156 A | 2/1984 | Trowbridge |
| 4,508,625 A | 4/1985 | Graham |
| 4,584,268 A | 4/1986 | Ceriani et al. |
| 4,664,796 A | 5/1987 | Graham et al. |
| 4,675,286 A | 6/1987 | Calenoff |
| 4,729,949 A | 3/1988 | Weinreb et al. |
| 4,789,628 A | 12/1988 | Nayak |
| 4,790,640 A | 12/1988 | Nason |
| 4,800,159 A | 1/1989 | Mullis et al. |
| 4,814,098 A | 3/1989 | Inada et al. |
| 4,886,761 A | 12/1989 | Gustafson et al. |
| 4,894,343 A | 1/1990 | Tanaka et al. |
| 4,895,805 A | 1/1990 | Sato et al. |
| 4,906,439 A | 3/1990 | Grenner |
| 4,925,788 A | 5/1990 | Liberti |
| 4,936,465 A | 6/1990 | Zoeld |
| 4,963,498 A | 10/1990 | Hillman et al. |
| 4,968,600 A | 11/1990 | Haraguchi et al. |
| 4,971,904 A | 11/1990 | Luddy |
| 4,977,078 A | 12/1990 | Niimura et al. |
| 4,984,574 A | 1/1991 | Goldberg et al. |
| 4,999,283 A | 3/1991 | Zavos |
| 5,039,426 A | 8/1991 | Giddings |
| 5,101,825 A | 4/1992 | Gravenstein et al. |
| 5,135,627 A | 8/1992 | Soane |
| 5,147,606 A | 9/1992 | Charlton et al. |
| 5,153,117 A | 10/1992 | Simons |
| 5,173,158 A | 12/1992 | Schmukler |
| 5,183,744 A | 2/1993 | Kamaura et al. |
| 5,186,827 A | 2/1993 | Liberti et al. |
| 5,215,926 A | 6/1993 | Etchells et al. |
| 5,240,856 A | 8/1993 | Goffe et al. |
| 5,275,933 A | 1/1994 | Teng et al. |
| 5,296,375 A | 3/1994 | Kricka et al. |
| 5,304,487 A | 4/1994 | Wilding et al. |
| 5,306,420 A | 4/1994 | Bisconte |
| 5,310,674 A | 5/1994 | Weinreb et al. |
| 5,328,843 A | 7/1994 | Fukuda et al. |
| 5,427,663 A | 6/1995 | Austin et al. |
| 5,427,946 A | 6/1995 | Kricka et al. |
| 5,432,054 A | 7/1995 | Saunders et al. |
| 5,437,987 A | 8/1995 | Tens et al. |
| 5,447,842 A | 9/1995 | Simons |
| 5,457,024 A | 10/1995 | Goldbard |
| 5,466,574 A | 11/1995 | Liberti et al. |
| 5,472,842 A | 12/1995 | Stokke et al. |
| 5,486,335 A | 1/1996 | Wilding et al. |
| 5,489,506 A | 2/1996 | Crane |
| 5,498,392 A | 3/1996 | Wilding et al. |
| 5,506,141 A | 4/1996 | Weinreb et al. |
| 5,529,903 A | 6/1996 | Kübler et al. |
| 5,541,072 A | 7/1996 | Wang et al. |
| 5,587,070 A | 12/1996 | Pall et al. |
| 5,622,831 A | 4/1997 | Liberti et al. |
| 5,629,147 A | 5/1997 | Asgari et al. |
| 5,635,358 A | 6/1997 | Wilding et al. |
| 5,637,458 A | 6/1997 | Frankel et al. |
| 5,637,469 A | 6/1997 | Wilding et al. |
| 5,639,669 A | 6/1997 | Ledley |
| 5,641,628 A | 6/1997 | Bianchi |
| 5,646,001 A | 7/1997 | Terstappen et al. |
| 5,648,220 A | 7/1997 | Bianchi et al. |
| 5,662,813 A | 9/1997 | Sammons et al. |
| 5,665,540 A | 9/1997 | Lebo |
| 5,672,481 A | 9/1997 | Minshall et al. |
| 5,676,849 A | 10/1997 | Sammons et al. |
| 5,707,799 A | 1/1998 | Hansmann et al. |
| 5,707,801 A | 1/1998 | Bresser et al. |
| 5,709,943 A | 1/1998 | Coleman et al. |
| 5,714,325 A | 2/1998 | Bianchi |
| 5,715,946 A | 2/1998 | Reichenbach |
| 5,716,776 A | 2/1998 | Bogart |
| 5,726,026 A | 3/1998 | Wilding et al. |
| 5,731,156 A | 3/1998 | Golbus |
| 5,750,015 A | 5/1998 | Soane et al. |
| 5,750,339 A | 5/1998 | Smith |
| 5,753,014 A | 5/1998 | Van Rijn |
| 5,766,843 A | 6/1998 | Asgari et al. |
| 5,770,029 A | 6/1998 | Nelson et al. |
| 5,830,679 A | 11/1998 | Bianchi |
| 5,837,115 A | 11/1998 | Austin et al. |
| 5,842,787 A | 12/1998 | Kopf-Sill et al. |
| 5,843,767 A | 12/1998 | Beattie |
| 5,846,708 A | 12/1998 | Hollis et al. |
| 5,856,174 A | 1/1999 | Lipshutz et al. |
| 5,858,187 A | 1/1999 | Ramsey et al. |
| 5,858,188 A | 1/1999 | Soane et al. |
| 5,858,195 A | 1/1999 | Ramsey |
| 5,858,649 A | 1/1999 | Asgari et al. |
| 5,861,253 A | 1/1999 | Asgari et al. |
| 5,863,502 A | 1/1999 | Southgate et al. |
| 5,866,345 A | 2/1999 | Wilding et al. |
| 5,869,004 A | 2/1999 | Parce et al. |
| 5,879,624 A | 3/1999 | Boehringer et al. |
| 5,882,465 A | 3/1999 | McReynolds |
| 5,891,651 A | 4/1999 | Roche et al. |
| 5,906,724 A | 5/1999 | Sammons et al. |
| 5,928,880 A | 7/1999 | Wilding et al. |
| 5,948,278 A | 9/1999 | Sammons et al. |
| 5,952,173 A | 9/1999 | Hansmann et al. |
| 5,957,579 A | 9/1999 | Kopf-Sill et al. |
| 5,962,234 A | 10/1999 | Golbus |
| 5,972,721 A | 10/1999 | Bruno et al. |
| 5,993,665 A | 11/1999 | Terstappen et al. |
| 5,994,517 A | 11/1999 | Ts'o et al. |
| 6,001,229 A | 12/1999 | Ramsey |
| 6,004,762 A | 12/1999 | Tse et al. |
| 6,007,690 A | 12/1999 | Nelson et al. |
| 6,008,007 A | 12/1999 | Fruehauf et al. |
| 6,008,010 A | 12/1999 | Greenberger et al. |
| 6,013,188 A | 1/2000 | Terstappen et al. |
| 6,027,623 A | 2/2000 | Ohkawa |
| 6,033,546 A | 3/2000 | Ramsey |
| 6,036,857 A | 3/2000 | Chen et al. |
| 6,043,027 A | 3/2000 | Selick et al. |
| 6,045,990 A | 4/2000 | Baust et al. |
| 6,048,498 A | 4/2000 | Kennedy |
| 6,054,034 A | 4/2000 | Soane et al. |
| 6,056,859 A | 5/2000 | Ramsey et al. |
| 6,062,261 A | 5/2000 | Jacobson et al. |
| 6,066,449 A | 5/2000 | Ditkoff et al. |
| 6,068,818 A | 5/2000 | Ackley et al. |
| 6,071,394 A | 6/2000 | Cheng et al. |
| 6,074,827 A | 6/2000 | Nelson et al. |
| 6,083,761 A | 7/2000 | Kedar et al. |
| 6,086,740 A | 7/2000 | Kennedy |
| 6,087,134 A | 7/2000 | Saunders |
| 6,100,029 A | 8/2000 | Lapidus et al. |
| 6,100,033 A | 8/2000 | Smith et al. |
| 6,110,343 A | 8/2000 | Ramsey et al. |
| 6,120,666 A | 9/2000 | Jacobson et al. |
| 6,120,856 A | 9/2000 | Liberti et al. |
| 6,129,848 A | 10/2000 | Chen et al. |
| 6,130,098 A | 10/2000 | Handique et al. |
| 6,143,247 A | 11/2000 | Sheppard, Jr. et al. |
| 6,143,576 A | 11/2000 | Buechler |
| 6,150,119 A | 11/2000 | Kopf-Sill et al. |
| 6,153,073 A | 11/2000 | Dubrow et al. |
| 6,156,270 A | 12/2000 | Buechler |
| 6,159,685 A | 12/2000 | Pinkel et al. |
| 6,165,270 A | 12/2000 | Konishi et al. |
| 6,169,816 B1 | 1/2001 | Ravkin |
| 6,174,683 B1 | 1/2001 | Hahn et al. |
| 6,176,962 B1 | 1/2001 | Soane et al. |
| 6,184,029 B1 | 2/2001 | Wilding et al. |
| 6,184,043 B1 | 2/2001 | Fodstad et al. |
| 6,186,660 B1 | 2/2001 | Kopf-Sill et al. |
| 6,197,523 B1 | 3/2001 | Rimm et al. |
| 6,200,765 B1 | 3/2001 | Murphy et al. |
| 6,210,574 B1 | 4/2001 | Sammons et al. |
| 6,210,889 B1 | 4/2001 | Drouin et al. |
| 6,210,910 B1 | 4/2001 | Walt et al. |
| 6,213,151 B1 | 4/2001 | Jacobson et al. |
| 6,214,558 B1 | 4/2001 | Shuber et al. |
| 6,235,474 B1 | 5/2001 | Feinberg |

| | | | |
|---|---|---|---|
| 6,241,894 B1 | 6/2001 | Briggs et al. | |
| 6,242,209 B1 | 6/2001 | Ransom et al. | |
| 6,245,227 B1 | 6/2001 | Moon et al. | |
| 6,251,343 B1 | 6/2001 | Dubrow et al. | |
| 6,251,691 B1 | 6/2001 | Seul | |
| 6,258,540 B1 | 7/2001 | Lo et al. | |
| 6,265,229 B1 | 7/2001 | Fodstad et al. | |
| 6,274,337 B1 | 8/2001 | Parce et al. | |
| 6,277,489 B1 | 8/2001 | Abbott et al. | |
| 6,277,569 B1 | 8/2001 | Bittner et al. | |
| 6,280,967 B1 | 8/2001 | Ransom et al. | |
| 6,287,857 B1 | 9/2001 | O'Riordan et al. | |
| 6,291,249 B1 | 9/2001 | Mahant et al. | |
| 6,294,392 B1 | 9/2001 | Kuhr et al. | |
| 6,296,752 B1 | 10/2001 | McBride et al. | |
| 6,306,578 B1 | 10/2001 | Schellenberger et al. | |
| 6,309,889 B1 | 10/2001 | Cutler et al. | |
| 6,315,940 B1 | 11/2001 | Nisch et al. | |
| 6,315,953 B1 | 11/2001 | Ackley et al. | |
| 6,319,468 B1 | 11/2001 | Sheppard, Jr. et al. | |
| 6,331,274 B1 | 12/2001 | Ackley et al. | |
| 6,344,326 B1 | 2/2002 | Nelson et al. | |
| 6,355,491 B1 | 3/2002 | Zhou et al. | |
| 6,361,958 B1 | 3/2002 | Shieh et al. | |
| 6,365,362 B1 | 4/2002 | Terstappen et al. | |
| 6,368,562 B1 | 4/2002 | Yao | |
| 6,368,871 B1 * | 4/2002 | Christel et al. | 436/180 |
| 6,372,432 B1 | 4/2002 | Tocque et al. | |
| 6,372,542 B1 | 4/2002 | Martin et al. | |
| 6,376,181 B2 | 4/2002 | Ramsey et al. | |
| 6,377,721 B1 | 4/2002 | Walt et al. | |
| 6,379,884 B2 | 4/2002 | Wada et al. | |
| 6,383,759 B1 | 5/2002 | Murphy et al. | |
| 6,387,290 B1 | 5/2002 | Brody et al. | |
| 6,387,707 B1 | 5/2002 | Seul et al. | |
| 6,394,942 B2 | 5/2002 | Moon et al. | |
| 6,395,232 B1 | 5/2002 | McBride | |
| 6,399,023 B1 | 6/2002 | Chow | |
| 6,432,630 B1 | 8/2002 | Blankenstein | |
| 6,432,720 B2 | 8/2002 | Chow | |
| 6,444,461 B1 | 9/2002 | Knapp et al. | |
| 6,453,928 B1 | 9/2002 | Kaplan et al. | |
| 6,454,938 B2 | 9/2002 | Moon et al. | |
| 6,454,945 B1 | 9/2002 | Weigl et al. | |
| 6,455,260 B1 | 9/2002 | Muller et al. | |
| 6,465,225 B1 | 10/2002 | Fuhr et al. | |
| 6,479,299 B1 | 11/2002 | Parce et al. | |
| 6,488,895 B1 | 12/2002 | Kennedy | |
| 6,495,340 B2 | 12/2002 | Huberman et al. | |
| 6,500,612 B1 | 12/2002 | Gray et al. | |
| 6,506,609 B1 * | 1/2003 | Wada et al. | 436/148 |
| 6,517,234 B1 | 2/2003 | Kopf-Sill et al. | |
| 6,521,188 B1 | 2/2003 | Webster | |
| 6,524,456 B1 | 2/2003 | Ramsey et al. | |
| 6,529,835 B1 | 3/2003 | Wada et al. | |
| 6,537,505 B1 | 3/2003 | LaBudde et al. | |
| 6,540,895 B1 | 4/2003 | Spence et al. | |
| 6,551,841 B1 | 4/2003 | Wilding et al. | |
| 6,569,324 B1 | 5/2003 | Moon et al. | |
| 6,569,626 B2 | 5/2003 | Bittner et al. | |
| 6,576,478 B1 | 6/2003 | Wagner et al. | |
| 6,582,904 B2 | 6/2003 | Dahm | |
| 6,582,969 B1 | 6/2003 | Wagner et al. | |
| 6,589,791 B1 | 7/2003 | LaBudde et al. | |
| 6,591,852 B1 * | 7/2003 | McNeely et al. | 137/14 |
| 6,596,144 B1 | 7/2003 | Regnier et al. | |
| 6,596,545 B1 | 7/2003 | Wagner et al. | |
| 6,605,453 B2 | 8/2003 | Ozkan et al. | |
| 6,605,454 B2 | 8/2003 | Barenburg et al. | |
| 6,613,525 B2 | 9/2003 | Nelson et al. | |
| 6,632,619 B1 | 10/2003 | Harrison et al. | |
| 6,632,652 B1 | 10/2003 | Austin et al. | |
| 6,632,655 B1 | 10/2003 | Mehta et al. | |
| 6,635,163 B1 | 10/2003 | Han et al. | |
| 6,637,463 B1 | 10/2003 | Lei et al. | |
| 6,645,731 B2 | 11/2003 | Terstappen et al. | |
| 6,664,104 B2 | 12/2003 | Pourahmadi et al. | |
| 6,673,541 B1 | 1/2004 | Klein et al. | |
| 6,674,525 B2 | 1/2004 | Bardell et al. | |
| 6,682,942 B1 | 1/2004 | Wagner et al. | |
| 6,685,841 B2 * | 2/2004 | Lopez et al. | 210/767 |
| 6,689,615 B1 | 2/2004 | Murto et al. | |
| 6,692,952 B1 | 2/2004 | Braff et al. | |
| 6,743,636 B2 | 6/2004 | Chung et al. | |
| 6,746,503 B1 | 6/2004 | Benett et al. | |
| 6,762,059 B2 | 7/2004 | Chan et al. | |
| 6,770,434 B2 | 8/2004 | Shvets et al. | |
| 6,783,647 B2 | 8/2004 | Culbertson et al. | |
| 6,783,928 B2 | 8/2004 | Hvichia et al. | |
| 6,790,330 B2 * | 9/2004 | Gascoyne et al. | 204/547 |
| 6,805,841 B2 | 10/2004 | Shvets et al. | |
| 6,815,664 B2 | 11/2004 | Wang et al. | |
| 6,818,184 B2 | 11/2004 | Fulwyler et al. | |
| 6,830,936 B2 | 12/2004 | Anderson et al. | |
| 6,849,423 B2 | 2/2005 | Mutz et al. | |
| 6,858,439 B1 | 2/2005 | Xu et al. | |
| 6,875,619 B2 | 4/2005 | Blackburn | |
| 6,878,271 B2 | 4/2005 | Gilbert et al. | |
| 6,881,315 B2 | 4/2005 | Iida et al. | |
| 6,893,836 B2 | 5/2005 | Mutz et al. | |
| 6,893,881 B1 | 5/2005 | Fodstad et al. | |
| 6,911,345 B2 | 6/2005 | Quake et al. | |
| 6,913,605 B2 | 7/2005 | Fletcher et al. | |
| 6,913,697 B2 | 7/2005 | Lopez et al. | |
| 6,942,771 B1 | 9/2005 | Kayyem | |
| 6,942,978 B1 | 9/2005 | O'Brien | |
| 6,949,355 B2 | 9/2005 | Yamanishi et al. | |
| 6,953,668 B1 | 10/2005 | Israeli et al. | |
| 6,958,245 B2 | 10/2005 | Seul et al. | |
| 6,960,449 B2 | 11/2005 | Wang et al. | |
| 6,974,667 B2 | 12/2005 | Horne et al. | |
| 6,991,917 B2 | 1/2006 | Mutz et al. | |
| 7,018,838 B2 | 3/2006 | Murphy et al. | |
| 7,150,812 B2 | 12/2006 | Huang et al. | |
| 7,160,687 B1 | 1/2007 | Kapur et al. | |
| 7,190,818 B2 | 3/2007 | Ellis et al. | |
| 7,195,872 B2 | 3/2007 | Agrawal et al. | |
| 7,276,170 B2 | 10/2007 | Oakey et al. | |
| 7,312,085 B2 * | 12/2007 | Chou et al. | 436/43 |
| 7,318,902 B2 | 1/2008 | Oakey et al. | |
| 7,431,889 B2 | 10/2008 | Engstrom et al. | |
| 7,597,791 B2 * | 10/2009 | Huang et al. | 204/600 |
| 7,695,956 B2 | 4/2010 | Tsinberg et al. | |
| RE42,315 E | 5/2011 | Lopez et al. | |
| 2001/0007749 A1 | 7/2001 | Feinberg | |
| 2001/0018192 A1 | 8/2001 | Terstappen et al. | |
| 2001/0036672 A1 | 11/2001 | Anderson et al. | |
| 2001/0053958 A1 | 12/2001 | Ried et al. | |
| 2002/0005354 A1 | 1/2002 | Spence et al. | |
| 2002/0006621 A1 | 1/2002 | Bianchi | |
| 2002/0009738 A1 | 1/2002 | Houghton et al. | |
| 2002/0012931 A1 | 1/2002 | Waldman et al. | |
| 2002/0019001 A1 | 2/2002 | Light | |
| 2002/0028431 A1 | 3/2002 | Julien | |
| 2002/0058332 A1 | 5/2002 | Quake et al. | |
| 2002/0076825 A1 | 6/2002 | Cheng et al. | |
| 2002/0086329 A1 | 7/2002 | Shvets et al. | |
| 2002/0090741 A1 | 7/2002 | Jurgensen et al. | |
| 2002/0098535 A1 | 7/2002 | Wang et al. | |
| 2002/0106715 A1 | 8/2002 | Huberman et al. | |
| 2002/0108859 A1 | 8/2002 | Wang et al. | |
| 2002/0110835 A1 | 8/2002 | Kumar | |
| 2002/0115163 A1 | 8/2002 | Wang et al. | |
| 2002/0115164 A1 | 8/2002 | Wang et al. | |
| 2002/0115201 A1 | 8/2002 | Barenburg et al. | |
| 2002/0123078 A1 | 9/2002 | Seul et al. | |
| 2002/0123112 A1 | 9/2002 | Wang et al. | |
| 2002/0127616 A1 | 9/2002 | Burchell et al. | |
| 2002/0132315 A1 | 9/2002 | Wang et al. | |
| 2002/0132316 A1 | 9/2002 | Wang et al. | |
| 2002/0137088 A1 | 9/2002 | Bianchi | |
| 2002/0142471 A1 | 10/2002 | Handique et al. | |
| 2002/0160363 A1 | 10/2002 | McDevitt et al. | |
| 2002/0164825 A1 | 11/2002 | Chen | |
| 2002/0172987 A1 | 11/2002 | Terstappen et al. | |
| 2002/0173043 A1 | 11/2002 | Merabet et al. | |
| 2003/0017514 A1 | 1/2003 | Pachmann et al. | |
| 2003/0036054 A1 | 2/2003 | Ladisch et al. | |

| | | | |
|---|---|---|---|
| 2003/0036100 A1 | 2/2003 | Fisk et al. | |
| 2003/0044832 A1 | 3/2003 | Blankenstein | |
| 2003/0049563 A1 | 3/2003 | Iida et al. | |
| 2003/0072682 A1 | 4/2003 | Kikinis | |
| 2003/0077292 A1 | 4/2003 | Hanash et al. | |
| 2003/0082148 A1 | 5/2003 | Ludwig et al. | |
| 2003/0087292 A1 | 5/2003 | Chen et al. | |
| 2003/0104461 A1 | 6/2003 | Muehlbauer et al. | |
| 2003/0113528 A1 | 6/2003 | Moya et al. | |
| 2003/0119077 A1 | 6/2003 | Ts'o et al. | |
| 2003/0119724 A1 | 6/2003 | Ts'o et al. | |
| 2003/0129676 A1 | 7/2003 | Terstappen et al. | |
| 2003/0134416 A1 | 7/2003 | Yamanishi et al. | |
| 2003/0153085 A1 | 8/2003 | Leary et al. | |
| 2003/0159999 A1 | 8/2003 | Oakey et al. | |
| 2003/0165852 A1 | 9/2003 | Schueler et al. | |
| 2003/0165927 A1 | 9/2003 | Hulten | |
| 2003/0170631 A1 | 9/2003 | Houghton et al. | |
| 2003/0170703 A1 | 9/2003 | Piper et al. | |
| 2003/0175990 A1 | 9/2003 | Hayenga et al. | |
| 2003/0178641 A1 | 9/2003 | Blair et al. | |
| 2003/0180754 A1 | 9/2003 | Bergholtz et al. | |
| 2003/0180762 A1 | 9/2003 | Tuma et al. | |
| 2003/0186889 A1 | 10/2003 | Forssmann | |
| 2003/0190602 A1 | 10/2003 | Pressman et al. | |
| 2003/0199685 A1 | 10/2003 | Pressman et al. | |
| 2003/0206901 A1 | 11/2003 | Chen | |
| 2003/0232350 A1 | 12/2003 | Afar et al. | |
| 2003/0234210 A1 | 12/2003 | Deshpande et al. | |
| 2004/0005582 A1 | 1/2004 | Shipwash | |
| 2004/0009471 A1 | 1/2004 | Cao | |
| 2004/0018116 A1 | 1/2004 | Desmond et al. | |
| 2004/0018509 A1 | 1/2004 | Bianchi | |
| 2004/0018611 A1 | 1/2004 | Ward et al. | |
| 2004/0019300 A1 | 1/2004 | Leonard | |
| 2004/0023222 A1 | 2/2004 | Russell et al. | |
| 2004/0043506 A1 | 3/2004 | Haussecker et al. | |
| 2004/0048360 A1 | 3/2004 | Wada et al. | |
| 2004/0063162 A1 | 4/2004 | Dunlay et al. | |
| 2004/0063163 A1 | 4/2004 | Buffiere et al. | |
| 2004/0072278 A1 | 4/2004 | Chou et al. | |
| 2004/0077105 A1 | 4/2004 | Wu et al. | |
| 2004/0101444 A1 | 5/2004 | Sommers et al. | |
| 2004/0121343 A1 | 6/2004 | Buechler et al. | |
| 2004/0142463 A1 | 7/2004 | Walker et al. | |
| 2004/0144651 A1 | 7/2004 | Huang et al. | |
| 2004/0166555 A1 | 8/2004 | Braff et al. | |
| 2004/0214240 A1 | 10/2004 | Cao | |
| 2004/0232074 A1 | 11/2004 | Peters et al. | |
| 2004/0241653 A1 | 12/2004 | Feinstein et al. | |
| 2004/0241707 A1 | 12/2004 | Gao et al. | |
| 2004/0245102 A1 | 12/2004 | Gilbert et al. | |
| 2005/0003351 A1 | 1/2005 | Fejgin et al. | |
| 2005/0014208 A1 | 1/2005 | Krehan et al. | |
| 2005/0042685 A1 | 2/2005 | Albert et al. | |
| 2005/0042766 A1 | 2/2005 | Ohman et al. | |
| 2005/0049793 A1 | 3/2005 | Paterlini-Brechot | |
| 2005/0069886 A1 | 3/2005 | Sun et al. | |
| 2005/0092662 A1 | 5/2005 | Gilbert et al. | |
| 2005/0100951 A1 | 5/2005 | Pircher | |
| 2005/0118591 A1 | 6/2005 | Tamak et al. | |
| 2005/0123454 A1 | 6/2005 | Cox | |
| 2005/0124009 A1 | 6/2005 | Van Weeghel et al. | |
| 2005/0129582 A1 | 6/2005 | Breidford et al. | |
| 2005/0136551 A1 | 6/2005 | Mpock | |
| 2005/0142663 A1 | 6/2005 | Parthasarathy et al. | |
| 2005/0145497 A1 | 7/2005 | Gilbert et al. | |
| 2005/0147977 A1 | 7/2005 | Koo et al. | |
| 2005/0153329 A1 | 7/2005 | Hakansson et al. | |
| 2005/0153342 A1 | 7/2005 | Chen | |
| 2005/0164158 A1 | 7/2005 | Wang et al. | |
| 2005/0170373 A1 | 8/2005 | Monforte | |
| 2005/0170418 A1 | 8/2005 | Moreland et al. | |
| 2005/0175505 A1 | 8/2005 | Cantor et al. | |
| 2005/0175981 A1 | 8/2005 | Voldman et al. | |
| 2005/0175996 A1 | 8/2005 | Chen | |
| 2005/0181353 A1 | 8/2005 | Rao et al. | |
| 2005/0181463 A1 | 8/2005 | Rao et al. | |
| 2005/0191636 A1 | 9/2005 | Hahn | |
| 2005/0207940 A1 | 9/2005 | Butler et al. | |
| 2005/0211556 A1 | 9/2005 | Childers et al. | |
| 2005/0214855 A1 | 9/2005 | Wagner et al. | |
| 2005/0236314 A1 | 10/2005 | Neyer et al. | |
| 2005/0239101 A1 | 10/2005 | Sukumar et al. | |
| 2005/0244843 A1 | 11/2005 | Chen et al. | |
| 2005/0249635 A1 | 11/2005 | Okun et al. | |
| 2005/0250111 A1 | 11/2005 | Xie et al. | |
| 2005/0250199 A1 | 11/2005 | Anderson et al. | |
| 2005/0252840 A1 | 11/2005 | Arnold et al. | |
| 2005/0255001 A1 | 11/2005 | Padmanabhan et al. | |
| 2005/0262577 A1 | 11/2005 | Guelly et al. | |
| 2005/0266433 A1 | 12/2005 | Kapur et al. | |
| 2005/0272049 A1 | 12/2005 | Banerjee et al. | |
| 2005/0272103 A1 | 12/2005 | Chen | |
| 2005/0282196 A1 | 12/2005 | Costa | |
| 2005/0282220 A1 | 12/2005 | Prober et al. | |
| 2005/0282293 A1 | 12/2005 | Cosman et al. | |
| 2006/0008807 A1 | 1/2006 | O'Hara et al. | |
| 2006/0008824 A1 | 1/2006 | Ronaghi et al. | |
| 2006/0019235 A1 | 1/2006 | Soen et al. | |
| 2006/0051265 A1 | 3/2006 | Mohamed et al. | |
| 2006/0051775 A1 | 3/2006 | Bianchi et al. | |
| 2006/0060767 A1 | 3/2006 | Wang et al. | |
| 2006/0121624 A1 | 6/2006 | Huang et al. | |
| 2006/0128006 A1 | 6/2006 | Gerhardt et al. | |
| 2006/0134599 A1 | 6/2006 | Toner et al. | |
| 2006/0160243 A1 | 7/2006 | Tang et al. | |
| 2006/0223178 A1 | 10/2006 | Barber et al. | |
| 2006/0252054 A1 | 11/2006 | Lin et al. | |
| 2006/0252087 A1 | 11/2006 | Tang et al. | |
| 2006/0285996 A1 | 12/2006 | Ohman et al. | |
| 2007/0026381 A1 | 2/2007 | Huang et al. | |
| 2007/0026413 A1 | 2/2007 | Toner et al. | |
| 2007/0026414 A1 | 2/2007 | Fuchs et al. | |
| 2007/0026415 A1 | 2/2007 | Fuchs et al. | |
| 2007/0026416 A1 | 2/2007 | Fuchs et al. | |
| 2007/0026417 A1 | 2/2007 | Fuchs et al. | |
| 2007/0026418 A1 | 2/2007 | Fuchs et al. | |
| 2007/0026419 A1 | 2/2007 | Fuchs et al. | |
| 2007/0026469 A1 | 2/2007 | Fuchs et al. | |
| 2007/0042339 A1 | 2/2007 | Toner et al. | |
| 2007/0059680 A1 | 3/2007 | Kapur et al. | |
| 2007/0059683 A1 | 3/2007 | Barber et al. | |
| 2007/0059716 A1 | 3/2007 | Balis et al. | |
| 2007/0059718 A1 | 3/2007 | Toner et al. | |
| 2007/0059719 A1 | 3/2007 | Grisham et al. | |
| 2007/0059774 A1 | 3/2007 | Grisham et al. | |
| 2007/0059781 A1 | 3/2007 | Kapur et al. | |
| 2007/0071762 A1 | 3/2007 | Ts'o et al. | |
| 2007/0072290 A1 | 3/2007 | Hvichia | |
| 2007/0099207 A1 | 5/2007 | Fuchs et al. | |
| 2007/0131622 A1 | 6/2007 | Oakey et al. | |
| 2007/0172903 A1 | 7/2007 | Toner et al. | |
| 2007/0196820 A1 | 8/2007 | Kapur et al. | |
| 2007/0196869 A1 | 8/2007 | Perez et al. | |
| 2007/0231851 A1 | 10/2007 | Toner et al. | |
| 2007/0264675 A1 | 11/2007 | Toner et al. | |
| 2008/0093306 A1 | 4/2008 | Oakey et al. | |
| 2008/0113358 A1 | 5/2008 | Kapur et al. | |
| 2008/0124721 A1 | 5/2008 | Fuchs | |
| 2008/0138809 A1 | 6/2008 | Kapur et al. | |
| 2010/0233693 A1 | 9/2010 | Kopf-Sill et al. | |
| 2010/0233694 A1 | 9/2010 | Kopf-Sill et al. | |

FOREIGN PATENT DOCUMENTS

| | | |
|---|---|---|
| DE | 19712309 | 5/1998 |
| EP | 0057907 | 8/1982 |
| EP | 0094193 | 11/1983 |
| EP | 0094193 A3 | 10/1984 |
| EP | 0405972 | 1/1991 |
| EP | 0637996 | 2/1995 |
| EP | 0689051 | 12/1995 |
| EP | 0444115 | 8/1996 |
| EP | 0739240 | 10/1996 |
| EP | 0791659 | 8/1997 |
| EP | 0430402 | 1/1999 |
| EP | 0919812 | 6/1999 |
| EP | 0920627 | 6/1999 |

| | | |
|---|---|---|
| EP | 0970365 | 1/2000 |
| EP | 1221342 | 7/2002 |
| EP | 1262776 | 12/2002 |
| EP | 1221342 A3 | 5/2003 |
| EP | 1328803 | 7/2003 |
| EP | 1338894 | 8/2003 |
| EP | 783694 B1 | 11/2003 |
| EP | 1198595 | 11/2003 |
| EP | 1418003 | 5/2004 |
| EP | 1462800 | 9/2004 |
| EP | 1499706 A2 | 1/2005 |
| EP | 1561507 | 8/2005 |
| EP | 1409727 | 11/2005 |
| FR | 2659347 | 9/1991 |
| GB | 2238619 | 6/1991 |
| GB | 2239311 | 6/1991 |
| JP | 2004045358 | 2/2004 |
| JP | 2004351309 | 12/2004 |
| WO | WO 85/02201 | 5/1985 |
| WO | WO 86/06170 | 10/1986 |
| WO | WO 90/06509 | 6/1990 |
| WO | WO 91/07660 | 5/1991 |
| WO | WO 91/07661 | 5/1991 |
| WO | WO 91/13338 | 5/1991 |
| WO | WO 91/08304 | 6/1991 |
| WO | WO 93/22053 | 11/1993 |
| WO | WO 93/22055 | 11/1993 |
| WO | WO 93/22055 A3 | 3/1994 |
| WO | WO 94/29707 | 12/1994 |
| WO | WO 96/32467 | 10/1996 |
| WO | WO 97/46882 | 12/1997 |
| WO | WO 98/00231 A1 | 1/1998 |
| WO | WO 98/08931 | 3/1998 |
| WO | WO 98/10267 | 3/1998 |
| WO | WO 98/12539 | 3/1998 |
| WO | WO 98/22819 | 5/1998 |
| WO | WO 98/31839 | 7/1998 |
| WO | WO 98/40746 | 9/1998 |
| WO | WO 98/57159 | 12/1998 |
| WO | WO 99/31503 | 6/1999 |
| WO | WO 99/44064 | 9/1999 |
| WO | WO 99/61888 | 12/1999 |
| WO | WO 00/00816 | 1/2000 |
| WO | WO 00/37163 | 6/2000 |
| WO | WO 00/62931 | 10/2000 |
| WO | WO 01/35071 | 5/2001 |
| WO | WO 01/37958 | 5/2001 |
| WO | WO 01/51668 | 7/2001 |
| WO | WO 01/71026 | 9/2001 |
| WO | WO 01/81621 | 11/2001 |
| WO | WO 02/07302 | 1/2002 |
| WO | WO 02/08751 | 1/2002 |
| WO | WO 02/12896 | 2/2002 |
| WO | WO 02/28523 | 4/2002 |
| WO | WO 02/30562 | 4/2002 |
| WO | WO 02/31506 | 4/2002 |
| WO | WO 02/43771 A2 | 6/2002 |
| WO | WO 02/44318 | 6/2002 |
| WO | WO 02/44319 | 6/2002 |
| WO | WO 02/44689 | 6/2002 |
| WO | WO 02/073204 | 9/2002 |
| WO | WO 03/000418 | 1/2003 |
| WO | WO 03/018198 | 3/2003 |
| WO | WO 03/018757 | 3/2003 |
| WO | WO 03/019141 | 3/2003 |
| WO | WO 03/023057 | 3/2003 |
| WO | WO 03/031938 | 4/2003 |
| WO | WO 03/035894 | 5/2003 |
| WO | WO 03/035895 | 5/2003 |
| WO | WO 03/044224 | 5/2003 |
| WO | WO 02/43771 A3 | 8/2003 |
| WO | WO 03/069421 | 8/2003 |
| WO | WO 03/071277 | 8/2003 |
| WO | WO 03/071278 | 8/2003 |
| WO | WO 03/078972 A1 | 9/2003 |
| WO | WO 03/079006 | 9/2003 |
| WO | WO 03/085379 | 10/2003 |
| WO | WO 03/031938 A3 | 11/2003 |
| WO | WO 03/093795 | 11/2003 |
| WO | WO 03/085379 A3 | 12/2003 |
| WO | WO 2004/004906 | 1/2004 |
| WO | WO 2004/015411 | 2/2004 |
| WO | WO 2004/024327 | 3/2004 |
| WO | WO 2004/025251 | 3/2004 |
| WO | WO 2004/029221 | 4/2004 |
| WO | WO 2004/029221 A3 | 5/2004 |
| WO | WO 2004/037374 | 5/2004 |
| WO | WO 2004/044236 | 5/2004 |
| WO | WO 2004/056978 | 7/2004 |
| WO | WO 2004/076643 | 9/2004 |
| WO | WO 2004/101762 | 11/2004 |
| WO | WO 2004/113877 | 12/2004 |
| WO | WO 2005/028663 | 3/2005 |
| WO | WO 2005/042713 | 5/2005 |
| WO | WO 2005/043121 | 5/2005 |
| WO | WO 2005/047529 | 5/2005 |
| WO | WO 2005/049168 | 6/2005 |
| WO | WO 2005/058937 | 6/2005 |
| WO | WO 2005/061075 | 7/2005 |
| WO | WO 2005/068503 | 7/2005 |
| WO | WO 2005/084374 | 9/2005 |
| WO | WO 2005/084380 | 9/2005 |
| WO | WO 2005/085861 | 9/2005 |
| WO | WO 2005/089253 | 9/2005 |
| WO | WO 2005/091756 | 10/2005 |
| WO | WO 2005/098046 | 10/2005 |
| WO | WO 2005/108621 | 11/2005 |
| WO | WO 2005/108963 | 11/2005 |
| WO | WO 2005/109238 | 11/2005 |
| WO | WO 2005/116264 | 12/2005 |
| WO | WO 2005/121362 | 12/2005 |
| WO | WO 2006/012820 | 2/2006 |
| WO | WO 2006/133208 | 2/2006 |
| WO | WO 2006/035846 | 4/2006 |
| WO | WO 2006/037561 | 4/2006 |
| WO | WO 2006/076567 | 7/2006 |
| WO | WO 2006/078470 | 7/2006 |
| WO | WO 2006/108087 | 10/2006 |
| WO | WO 2007/035414 | 3/2007 |
| WO | WO 2007/035498 | 3/2007 |

OTHER PUBLICATIONS

"Cancer Genetics" *Am J Hum Genet* 43(3):A35 (1988).

Adinolfi, "On a Non-Invasive Approach to Prenatal Diagnosis Based on the Detection of Fetal Nucleated Cells in Maternal Blood Samples," *Prenat Diagn* 11:799-804 (1991).

Adinolfi et al., "Gene Amplification to Detect Fetal Nucleated Cells in Pregnant Women," *Lancet* 2:328-329 (1989).

Al-Mufti et al., "Distribution of fetal and embryonic hemoglobins in fetal erythroblasts enriched from maternal blood," *Haematologica* 86:357-362 (2001).

Al-Saadi, "Cystic Hygroma Cells as Source for Prenatal Diagnosis," *Amer J Hum Genet* Supplemental to vol. 45, No. 4:A252-0990 (1989).

Alvarez, "Morphology and Physiopathology of the Human Placenta," *Obstet Gynecol* 23:813-817;819-825 (1964).

Anderson et al., "Simultaneous Fluorescence-Activated Cell. Sorter Analysis of Two Distinct Transcriptional Elements within a Single Cell Using Engineered Green Fluorescent Proteins," *PNAS* 93:8508-8511 (1996).

Archer et al., "Cell Reactions to Dielectrophoretic Manipulation," *Biochem Biophys Res Comm* 257:687-698 (1999).

Armani et al., "Re-configurable Fluid Circuits by PDMS Elastomer Micromachining," Proc. 12th International Conference on MEMS (MEMS '99) 17-21:222-227 (1999).

Associated Press "Blood Test May Erase Risk of Amniocentesis," The Worcester Telegram & Gazette Oct. 9, 1991:A7.

Basch et al., "Cell Separation Using Positive Immunoselective Techniques," *J Immunol Methods* 56:269-280 (1983).

Bauer, "Advances in Cell Separation: Recent Developments in Counterflow Centrifugal Elutriation and Continuous Flow Cell Separation," *J Chromatogr B* 722:55-69 (1999).

Becker et al., "Fabrication of Microstructures with High Aspect Ratios and Great Structural Heights by Synchrotron Radiation Lithography, Galvanoforming, and Plastic Moulding (LIGA Process)," *Microelectronic Eng* 4:35-56 (1986).
Becker et al., "Planar Quartz Chips with Submicron Channels for Two-Dimensional Capillary Electrophoresis Applications," *J Micromech Microeng* 8:24-28 (1998).
Beebe et al., "Functional Hydrogel Structures for Autonomous Flow Control Inside Microfluidic Channels," *Nature* 404:588-590 (2000).
Benincasa et al., "Cell Sorting by One Gravity SPLITT Fractionation," *Anal Chem* 77:5294-5301 (2005).
Berenson et al., "Antigen CD34* Marrow Cells Engraft Lethally Irradiated Baboons," *J Clin Invest* 81:951-955 (1988).
Berenson et al., "Positive Selection of Viable Cell Populations Using Avidin-Biotin Immunoadsorption," *J Immunol Methods* 91:11-19 (1986).
Berenson et al., "Cellular Immunoabsorption Using Monoclonal Antibodies," *Transplantation* 38:136-143 (1984).
Berg H.C., *Random Walks in Biology*, Ch. 4, Princeton University Press. Princeton, NJ; pp. 48-64 (1993).
Berger et al. "Design of a microfabricated magnetic cell separator" *Electrophoresis* 22:3883-3892 (2001).
Beroud et al. "Prenatal diagnosis of spinal muscular atrophy by genetic analysis of circulating fetal cells," Lancet 2003, 361:1013-1014.
Bertero et al., "Circulating 'Trophoblast' Cells in Pregnancy Have Maternal Genetic Markers," *Prenat Diagn* 8:585-590 (1988).
Bianchi et al.. "Fetal Nucleated Erythrocytes (FNRBC) in Maternal Blood: Erythroid-Specific Antibodies Improve Detection," *Am J Hum Genet Supplement* to 51(4):996 (1992).
Bianchi et al., "Possible Effect of Gestational Age on the Detection of Fetal Nucleated Erythrocytes in Maternal Blood," *Prenat Diagn* 11:523-528 (1991).
Bianchi et al., "Isolation of Fetal DNA from Nucleated Erythrocytes in Maternal Blood," *PNAS* 87:3279-3283 (1990).
Bianchi et al., "Isolation of Male Fetal DNA from Nucleated Erythrocytes (NRBC) in Maternal Blood," *Pediatr Res* May 1-4, 1989: 139A Abstract 818 (1989).
Bianchi et al., "Demonstration of Fetal Gene Sequences in Nucleated Erythrocytes Isolated from Maternal Blood," *Am J Hum Genet* Supplement to 45:A252 Abstract 0991 (1989).
Bianchi et al., "Direct Hybridization to DNA from Small Numbers of Flow-Sorted Nucleated Newborn Cells," *Cytometry* 8:197-202 (1987).
Bick et al., "Prenatal Diagnosis and Investigation of a Fetus with Chondrodysplasia Punctata, Ichthyosis and Kallmann Syndrome due to an Xp Deletion" *Prenat Diagn* 12:19-29 (1992).
Bickers et al., "Fetomaternal Transfusion Following Trauma," *Obstet Gynecol* 61:258-259 (1983).
Bigbee et al., "Monoclonal Antibodies Specific for the M- and N-Forms of Human Glycophorin A," *Mol Immunol* 20:1353-1362 (1983).
Black et al., "Complex mosaicism on chorionic sampling confirmed postnatally," *Amer J Hum Genet* Supplemental to vol. 45, No. 4:A252-0993 (1989).
Bohmer et al., "Differential development of fetal and adult haemoglobin profiles in colony culture: isolation of fetal nucleated red cells by two-colour fluorescence labelling," *Brit J Haematol* 103:351-360 (1998).
Bousse et al., "Micromachined Multichannel Systems for the Measurement of Cellular Metabolism," *Sensors and Actuators B* 20:145-150 (1994).
Boyer et al., "Enrichment of Erythrocytes of Fetal Origin from Adult-Fetal Blood Mixtures via Selective Hemolysis of Adult Blood Cells: An Aid to Antenatal Diagnosis of Hemoglobinopathies." *Blood* 47:883-897 (1976).
Brison et al., "General Method for Cloning Amplified DNA by Differential Screening with Genomic Probes," *Mol Cell Biol* 2:578-587 (1982).
Brizot et al., "Maternal serum pregnancy-associated plasma protein a and fetal nuchal translucency thickness for the prediction of fetal trisomies in early pregnancy," *Obstet Gynecol* 84(6):918-22 (1994).

Brizot et al., "Maternal serum hCG and fetal nuchal translucency thickness for the prediction of fetal trisomies in the first trimester of pregnancy," *British J Obstet Gynaecol* 102:127-132 (1995).
Brody et al., "Biotechnology at Low Reynolds Numbers," *Biophys J* 71:3430-3441 (1996).
Brody et al., "Deformation and flow of red blood cells in a synthetic lattice: evidence for an active cytoskeleton." *Biophys J* 68:2224-2232 (1995).
Bulmer et al., "Antigen Expression by Trophoblast Populations in the Human Placenta and Their Possible Immunobiological Relevance," *Placenta* 6:127-140 (1985).
Butterworth et al., "Human Cytotrophoblast Populations Studied by Monoclonal Antibodies Using Single and Double Biotin-Avidin-Peroxidase Immunocytochemistry," *J Histochem Cytochem* 33:977-983 (1985).
Cai et al., "Rapid Prenatal Diagnosis of β Thalassemia Using DNA Amplification and Nonradioactive Probes," *Blood* 73:372-374 (1989).
Cai et al., "A New TATA Box Mutation Detected at Prenatal Diagnosis for β-Thalassemia," *Am J Hum Genet* 45:112-114 (1989).
Calin et al., "A microRNA signature associated with prognosis and progression in chronic lymphocytic leukemia," *N Engl J Med* 353:1793-1801 (2005).
Carlson et al., "Self-Sorting of White Blood Cells in a Lattice," *Physical Review Letters* 79:2149-2152 (1997).
Chamberlain et al., "Deletion Screening of the Duchenne Muscular Dystrophy Locus via Multiplex DNA Amplification," *Nucleic Acids Res* 16:11141-11156 (1988).
Chang et al., "Biomimetic technique for adhesion-based collection and separation of cells in a microfluidic channel," *Lab Chip* 5:64-73 (2005).
Chinn et al., "Reactive Ion Etching for Submicron Structures," *J Vac Sci Technol* 19:1418-1422 (1981).
Chiu et al., "Patterned Deposition of Cells and Proteins Onto Surfaces by Using Three-Dimensional Microfluidic Systems," *PNAS* 2408-2413 (2000).
Choolani et al., "Characterization of first trimester fetal erythroblasts for non-invasive prenatal diagnosis," *Mol Hum Reproduction* 9:227-235 (2003).
Chou et al., a Microfabricated Device for Sizing and Sorting DNA Molecules. *PNAS* 96:11-13 (1999).
Chou et al., "Sorting by Diffusion: An Asymmetric Obstacle Course for Continuous Molecular Separation," *PNAS* 96:13762-13765 (1999).
Christensen et al., "Fetal Cells in Maternal Blood: A Comparison of Methods for Cell Isolation and Identification," *Fetal Diagnosis and Therapy* 20:106-112 (2005).
Christel et al., "High Aspect Ratio Silicon Microstructures for Nucleic Acid Extraction. Solid-State Sensor and Actuator Workshop," Hilton Head, SC, Jun. 8-11, 363-366 (1998).
Chueh et al., "Prenatal Diagnosis Using Fetal Cells in the Maternal Circulation," *Semin Perinatol* 14:471-482 (1990).
Chueh et al., "Prenatal Diagnosis Using Fetal Cells in the Maternal Circulation," *West J Med* 159:308-311 (1993).
Chueh et al., "The Search for Fetal Cells in the Maternal Circulation," *J. Perinatol. Med.* 19:411-420 (1991).
Chueng et al., "Prenatal diagnosis of sickle cell anaemia and thalassaemia by analysis of fetal cells in maternal blood," *Nat Genet.* 14(3):264-8 (1996).
Clayton et al., "Fetal Erythrocytes in the Maternal Circulation of Pregnant Women," *Obstetr Gynecol* 23:915-919 (1964).
Cohen et al., "Mechanisms of Isoimmunization II. Transplacental Passage and Postnatal Survival of Fetal Erythrocytes in Heterospecific Pregnancies," *Blood* 30:796-804 (1967).
Covone et al., "Trophoblast Cells in Peripheral Blood from Pregnant Women," *Lancet* 2:841-843 (1984).
Covone et al., "Analysis of Peripheral Maternal Blood Samples for the Presence of Placenta-Derived Cells Using Y-Specific Probes and McAb H315," *Prenat Diagn* 8:591-607 (1988).
Cremer et al., "Detection of Chromosome Aberrations in Metaphase and Interphase Tumor Cells by in Situ Hybridization Using Chromosome-Specific Library Probes," *Hum Genet* 80:235-246 (1988).

Cremer et al., "Detection of Chromosome Aberrations in the Human Interphase Nucleus by Visualization of Specific Target DNAs with Radioactive and Non-Radioactive in Situ Hybridization Techniques: Diagnosis of Trisomy 18 with Probe L1.84," *Hum Genet* 74:346-352 (1986).

Das et al., "Dielectrophoretic segregation of different human cell types on microscope slides." *Anal Chem* 77:2708-2719 (2005).

Delamarche et al., "Microfluidic Networks for Chemical Patterning of Substrates: Design and Application to Bioassays," *J Amer Chem Soc* 120:500-508 (1998).

Delamarche et al., "Patterned Delivery of Immunoglobulins to Surfaces Using Microfluidic Networks." *Science.* 276:779-781 (1997).

Deng et al., "Manipulation of Magnetic Microbeads in Suspension Using Micromagnetic Systems Fabricated with Soft Lithography," *Appl Phys Lett* 78(12):1775-1777 (2001).

Deshmukh et al., "Continuous Micromixer with Pulsatile Micropumps," *Solid-State Sensor and Actuator Workshop, Hilton Head Island, South Carolina*; Jun. 4-8, 2000, pp. 73-76 (2000).

DiLella et al., "Screening for Phenylketonuria Mutations by DNA Amplification with the Polymerase Chain Reaction," *Lancet* 1(8584):497-499 (1988).

Douglas et al., "Trophoblast in the Circulating Blood During Pregnancy," *Am J Obstet Gynecol* 78:960-973 (1959).

Doyle et al., "Self-Assembled Magnetic Matrices for DNA Separation Chips," *Science* 295:2237 (2002).

Duke et al., "Microfabricated sieve for the continuous sorting of macromolecules" *Phys Rev Lett* 80:1552-1555 (1998).

Dutta et al., "Electroosmotic Flow Control in Complex Microgeometries," *J Microelectromech Sys* 11:36-44 (2002).

Eigen et al., "Sorting Single Molecules: Application to Diagnostics and Evolutionary Biotechnology," *PNAS* 91:5740-5747 (1994).

Elias, "Prenatal Blood Test Can Signal Genetic Disorders," The Boston Globe. Oct. 8, 1991:4.

Evans et al., "The Bubble Spring and Channel (BSAC) Valve: An Actuated, Bi-Stable Mechanical Valve for In-Plane Fluid Control," *Transducers '99. Sendai, Japan*; Jun. 7-10, 1999 (1999).

Farber et al., "Demonstration of Spontaneous XX/XY Chimerism by DNA Fingerprinting," *Hum. Genet.* 82:197-198 (1989).

Farooqui et al., "Microfabrication of Submicron Nozzles in Silicon Nitride," *J. Microelectromech. Systems* 1(2):8688 (1992).

Fibach et al., "Proliferation and Maturation of Human Erythroid Progenitors in Liquid Culture," *Blood* 73:100-103 (1989).

Fiedler et al., "Dielectrophoretic Sorting of Particles and Cells in a Microsystem," *Analytical Chem*; pp. 1909-1915 (1998).

Forestier et al., "Hematological Values of 163 Normal Fetuses between 18 and 30 Weeks of Gestation," Pediatr. Res. 20:342-346 (1986).

Freemantle, "Downsizing Chemistry. Chemical analysis and synthesis on microchips promise a variety of potential benefits," *Chemical & Engineering News*. pp. 27-36 (1999).

Fu et al., "An Integrated Microfabricated Cell Sorter," *Anal. Chem.* 74:2451-2457 (2002).

Fu et al., "A Microfabricated Fluorescence-Activated Cell Sorter," *Nat Biotech*. 17:1109-1111 (1999).

Fuhr et al., "Biological Application of Microstructures," *Topics in Current Chemistry*. 194:83-116 (1997).

Galbraith et al., "Demonstration of Transferrin Receptors on Human Placental Trophoblast," *Blood* 55:240-242 (1980).

Gänshirt-Ahlert et al., "Magnetic Cell Sorting and the Transferrin Receptor as Potential Means of Prenatal Diagnosis from Maternal Blood," *Am. J. Obstet. Gynecol.* 166:1350-1355 (1992).

Gänshirt-Ahlert et al., "Noninvasive Prenatal Diagnosis: Triple Density Gradient, Magnetic Activated Cell Sorting and FISH prove to Be an Efficient and Reproducible Method for Detection of Fetal Aneuploidies from Maternal Blood," *Am. J. Hum. Genet.* Supplement to 51:182 (1992).

Gasparini et al., "First-Trimester Prenatal Diagnosis of Cystic Fibrosis Using the Polymerase Chain Reaction: Report of Eight Cases," *Prenat. Diagn.* 9:349-355 (1989).

Giddings, "Chemistry: 'Eddy' Diffusion in Chromatography," *Nature* 184(4683):357-358 (1959).

Giddings, "Field-Flow Fractionation: Analysis of Macromolecular, Colloidal, and Particulate Materials," *Science* 260:1456-1465 (1993).

Giddings, *Unified Separation Science*, John Wiley & Sons, Inc., Cover Page & Table of Contents only (1991).

Goldberg, "Test reveals gender early in pregnancy ethicists fear use in sex selection" Boston Globe, Jun. 27, 2005.

Graham, "Efficiency Comparison of Two Preparative Mechanisms for Magnetic Separation of Erythrocytes from Whole Blood," *J. Appl. Phys.* 52:2578-2580 (1981).

Greaves et al., "Expression of the OKT Monoclonal Antibody Defined Antigenic Determinants in Malignancy," *Int. J. Immunopharmacol.* 3(3):283-299 (1981).

Guérin et al., "A New *TaqI* BO Variant Detected with the p49 Probe on the Human Y Chromosome," *Nucleic Acids Res*. 16:7759 (1988).

Hall et al., "Isolation and Purification of CD34+ Fetal Cells from Maternal Blood," *Am. J. Hum. Genet*. Supplement to 51(4):1013 (1992).

Hames et al., eds. *Nucleic Acid Hybridisation: A Practical Approach*, Oxford: IRL Press Limited; 1985, pp. 190-193.

Han et al., "Separation of Long DNA Molecules in a Microfabricated Entropic Trap Array," *Science* 288:10261029 (2000).

Handyside et al., "Biopsy of Human Preimplantation Embryos and Sexing by DNA Amplification," *Lancet* 1(8634):347-349 (1989).

Hartmann et al., "Gene expression profiling of single cells on large-scale oligonucleotide arrays." *Nucleic Acids Research* 34(21): e143. (2006).

Hatch et al. "A rapid diffusion immunoassay in a T-sensor" *Nat Biotech* 19:461-465 (2001).

Henning et al., "Microfluidic MEMS," *Proc. IEEE Aerospace Conference* 1:471-486 (1998).

Hennerbichler et al., "Detection and relocation of cord blood nucleated red blood cells by laser scanning cytometry," *Cytometry* 48:87-92 (2002).

Herzenberg et al., "Fetal Cells in the Blood of Pregnant Women: Detection and Enrichment by Fluorescence-Activated Cell Sorting," *PNAS* 76:1453-1455 (1979).

Holzgreve et al., "Fetal Cells in the Maternal Circulation," *J. Reprod. Med.* 37:410-418 (1992).

Huang et al., "Continuous Particle Separation Through Deterministic Lateral Displacement," Science 304:987-990 (2004).

Huang et al., "Role of Molecular Size in Ratchet Fractionation," *Phys. Rev. Lett.* 89:178301 (2002).

Huang et al., "A DNA Prism for High-Speed Continuous Fractionation of Large DNA Molecules," *Nature Biotechnol.* 20:1048-1051 (2002).

Huang et al., "Electric Manipulation of Bioparticles and Macromolecules on Microfabricated Electrodes. Analytical Chemistry," pp. 1549-1559 (2001).

Huh et al., "Gravity-Driven Microhydrodynamics-Based Cell Sorter (microHYCS) for Rapid, Inexpensive, and Efficient Cell Separation and Size-Profiling," *2nd Annual International IEEE-EMBS Special Topic Conference on Microtechnologies in Medicine and Biology* Poster 180:466-469 (2002).

Huie et al., "Antibodies to human fetal erythroid cells from a nonimmune phage antibody library," *PNAS* 98(5): 2682-7 (2001).

Hviid, "In-Cell PCR Method for Specific Genotyping of Genomic DNA from One Individual in a Mixture of Cells from Two Individuals: A Model Study with Specific Relevance to Prenatal Diagnosis Based on Fetal Cells in Maternal Blood." *Clin. Chem.* 48:2115-23 (2002).

Iverson et al., "Detection and Isolation of Fetal Cells from Maternal Blood Using the Flourescence-Activated Cell Sorter (FACS)," *Prenatl. Diagn.* 1:61-73 (1981).

hiker, "Direct Observation of Reptation in Artificial Gel Environments," Bachelor of Arts thesis, Princeton University. (1991).

Jan et al., "Fetal Erythrocytes Detected and Separated from Maternal Blood by Electronic Fluorescent Cell Sorter," *Texas Rep. Biol. Med.* 31:575 (1973).

Jansen et al., "The effect of chorionic villus sampleing on the the number of fetal cells isolated from material blood and on maternal serum alpha-fetoprotein levels," *Prenatal Diagnosis* 17:953-959 (1997).

Jeon et al., "Generation of Solution and surface Gradients Using Microfluidic Systems," *Langmuir*. pp. 8311-8316 (2000).
Kamholz et al., "Quantitative Analysis of Molecular Interaction in a Microfluidic Channel: the T-Sensor," Analytical Chem pp. 5340-5347 (1999).
Kan et al., "Concentration of Fetal Red Blood Cells From a Mixture of Maternal and Fetal Blood by Anti-i Serum—An Aid to Prenatal Diagnosis of Hemoglobinopathies," *Blood* 43:411-415 (1974).
Kawata et al., "Transcriptional Control of HLA-A,B.C Antigen in Human Placental Cytotrophoblast Isolated Using Trophoblast- and HLA-Specific Monoclonal Antibodies and the Fluorescence-Activated Cell Sorter," *J. Exp. Med.* 160:633-651 (1984).
Kelly, "A Simpler, Safer Blood Test for Birth Defects," USA Today. Nov. 14, 1989:1D.
Kenis et al., "Microfabrication Inside Capillaries Using Multiphase Laminar Flow Patterning," *Science* 285:83-85 (1999).
Kim et al., "Polymer Microstructures Formed by Moulding in Capillaries," *Nature* 376:581-584 (1995).
Klinger et al., "Rapid Detection of Chromosome Aneuploidies in Uncultured Amniocytes by Using Fluorescence in Situ Hybridization (FISH)," *Am. J. Hum. Genet.* 51:55-65 (1992).
Kogan et al., "An Improved Method for Prenatal Diagnosis of Genetic Diseases by Analysis of Amplified DNA Sequences," *N. Engl. J. Med.* 317:985-990 (1987).
Kohn et al., "Elevated Maternal Serum Human Chorionic Gonadotropin Associated with a Chromosomal Deletion," *Prenat. Diagn.* 12:853-854 (1992).
de Kretser et al., "The Separation of Cell Populations using Monoclonal Antibodies attached to Sepharose." *Tissue Antigens* 16:317-325 (1980).
Krivacic et al., "A rare-cell detector for cancer." *PNAS* 101:10501-10504 (2004).
Kutch et al., "Racial Differences in Maternal Serum Human Chorionic Gonadotropin and Unconjugated Oestriol Levels," *Prenat. Diagn.* 13:191-195 (1993).
Kulozik et al., "Fetal Cell in the Maternal Circulation: Detection by Direct AFP-Immunoflourescence," *Hum. Genet.* 62:221-224 (1982).
Kumar et al., "Cell Separation: A Review," *Pathology* 16:53-62 (1984).
Kwok et al., "Avoiding False Positives with PCR," *Nature* 339:237-238 (1989).
Lanier et al., "Subpopulations of Human Natural Killer Cells Defined by Expression of the Leu-7 (HNK-1) and Leu-11 (NK-15) Antigens," *J. Immunol.* 131:1789-1796 (1983).
Latt, "Prenatal Genetic Diagnosis," in Schaffer's Diseases of the Newborn, eds. Avery and Taeusch. Philadelphia:W.B Saunders and Co., 24-36 (1984).
Lau et al., "A Rapid Screening Test for Antenatal Sex Determination," *Lancet* 1(8367):14-16 (1984).
Li et al., "Amplification and Analysis of DNA Sequences in Single Human Sperm and Diploid Cells," *Nature* 335:414-417 (1988).
Li et al., "Transport, Manipulation, and Reaction of Biological Cells On-Chip Using Electrokinetic Effects," *Analytical Chem* pp. 1564-1568 (1997).
Lichter et al., "Delineation of Individual Human Chromosomes in Metaphase and Interphase Cells by in Situ Suppression Hybridization Using Recombinant DNA Libraries," *Hum. Genet.* 80:224-234 (1988).
Lin et al., "Microbubble Powered Actuator," *1991 International Conference on Solid-State Sensors and Actuators. Digest of Technical Papers (Transducers '91)* pp. 1041-1044 (1991).
Lipinski et al., "Human Trophoblast Cell-Surface Antigens Defined by Monoclonal Antibodies," *PNAS* 78:5147-5150 (1981).
Lo et al., "False-Positive Results and the Polymerase Chain Reaction," *Lancet* 2(8612):679 (1988).
Lo et al., "Prenatal Sex Determination by Dna Amplification from Maternal Peripheral Blood," *Lancet* 2(8676):1363-1365 (1989).
Loken et al., "Flow Cytometric Analysis of Human Bone Marrow: I. Normal Erythroid Development," *Blood* 69:255-263 (1987).
Lloyd et al., "Intrapartum Fetomaternal Bleeding in Rh-Negative Women," *Obstet. Gynecol.* 56:285-287 (1980).
Macadam et al., "Standardization of Ultrasound Measurements in pregnancy dating for the purposes of triple marker screening," *Am J Hum Genet* Supplemental to vol. 51. No. 4: 1620 (1992).
Mahr et al., "Fluorescence in Situ Hybridization of Fetal Nucleated Red Blood Cells," *Am J Hum Genet* Supplement to 51(4):1621 (1992).
Maren et al., "Kinetics of carbonic anhydrase in whole red cells as measured by transfer of carbon dioxide and ammonia," *Mol Pharm* 6:430-440 (1970).
Maxwell et al., "A Microbubble-Powered Bioparticle Actuator," *J Microelectromech Sys* 12:630-640 (2003).
McCabe et al., "DNA Microextraction from Dried Blood Spots on Filter Paper Blotters: Potential Applications to Newborn Screening," *Hum. Genet.* 75:213-216 (1987).
Mehrishi et al., "Electrophoresis of Cells and the Biological Relevance of Surface Charge," *Electrophoresis* 23:1984-1994 (2002).
Melville et al., "Direct magnetic separation of red cells from whole blood," Nature 255:706 (1975).
Millar et al., "Normal Blood Cell Values in the Early Mid-Trimester Fetus," Prenat. Diagn. 5:367-373 (1985).
Mohamed et al., "Development of a rare cell fractionation device: application for cancer detection," *IEEE Trans Nanobioscience* 3(4): 251-6 (2004).
Moore et al., "Lymphocyte Fractionation Using Immunomagnetic Colloid and a Dipole Magnet Flow Cell Sorter," *J Biochem Biophys Methods* 37:11-33 (1998).
Mueller et al., "Identification of Extra-Villous Trophoblast Cells in Human Decidua Using an Apparently Unique Murine Monoclonal Antibody to Trophoblast," *Histochem. J.* 19:288-296 (1987).
Mueller et al., "Isolation of Fetal Trophoblast Cells from Peripheral Blood of Pregnant Women," *Lancet* 336(8709):197-200 (1990).
Muller et al., "Moderately Repeated DNA Sequences Specific for the Short Arm of the Human Y Chromosome are Present in XX Males and Reduced in Copy Number In an XY Female," *Nucleic Acids Res.* 14:1325-1340 (1986).
Mullis et al., "Specific Enzymatic Amplification of DNA in Vitro: The Polymerase Chain Reaction," *Cold Spring Harb. Symp. Quant. Biol.* 51:263-273 (1986).
Newman et al., "The Transferrin Receptor," *Trends Biochem. Sci.* 7:397-400 (1982).
Oakey et al., "Laminar Flow-Based Separations at the Microscale," *Biotechnology Progress*. pp. 1439-1442 (2002).
Oberle et al., "Genetic Screening for Hemophilia A (Classic Hemophilia) with a Polymorphic DNA Probe," *N Engl J Med* 312:682-686 (1985).
Ockenhouse et al., "Activation of Monocytes and Platelets by Monoclonal Antibodies or Malaria-Infected Erythrocytes Binding to the CD36 Surface Receptor in Vitro," *J Clin Invest* 84:468-475 (1989).
Olson et al., "An In Situ Flow Cytometer for the Optical Analysis of Individual Particles in Seawater," Available at http://www.whoi.edu/science/B/Olsonlab/insitu2001.htm. Accessed Apr. 24, 2006.
Pallavicini et al., "Analysis of Fetal Cells Sorted from Maternal Blood Using Fluorescence in Situ Hybridization," *Am J Hum Genet* Supplement to 51(4):1031 (1992).
Papavasiliou et al., "Electrolysis-Bubble Actuated Gate Valve," *Solid-State Sensor and Actuator Workshop, Hilton Head Island, SC.* Jun. 4-8, 2000; pp. 48-51 (2000).
Parano et al., "Noninvasive Prenatal Diagnosis of Chromosomal Aneuploidies by Isolation and Analysis of Fetal Cells from Maternal Blood," *Am J Med Genet* 101:262-267 (2001).
Paterlini-Brechot et al., "Circulating tumor cells (CTC) detection: Clinical impact and future directions." *Cancer Letter.* (In press, 2007).
Pawlik et al., "Prodrug Bioactivation and Oncolysis of Diffuse Liver Metastases by a Herpes Simplex Virus 1 Mutant That Expresses the CYP2B1 Transgene," *Cancer* 95:1171-1181 (2002).
Payne, "The Development and Persistence of Leukoagglutinins in Parous Women," *Blood* 19:411-424 (1962).
Pembrey et al., "Maternal Synthesis of Haemoglobin F in Pregnancy," *Lancet* 1(7816):1350-1354 (1973).

Peng et al., "Real-time detection of gene expression in cancer cells using molecular beacon imaging: new strategies for cancer research," *Cancer Res.* 65(5):1909-17 (2005).

Petersen et al., "The promise of miniaturized clinical diagnostic systems," IVD Technology Jul. (1998).

Pinkel et al., "Detection of Structural Chromosome Abberations in Metaphase Spreads and Interphase Nuclei by in Situ Hybridization High Complexity Probes Which Stain Entire Human Chromosomes," *Am J Hum Genet* Supplement to 43(3):0471 (1988).

Pinkel et al., "Fluorescence in Situ Hybridization with Human Chromosome-Specific Libraries: Detection of Trisomy 21 and Translocations of Chromosome 4," *PNAS* 85:9138-9142 (1988).

Pinkel et al., "Cytogenetic Analysis Using Quantitative, High-Sensitivity, Fluorescence Hybridization," *PNAS* 83:2934-2938 (1986).

Price et al., "Prenatal diagnosis with fetal cells isolated from maternal blood by multiparameter flow cytometry," *Am J Obstet Gynecol* 165:1731-1737 (1991).

Product literature for GEM, a system for blood testing: GEM Premier 3000. Avaiable at http://www.ilus.com/premier_gem3000_iqm.asp. Accessed Apr. 24, 2006.

Raeburn, "Fetal Blood Cells Found in Pregnant Women's Blood," Associated Press. Jul. 28, 1989.

Raymond et al., "Continuous Separation of High Molecular Weight Compounds Using a Microliter vol. Free-Flow Electrophoresis Microstructure," *Anal Chem* 68:2515-2522 (1996).

Ried et al., "Multicolor Fluorescence in Situ Hybridization for the Simultaneous Detection of Probe Sets for Chromosomes 13, 18, 21, X and Y in Uncultured Amniotic Fluid Cells," *Hum Mol Genet* 1:307-313 (1992).

Rolle et al., "Increase in number of circulating disseminated epithelial cells after surgery for non-small cell lung cancer monitored by MAINTRAC is a predictor for relapse: a preliminary report," *World Journal of Surgical Oncology* 3:18 (2005).

Ruan et al., "Identification of clinically significant tumor antigens by selecting phage antibody library on tumor cells in situ using laser capture microdissection," *Molecular & Cellular Proteomics* 5(12): 2364-73 (2006).

Saiki et al., "Diagnosis of Sickle Cell Anemia and β-Thalassemia with Enzymatically Amplified DNA and Nonradioactive Allele-Specific Oligonucleotide Probes," *N Engl J Med* 319:537-541 (1988).

Saltus, "New Test Speeds Detection of Birth Defects," The Boston Globe. Oct. 8, 1991:4.

Saltus, "Noninvasive Way Is Cited to Detect Down Syndrome in Fetuses," The Boston Globe. Nov. 12, 1992:8.

Sato et al., "Individual and Mass Operation of Biological Cells Using Micromechanical Silicon Devices," *Sens Actuators* A21-A23:948-953 (1990).

Schomburg et al., "Microfluidic Components in LIGA Technique," *J Micromech Microeng* 4:186-191 (1994).

Schröder, "Transplacental Passage of Blood Cells," *J Med Genet* 12:230-242 (1975).

Schröder et al., "Fetal Lymphocytes in the Maternal Blood," *Blood* 39:153-162 (1972).

Sethu et al., "Continuous Flow Microfluidic Device for Rapid Erythrocyte Lysis," *Anal. Chem*. 76:6247-6253 (2004).

Shoji et al., "Microflow Devices and Systems," *J Micromech Microeng* 4:157-171 (1994).

Simpson et al., "Elevated Second Trimester Maternal Serum Alpha Fetoprotein (MSAFP) Is More Predictive of Certain Pregnancy Complications than Elevated Third Trimester MSAFP: A Cohort Study," *Am J Hum Genet* Supplement to 51(4):A19-65 (1992).

Simpson et al., "Prenatal Genetic Diagnosis," Ch. 6, Genetics in Obstetrics and Gynecology, New York:Grune & Stratton, 101-120 (1982).

Sitar et al., "The use of non-physiological conditions to isolate fetal cells from maternal blood," *Exp Cell Res* 302:153-161 (2005).

Snider, "Birth Defects Detected with Simple Blood Test," USA Today. Oct. 9, 1991.

Sohda et al., "The Proportion of Fetal Nucleated Red Blood Cells in Maternal Blood: Estimation by FACS Analysis," *Prenatal Diagnosis* 17:743-752 (1997).

Stipp, "IG Labs Licenses New Technology for Fetal Testing," The Wall Street Journal. Aug. 10, 1990:B5.

Takayama et al., "Patterning Cells and Their Environments Using Multiple Laminar Fluid Flows in Capillary Networks," *PNAS* 5545-5548 (1999).

Takayama et al., "Subcellular Position of Small Molecues," *Nature*. 411:1016 (2001).

Takayasu et al., "Continuous Magnetic Separation of Blood Components from Whole Blood," IEEE Trans. On Applied Superconductivity. 10:927-930 (2000).

Tepperberg et al. "Prenatal diagnosis using interphase fluorescence in situ hybridization (FISH): 2-year multi-center retospective study and review of the literature" Prenatal Diagnosis 2001 21:293-301.

Theophilus et al., "Gaucher Disease: Molecular Heterogeneity and Phenotype-Genotype Correlations," *Am J Hum Genet* 45:212-225 (1989).

Thomas et al., "Specific Binding and Release of Cells from Beads Using Cleavable Tetrameric Antibody Complexes," *J Immunol Methods* 120:221-231 (1989).

Tibbe et al., "Statistical considerations for enumeration of circulating tumor cells," Cytometry 71(3):154-62 (2007).

Toner et al., "Blood-on-a-Chip," *Annual Review of Biomedical Engineering*. 7:77-103 (2005).

Tong et al., "Low Temperature Wafer Direct Bonding," *J. Microelectromech. Syst*. 3:29-35 (1994).

Trask et al., "Detection of DNA Sequences in Nuclei in Suspension by in Situ Hybridization and Dual Beam Flow Cytometry," *Science* 230:1401-1403 (1985).

Trowbridge et al.. "Human Cell Surface Glycoprotein Related to Cell Proliferation Is the Receptor for Transferrin," *PNAS* 78:3039-3043 (1981).

Turner et al., "Confinement-Induced Entropic Recoil of Single DNA Molecules in a Nanofluidic Structure," *Phys Rev Lett* 88:128103 (2002).

UPI, "Researchers find safer prenatal tests," The Boston Herald. Nov. 14, 1989:25.

Vandelli et al., "Development of a MEMS Microvalve Array for Fluid Flow Control," J Microelectromech Sys 7:395-403 (1998).

Voldman et al., "Holding Forces of Single-Particle Dielectrophoretic Traps," *Biophys. J*. 80:531-541 (2001).

Volkmuth et al., "Observation of Electrophoresis of Single DNA Molecules in Nanofabricated Arrays," Presentation at joint annual meeting of Biophysical Society and the American Society for Biochemistry and Molecular Biology. Feb. 9-13, 1992.

Volkmuth et al., "DNA Electrophoresis in Microlithographic Arrays," *Nature* 358:600-602 (1992).

Vona et al., "Enrichment, immunomorphological, and genetic characterization of fetal cells circulating in maternal blood," *Am J Pathol* 160(1):51-58 (2002).

Vona et al., "Isolation by size of epithelial tumor cells" *Amer J Pathol* 156:57 (2000).

Wachtel et al., "Fetal Cells in the Maternal Circulation: Isolation by Multiparameter Flow Cytometry and Confirmation by Polymerase Chain Reaction," *Hum. Reprod*. 6:1466-1469 (1991).

Walknowska et al., "Practical and Theoretical Implications of Fetal/Maternal Lymphocyte Transfer," *Lancet* 1:1119-1122 (1969).

Washizu et al., "Handling Biological Cells Utilizing a Fluid Integrated Circuit," IEEE Transactions of Industry Applications. 1990; 26: 352-8.

Washizu et al., "Handling Biological Cells Utilizing a Fluid Integrated Circuit," Industry Applications Society Annual Meeting Presentations. Oct. 2-7, 1988: 1735-40.

Weigl et al., "Microfluidic Diffusion-Based Separation and Detection," *Science* pp. 346-347 (1999).

Williams et al., "Prenatal Diagnosis of 46, XX Males: Confirmation of X-Y Interchange by Fluorescence in Situ Hybridization (FISH)," *Am J Hum Genet* Supplement to 51(4):A266 (1048) (1992).

Williams et al., "Comparison of Cell Separation Methods to Enrich the Proportion of Fetal Cells in Material Blood Samples," *Am J Hum Genet* Supplement to 51(4): A266 (1049) (1992).

Xu et al., "Dielectrophoresis of Human Red Cells in Microchips," *Electrophoresis* 20:1829-1831 (1999).

Yuan et al. "The Pumping Effect of Growing and Collapsing Bubbles in a Tube," *J Micromech Microeng* 9:402-413 (1999).

Zborowski et al., "Red Blood Cell Magnetophoresis," *Biophysical J* 84:2638-2645 (2003).

Zhang et al., "High-Speed Free-Flow Electrophoresis on Chip," *Anal Chem* 75:5759-5766 (2003).

Zhen et al., "Poly-FISH: a technique of repeated hybridzations that improves cytogenic analysis of fetal cells in maternal blood," *Prenat Diagn.* 18(11):1181-5 (1998).

Zheng et al., "Fetal cell identifiers: results of microscope slide-based immunocytochemical studies as a function of gestational age and abnormality," *Am J Obstet Gynecol* 180(5):1234-9 (1999).

Zuska, "Microtechnology Opens Doors to the Universe of Small Space," MD&DI Jan. (1997).

Final Office Action for U.S. Appl. No. 11/800,940 mailed Mar. 18, 2011 (10 pages).

U.S. Appl. No. 60/949,227, filed Jul. 11, 2007, Kapur.

Adinolfi, et al. Rapid detection of aneuploidies by microsatellite and the quantitative fluorescent polymerase chain reaction. Prenat. Diagn. 1997; 17(13):1299-311.

Ahn, et al. A fully integrated micromachined magnetic particle separator. Journal of Microelectromechanical Systems. 1996; 5(3):151-158.

Andre, et al. (2001). "Wedgelike Glycodendrimers as Inhibitors of Binding of Mammalian Galectins to Glycoproteins, Lactose Maxiclusters, and Cell Surface Glycoconjugates" Chembiochem : A European Journal of Chemical Biology vol. 2 pp. 822-830.

Ben-Yoseph, et al. Diagnosis and Carrier Detection of Farber Disease (Ceramidase Deficiency) in Plasma and Leukocytes. Pediatric Research. Apr. 1989: 139A-817.

Birner, et al. Evaluation of the United States Food and Drug Administration-approved scoring and test system of HER-2 protein expression in breast cancer. Clin Cancer Res. Jun. 2001;7(6):1669-75.

Blake, et al. Assessment of multiplex fluorescent PCR for screening single cells for trisomy 21 and single gene defects. Mol. Hum. Reprod. 1999; 5(12):1166-75.

Blankenstein, G., et al. Modular Concept of a Laboratory on a Chip for Chemical and Bichemical Analysis. Biosensors and Bioelectronics. 1998;13(3-4):427-438.

Bodurtha, et al. Genetic Analysis of Fat Deposition in 11-Year Old Twins. Pediatric Research. Apr. 1989: 139A-819.

Boehm, et al. Analysis of Defective Dystrophin Genes with cDNA Probes: Rearrangement Polymorphism, Detection of Deletions in Carrier Females, and Lower Than Expected Frequency of Carrier Mothers in Isolated Cases of Delections. Pediatric Research. Apr. 1989: 139A-820.

De Alba, et al. Prenatal diagnosis on fetal cells obtained from maternal peripheral blood: report of 66 cases. Prenat Diagn. Oct. 1999;19(10):934-40.

Duff, et al. (1998). "Intrabody Tissue-Specific Delivery of Antisense Conjugates in Animals: Ligand-Linker-Antisense Oligomer Conjugates", Methods in Enzymology, Academic Press Inc, San Diego, CA, US vol. 313, No. A pp. 297-321.

European office action dated Sep. 20, 2010 for Application No. 06749394.

European search report dated Oct. 5, 2009 for Application No. 06749394.

European SR dated Mar. 17, 2006 for Application No. 03798803.7.

European SR dated Aug. 2, 2006 for Application No. 03798803.7.

Examination report dated Jul. 11, 2011 for corresponding application EP 10185652.4.

Findlay, et al. Using MF-PCR to diagnose multiple defects from single cells: implications for PGD. Mol Cell Endocrinol. 2001; 183 Suppl 1:S5-12.

Galbraith, et al. Imaging cytometry by multiparameter fluorescence. Cytometry. 1991;12(7):579-96.

Hahn, et al. Current applications of single-cell PCR. Cell. Mol. Life Sci. 2000; 57(1):96-105. Review.

Hamsberger, et al. Imaging tumors of the central nervous system and extracranial head and neck. CA Cancer J Clin. Jul.-Aug. 1987;37(4):225-38.

Huang, et al. Possible association of beta2- and beta3-adrenergic receptor gene polymorphisms with susceptibility to breast cancer. Breast Cancer Res. 2001;3(4):264-9.

International preliminary examination report dated Sep. 17, 2004 for PCT Application No. US03/30965.

International search report and written opinion dated Sep. 10, 2008 for PCT Application No. US06-12778.

International search report dated Oct. 14, 2008 for PCT Application No. US2008/060546.

International search report dated Mar. 25, 2004 for PCT Application No. US03/30965.

International Search Report for PCT/US2004/018373 dated Oct. 20, 2004.

Klein, et al. Comparative genomic hybridization, loss of heterozygosity, and DNA sequence analysis of single cells. Proc Natl Acad Sci U S A. 1999; 96(8):4494-9.

Kubuschok, et al. Disseminated tumor cells in lymph nodes as a determinant for survival in surgically resected non-small-cell lung cancer. J Clin Oncol. Jan. 1999;17(1):19-24.

Leyland-Jones, B. Trastuzumab: hopes and realities. Lancet Oncol. Mar. 2002;3(3):137-44.

Loken, et al. Flow Cytometric Analysis of Human Bone Marrow: I. Normal Erythroid Development. Blood. 1987;69:255-263.

Newcombe, R. G. Two-sided confidence intervals for the single proportion: comparison of seven methods. Statistics in Medicine. 1998; 17:857-872.

Office Action mailed Dec. 18, 2009 from U.S. Appl. No. 11/726,276.

Office Action mailed Jan. 14, 2010 from from U.S. Appl. No. 11/726,230.

PMA finals decisions, Sep. 1998. Available at www.fda.gov/cdrh/pma/pmasep98.html. Accessed Jan. 10, 2008.

Proteins and Biotechnology. Laboratory Adventures in the Biological Sciences. Week Three 2002. Northwestern University.

Ren, et al. Reduced lysyl oxidase messenger RNA levels in experimental and human prostate cancer. Cancer Res. Mar. 15, 1998;58(6):1285-90.

Samura, et al. Female fetal cells in maternal blood: use of DNA polymorphisms to prove origin. Hum. Genet. 2000;107(1):28-32.

Schaefer, et al. The Clinical Relevance of Nucleated Red Blood Cells counts. Sysmex Journal International. 2000; 10(2):59-63.

Seow, et al. (2002). "Expression of a Functional Asialoglycoprotein Receptor in Human Renal Proximal Tubular Epithelial Cells" Nephron 2002;91:431-438.

Sherlock, et al. Assessment of diagnostic quantitative fluorescent multiplex polymerase chain reaction assays performed on single cells. Ann. Hum. Genet. 1998; 62:9-23.

Slunga-Tallberg, et al. Maternal Origin of nucleated erythrocytes in peripheral venous blood of pregnant women. Hum Genet. 1995; 96:53-57.

Stoughton, et al. Data-adaptive algorithms for calling alleles in repeat polymorphisms. Electrophoresis. 1997;18(1):1-5.

Troeger, et al. Approximately half of the erythroblasts in maternal blood are of fetal origin. Mol Hum Reprod. 1999; 5(12):1162-5.

Van Raamsdonk, et al. Optimizing the detection of nascent transcripts by RNA fluorescence in situ hybridization. Nucl. Acids. Res. 2001; 29(8):e42.

Voldborg, et al. Epidermal growth factor receptor (EGFR) and EGFR mutations, function and possible role in clinical trials. Ann Oncol. Dec. 1997;8(12):1197-206.

Voldman, et al. A microfabrication-based dynamic array cytometer. Anal. Chem. 2002; 74:3984-3990.

Washizu, M. Manipulation of Biological Objects in Micromachined Structures. Proceeding of the Workshop on Micro Electro Mechanical Systems, Travemunde, Feb. 4-7, 1992, no. workshop 5, Feb. 4, 1992, Benecke W.; Petzold H.C., pp. 196-201.

Wirtschafter, et al. Micrometastatic tumor detection in patients with head and neck cancer: a preliminary report. Arch Otolaryngol Head Neck Surg. Jan. 2002;128(1):40-43.

Written Opinion of the International Searching Authority for PCT/US2004/018373 dated Oct. 20, 2004.

Yu, et al. Molecular basis of the adult I phenotype and the gene responsible for the expression of the human blood group I antigen. Blood. 2001; 98:3840-3845.

Zhau, et al. Biomarkers associated with prostate cancer progression. J Cell Biochem Suppl. 1994;19:208-16.

\* cited by examiner

One embodiment of dilution/reaction chambers

Adhesion is included

Adhesion is included

------- Square array     ——— Triangular array

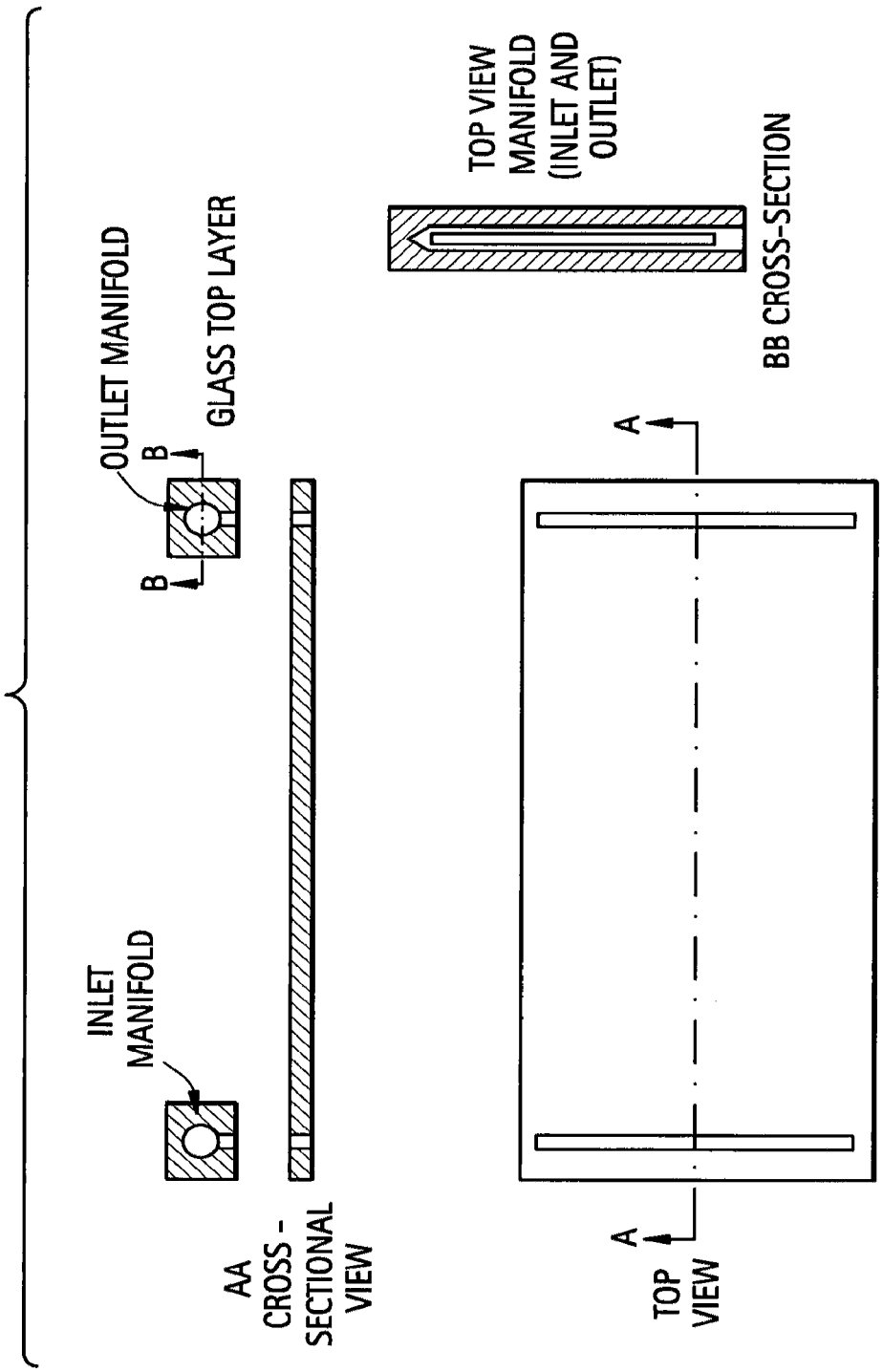

MICROFLUIDIC DEVICE FOR CELL SEPARATION AND USES THEREOF

CROSS-REFERENCE TO RELATED APPLICATIONS

This application is a divisional of U.S. application Ser. No. 10/529,453, having a §371 date of Dec. 19, 2005, which is the National Stage of PCT/US03/30965, filed Sep. 29, 2003, which claims benefit of U.S. Provisional Application Nos. 60/414,065, 60/414,258, and 60/414,102, filed on Sep. 27, 2002, each of which is hereby incorporated by reference.

BACKGROUND OF THE INVENTION

The invention relates to the fields of medical diagnostics and microfluidics.

There are several approaches devised to separate a population of homogeneous cells from blood. These cell separation techniques may be grouped into two broad categories: (1) invasive methods based on the selection of cells fixed and stained using various cell-specific markers; and (2) noninvasive methods for the isolation of living cells using a biophysical parameter specific to a population of cells of interest.

Invasive techniques include fluorescence activated cell sorting (FACS), magnetic activated cell sorting (MACS), and immunomagnetic colloid sorting. FACS is usually a positive selection technique that uses a fluorescently labeled marker to bind to cells expressing a specific cell surface marker. FACS can also be used to permeabilize and stain cells for intracellular markers that can constitute the basis for sorting. It is fast, typically running at a rate of 1,000 to 1,500 Hz, and well established in laboratory medicine. High false positive rates are associated with FACS because of the low number of photons obtained during extremely short dwell times at high speeds. Complicated multiparameter classification approaches can be used to enhance the specificity of FACS, but multianalyte-based FACS may be impractical for routine clinical testing because of the high cost associated with it. The clinical application of FACS is further limited because it requires considerable operator expertise, is laborious, results in cell loss due to multiple manipulations, and the cost of the equipment is prohibitive.

MACS is used as a cell separation technique in which cells that express a specific surface marker are isolated from a mixture of cells using magnetic beads coated with an antibody against the surface marker. MACS has the advantage of being cheaper, easier, and faster to perform as compared with FACS. It suffers from cell loss due to multiple manipulations and handling. Moreover, magnetic beads often autofluoresce and are not easily separated from cells. As a result, many of the immunofluorescence techniques used to probe into cellular function and structure are not compatible with this approach.

A magnetic colloid system has been used in the isolation of cells from blood. This colloid system uses ferromagnetic nanoparticles that are coated with goat anti-mouse IgG that can be easily attached to cell surface antigen-specific monoclonal antibodies. Cells that are labeled with ferromagnetic nanoparticles align in a magnetic field along ferromagnetic Ni lines deposited by lithographic techniques on an optically transparent surface. This approach also requires multiple cell handling steps including mixing of cells with magnetic beads and separation on the surfaces. It is also not possible to sort out the individual cells from the sample for further analysis.

Noninvasive techniques include charge flow separation, which employs a horizontal crossflow fluid gradient opposing an electric field in order to separate cells based on their characteristic surface charge densities. Although this approach can separate cells purely on biophysical differences, it is not specific enough. There have been attempts to modify the device characteristics (e.g., separator screens, buffer counterflow conditions, etc.) to address this major shortcoming of the technique. None of these modifications of device characteristics has provided a practical solution given the expected individual variability in different samples.

Since the prior art methods suffer from high cost, low yield, and lack of specificity, there is a need for a method for depleting a particular type of cell from a mixture that overcomes these limitations.

SUMMARY OF THE INVENTION

The invention features methods for separating cells from a sample (e.g., separating fetal red blood cells from maternal blood). The method begins with the introduction of a sample including cells into one or more microfluidic channels. In one embodiment, the device includes at least two processing steps. For example, a mixture of cells is introduced into a microfluidic channel that selectively allows the passage of a desired type of cell, and the population of cells enriched in the desired type is then introduced into a second microfluidic channel that allows the passage of the desired cell to produce a population of cells further enriched in the desired type. The selection of cells is based on a property of the cells in the mixture, for example, size, shape, deformability, surface characteristics (e.g., cell surface receptors or antigens and membrane permeability), or intracellular properties (e.g., expression of a particular enzyme).

In practice, the method may then proceed through a variety of processing steps employing various devices. In one step, the sample is combined with a solution in the microfluidic channels that preferentially lyses one type of cell compared to another type. In another step, cells are contacted with a device containing obstacles in a microfluidic channel. The obstacles preferentially bind one type of cell compared to another type. Alternatively, cells are arrayed individually for identification of the cells of interest. Cells may also be subjected to size, deformability, or shape based separations. Methods of the invention may employ only one of the above steps or any combination of the steps, in any order, to separate cells. The methods of the invention desirably recover at least 75%, 80%, 90%, 95%, 98%, or 99% of the desired cells in the sample.

The invention further features a microfluidic system for the separation of a desired cell from a sample. This system may include devices for carrying out one or any combination of the steps of the above-described methods. One of these devices is a lysis device that includes at least two input channels; a reaction chamber (e.g., a serpentine channel); and an outlet channel. The device may additional include another input and a dilution chamber (e.g., a serpentine channel). The lysis device is arranged such that at least two input channels are connected to the outlet through the reaction chamber. When a dilution chamber is present, it is disposed between the reaction chamber and the outlet, and another inlet is disposed between the reaction and dilution chambers. The system may also include a cell depletion device that contains obstacles that preferentially bind one type of cell when compared to another type, e.g., they are coated with anti-CD45, anti-CD36, anti-GPA, or anti-CD71 antibodies. The system may also include an arraying device that contains a two-dimensional array of locations for the containment of individual cells. The arraying device may also contain actuators for the selective manipulation (e.g., release) of individual cells in the array. Finally, the system may include a device for size based separation of cells. This device includes sieves that only allow passage of cells below a desired size. The sieves are located with a microfluidic channel through which a suspension of cells passes, as described herein. When used in combination, the devices in the system may be in liquid communication with one another. Alternatively, samples that pass through a device may be collected and transferred to another device.

By "a depleted cell population" is meant a population of cells that has been processed to decrease the relative population of a specified cell type in a mixture of cells. Subsequently collecting those cells depleted from the mixture also leads to a sample enriched in the cells depleted.

By an "enriched cell population" is meant a population of cells that has been processed to increase the relative population of a specified cell type in a mixture of cells.

By "lysis buffer" is meant a buffer that, when contacted with a population of cells, will cause at least one type of cell to lyse.

By "to cause lysis" is meant to lyse at least 90% of cells of a particular type.

By "not lysed" is meant less than 10% of cells of a particular type are lysed. Desirably, less that 5%, 2%, or 1% of these cells are lysed.

By "type" of cell is meant a population of cells having a common property, e.g., the presence of a particular surface antigen. A single cell may belong to several different types of cells.

By "serpentine channel" is meant a channel that has a total length that is greater than the linear distance between the end points of the channel. A serpentine channel may be oriented entirely vertically or horizontally. Alternatively, a serpentine channel may be "3D," e.g., portions of the channel are oriented vertically and portions are oriented horizontally.

By "microfluidic" is meant having one or more dimensions of less than 1 mm.

By "binding moiety" is meant a chemical species to which a cell binds. A binding moiety may be a compound coupled to a surface or the material making up the surface. Exemplary binding moieties include antibodies, oligo- or polypeptides, nucleic acids, other proteins, synthetic polymers, and carbohydrates.

By "obstacle" is meant an impediment to flow in a channel, e.g., a protrusion from one surface.

By "specifically binding" a type of cell is meant binding cells of that type by a specified mechanism, e.g., antibody-antigen interaction. The strength of the bond is generally enough to prevent detachment by the flow of fluid present when cells are bound, although individual cells may occasionally detach under normal operating conditions.

By "rows of obstacles" is meant is meant a series of obstacles arranged such that the centers of the obstacles are arranged substantially linearly. The distance between rows is the distance between the lines of two adjacent rows on which the centers are located.

By "columns of obstacles" is meant a series of obstacles arranged perpendicular to a row such that the centers of the obstacles are arranged substantially linearly. The distance between columns is the distance between the lines of two adjacent columns on which the centers are located.

The methods of the invention are able to separate specific populations of cells from a complex mixture without fixing and/or staining. As a result of obtaining living homogeneous population of cells, one can perform many functional assays on the cells. The microfluidic devices described herein provide a simple, selective approach for processing of cells.

Other features and advantages of the invention will be apparent from the following description and the claims.

BRIEF DESCRIPTION OF THE DRAWINGS

FIG. 17 is an illustration of various views of the inlet and outlets of a cell binding device.

Figures are not necessarily to scale.

DETAILED DESCRIPTION OF THE INVENTION

The invention features methods for separating a desired cell from a mixture or enriching the population of a desired cell in a mixture. The methods are generally based on sequential processing steps, each of which reduces the number of undesired cells in the mixture, but one processing step may be used in the methods of the invention. Devices for carrying out various processing steps may be separate or integrated into one microfluidic system. The devices of the invention are a device for cell lysis, a device for cell binding, a device for arraying cells, and a device for size, shape, or deformability based separation. In one embodiment, processing steps are used to reduce the number of cells prior to arraying. Desirably, the methods of the invention retain at least 75%, 80%, 90%, 95%, 98%, or 99% of the desired cells compared to the initial mixture, while potentially enriching the population of desired cells by a factor of at least 100, 1000, 10,000, 100,000, or even 1,000,000 relative to one or more non-desired cell types. The methods of the invention may be used to separate or enrich cells circulating in the blood (Table 1).

TABLE 1

Types, concentrations, and sizes of blood cells.

| Cell Type | Concentration (cells/µl) | Size (µm) |
|---|---|---|
| Red blood cells (RBC) | 4.2-6.1 $10^6$ | 4-6 |
| Segmented Neutrophils (WBC) | 3600 | >10 |
| Band Neutrophils (WBC) | 120 | >10 |
| Lymphocytes (WBC) | 1500 | >10 |
| Monocytes (WBC) | 480 | >10 |
| Eosinophils (WBC) | 180 | >10 |
| Basophils (WBC) | 120 | >10 |
| Platelets | 500 $10^3$ | 1-2 |
| Fetal Nucleated Red Blood Cells | 2-50 $10^{-3}$ | 8-12 |

Devices
A. Cell Lysis

One device of the invention is employed to lysis of a population of cells selectively, e.g., maternal red blood cells, in a mixture of cells, e.g., maternal blood. This device allows for the processing of large numbers of cells under nearly identical conditions. The lysis device desirably removes a large number of cells prior to further processing. The debris, e.g., cell membranes and proteins, may be trapped, e.g., by filtration or precipitation, prior to any further processing.

Figure 1:
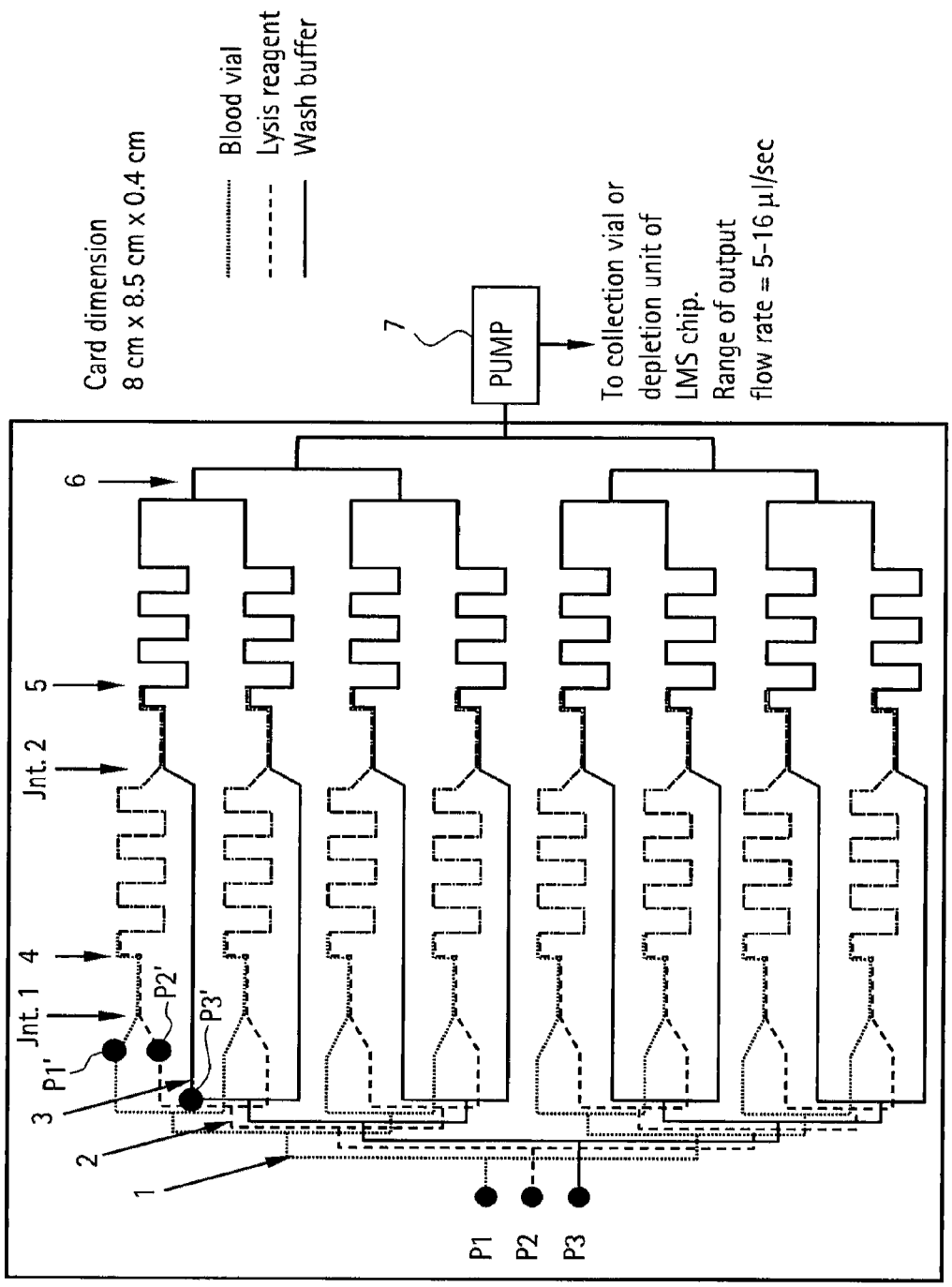
FIG. 1 is a schematic layout of a microfluidic device that enables selective lysis of cells.
Figure 2:
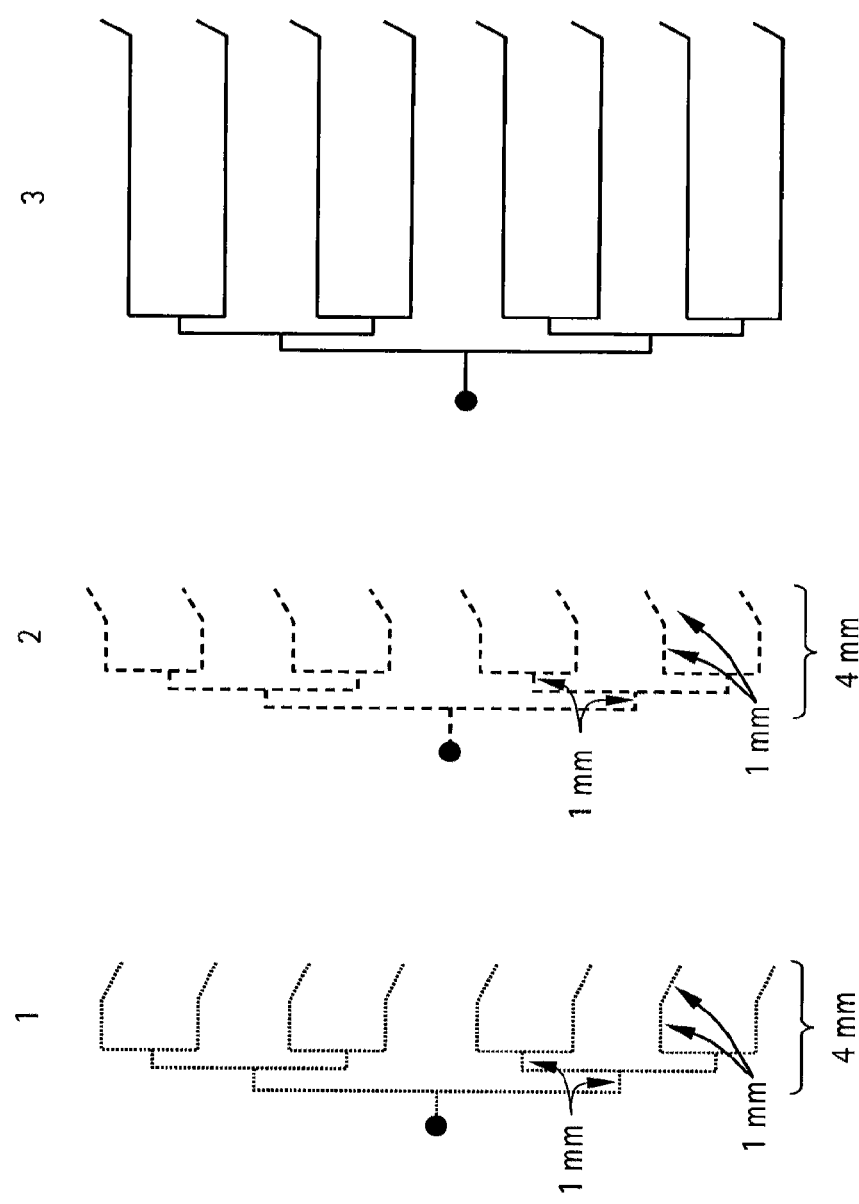
FIG. 2 is an illustration of the channel layout for the introduction of three fluids to the device, e.g., blood sample, lysis buffer, and diluent.
Figure 3:
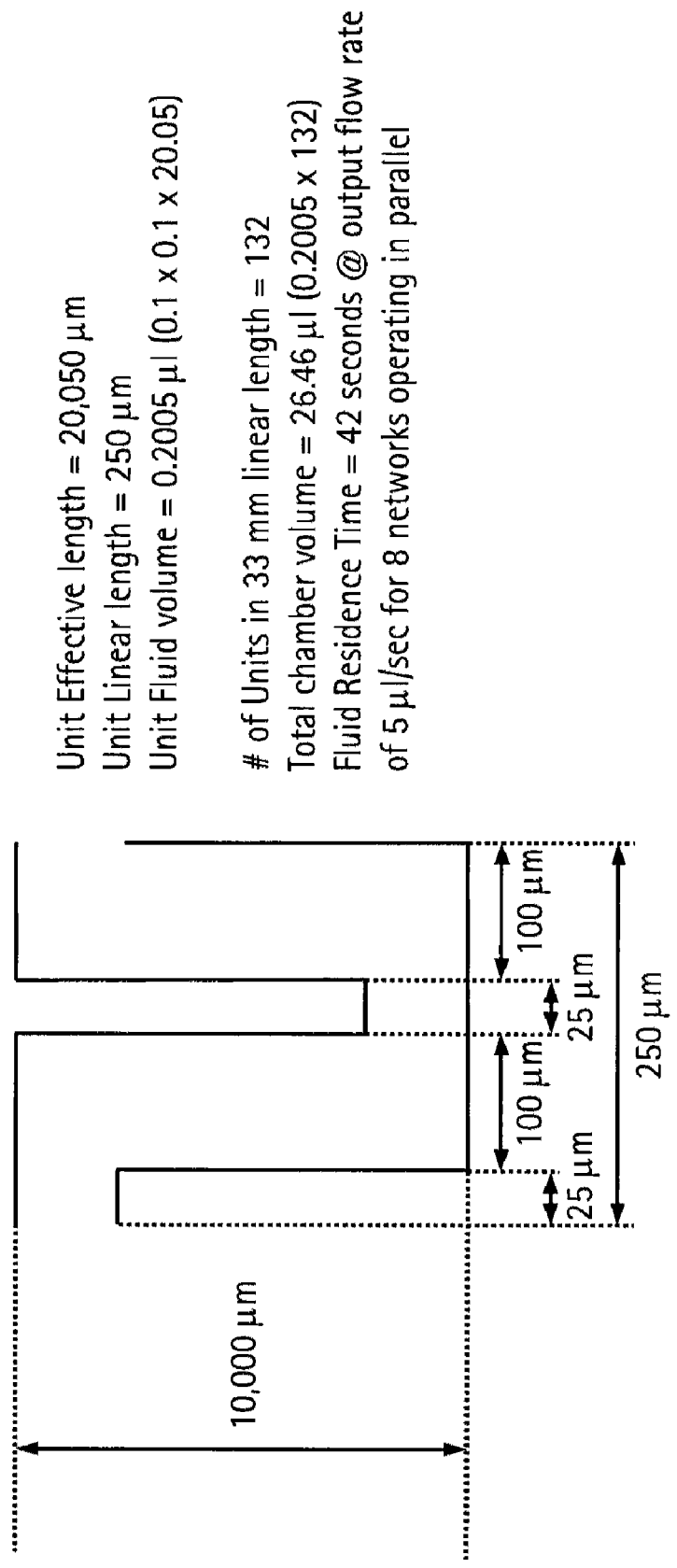
FIG. 3 is an illustration of a repeating unit of the reaction chamber of the device where a sample of cells is passively mixed with a lysis buffer. In one example, 133 units are connected to form the reaction chamber.
Figure 4:
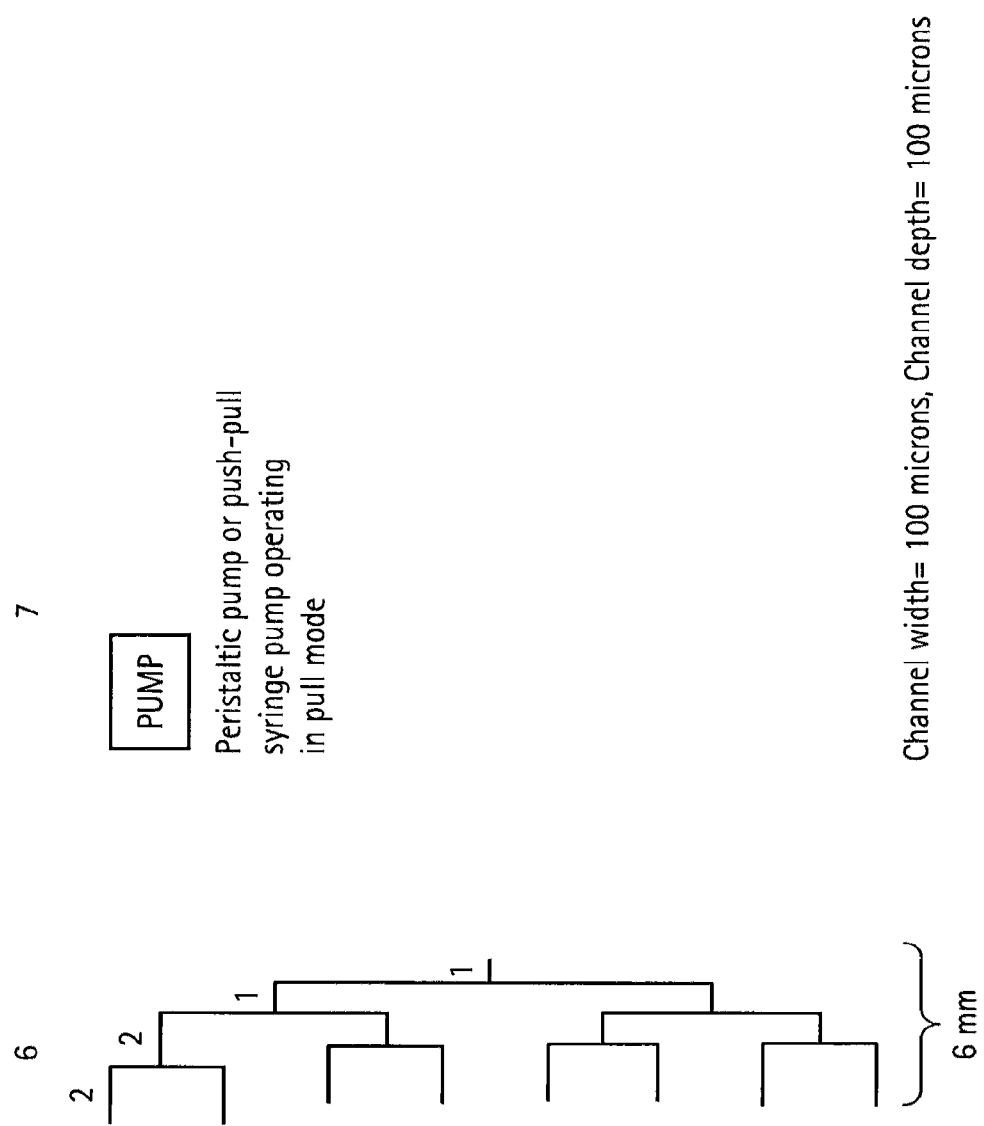
FIG. 4 is an illustration of the outlet channels of the device.

Device. A design for a lysis device of the invention is shown in FIG. 1. The overall branched architecture of the channels in the device permits equivalent pressure drops across each of the parallel processing networks. The device can be functionally separated into four distinct sections: 1) distributed input channels carrying fluids, e.g., blood, lysis reagent, and wash buffer, to junctions 1 and 2 (FIG. 2); 2) a serpentine reaction chamber for the cell lysis reaction residing between the two junctions (FIG. 3); 3) a dilution chamber downstream of Junction 2 for dilution of the lysis reagent (FIG. 3); and 4) distributed output channels carrying the lysed sample to a collection vial or to another microfluidic device (FIG. 4).

Input/Output Channels. The branched input and output networks of channels enable even distribution of the reagents into each of the channels (8, as depicted in FIG. 1). The three ports for interfacing the macro world with the device typically range in diameter from 1 mm-10 mm, e.g., 2, 5, 6, or 8 mm. Air tight seals may be formed with ports 1, 2, and 3, e.g., through an external manifold integrated with the device (FIG. 1). The three solution vials, e.g., blood, lysing reagent, and diluent, may interface with such a manifold. The input channels from ports 1, 2, and 3 to the reaction and mixing chambers, for the three solutions shown in FIG. 1, may be separated either in the z-plane of the device (three layers, each with one set of distribution channels, see FIG. 2) or reside in the external manifold. If residing in the external manifold, the distribution channels are, for example, CNC (computer numerically controlled) machined in stainless steel and may have dimensions of 500 µm diameter. The manifold may hermetically interface with the device at ports that are etched into locations 1', 2', and 3' shown in FIG. 1. Locating the distribution channels in a manifold reduces the complexity and cost of the device. Retaining the distribution channels on the device will allow greater flexibility in selecting smaller channel size, while avoiding any issues of carry-over contamination between samples. Each sample input channel may have a separate output, or as depicted in FIG. 4, the output channels for each sample input are combined. As an alternative to a manifold, tubing for each fluid input or output may be attached to the device, e.g., by compression fitting to gaskets or nipples or use of watertight connections such as a luer lock. The channels on the device transporting the fluids to the mixing junctions and chambers beyond, can range from 10 µm-500 µm in width and depth, e.g., at most 10 µm, 25 µm, 50 µm, 75 µm, 100 µm, 150 µm, 200 µm, 250 µm, 350 µm, or 450 µm width and depth. The channel architecture is desirably rectangular but may also be circular, semi-circular, V-shaped, or any other appropriate shape. In one embodiment, the output channel (or channels) has a cross-sectional area equal to the sum of the cross-sectional areas of the input channels.

Reaction and Dilution Chambers. For lysis and dilution, two fluid streams are combined and allowed to pass through the chambers. Chambers may be linear or serpentine channels. In the device depicted in FIG. 1, the sample and lysis buffer are combined at junction 1, and the lysed sample and the diluent are combined at junction 2. Serpentine architecture of the reaction chamber and dilution chamber enables sufficient resident time of the two reacting solutions for proper mixing by diffusion or other passive mechanisms, while preserving a reasonable overall footprint for the device (FIG. 3). The serpentine channels may be constructed in 2D or in 3D, e.g., to reduce the total length of the device or to introduce chaotic advection for enhanced mixing. For short residence times, a linear chamber may be desired. Exemplary resident times include at least 1 second, 5 seconds, 10 seconds, 30 seconds, 60 second, 90 seconds, 2 minutes, 5 minutes, 30 minutes, 1 hour, or greater that 1 hour. The flow rate of fluids in the reaction/dilution chambers can be accurately controlled by controlling the width, depth, and effective length of the channels to enable sufficient mixing of the two reagents while enabling optimal processing throughput. In one embodiment, the serpentine mixing chambers for cell lysis (reaction chamber) and for dilution of the lysed sample (dilution chamber) have a fluid volume each of ~26 µl. Other examples of reaction/dilution chamber volumes range from 10-200 µl, e.g., at most 20, 50, 100, or 150 µl. In some embodiments, the width and depth of the reaction and dilution chambers have the same range as the input and output channels, i.e., 10 to 500 µm. Alternatively, the chambers may have a cross-sectional area equal to the combined areas of any input (or output channels) in order to ensure a uniform velocity of flow through the device. In one example, the chambers are 100 µm 100 µm channels. The total length of the chambers may be at least 1 cm, 5 cm, 10 cm, 20 cm, 30 cm, 40 cm, or 50 cm.

For lysis of maternal RBCs, device output flow rates may range from processing 5-16 µl of blood per second resulting in a 20-60 minute processing time for 20 ml sample, or 10-30 min processing time for 10 ml sample. It is expected that the sample volume required for capturing sufficient number of fetal cells will be lower than 10 ml because of the efficiency of the process. As such, it is expected that the device throughput per sample will be less than 10 minutes. A residence time of >30 seconds from the time of convergence of the two solutions, maternal blood and lysis reagent, within the passive mixer is deemed sufficient to obtain effective hemolysis (T. Maren, Mol. Pharmacol. 1970, 6:430). Alternatively, the concentration of the lysis reagent can be adjusted to compensate for residence time in the reaction chamber. The flow rates and residence times for other cell types may be determined by theory or experimentation. In one embodiment, the flow rates in each channel are limited to <20 µl/sec to ensure that wall shear stress on cells is less than 1 dyne/cm$^2$ (cells are known to be affected functionally by shear stress >1 dyne/cm$^2$ though deleterious effects are not seen in most cells until after 10 dynes/cm$^2$). In one embodiment, the flow rate in each channel is at most 1, 2, 5, 10, 15 µl/sec. Referring to FIG. 1, the effective length of the diluent input channel leading to junction 2 may be shorter than the effective length of the reaction chamber. This feature enables the diluent to flow into and prime the channels downstream of junction 2, prior to arrival of the lysed sample at junction 2. The overflow buffer pre-collected in the output vial may act as a secondary diluent of the lysed sample when collected, e.g., for further processing or analysis. Additionally, the diluent primes the channels downstream of junction 2 to enable smoother flow and merging of the lysed sample with the buffer in the diluting chamber, and this priming eliminates any deleterious surface tension effects from dry channels on the lysed sample. The diameter of the channels carrying the diluent may be adjusted to enable the diluent to reach junction 2 at the same time as the lysed blood to prevent any problems associated with air forced from the reaction chamber as the sample and lysis buffers are introduced.

Figure 5:
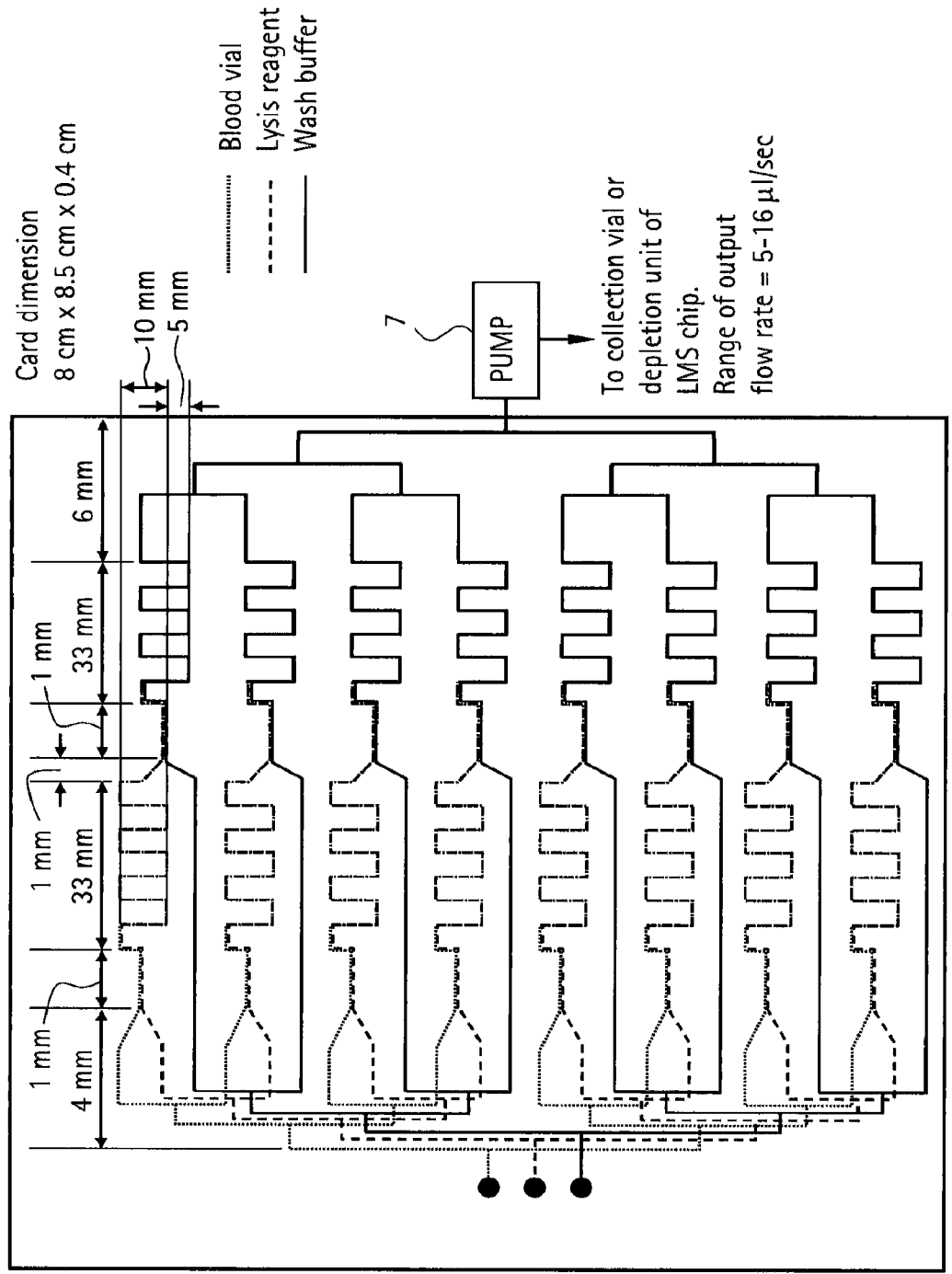
FIG. 5 is an illustration of a device for cell lysis.

Although the above description focuses on a device with eight parallel processing channels, any number of channels, e.g., 1, 2, 4, 16, or 32, may be employed depending on the size of the device. The device is described in terms of combining two fluids for lysis and dilution, but three or more fluids may be combined for lysis or dilution. The combination may be at one junction or a series of junctions, e.g., to control the timing of the sequential addition of reactants. Additional fluid inputs may be added, e.g., to functionalize the remaining cells, alter the pH, or cause undesirable components to precipitate. In addition, the exact geometry and dimensions of the channels may be altered (exemplary dimensions are shown in FIG. 5). Devices of the invention may be disposable or reusable. Disposable devices reduce the risk of contamination between samples. Reusable devices may be desirable in certain instances, and the device may be cleaned, e.g., with various detergents and enzymes, e.g., proteases or nucleases, to prevent contamination.

Pumping. In one embodiment, the device employs negative pressure pumping, e.g., using syringe pumps, peristaltic pumps, aspirators, or vacuum pumps. The negative pressure allows for processing of the complete volume of a clinical blood sample, without leaving unprocessed sample in the channels. Positive pressure, e.g., from a syringe pump, peristaltic pump, displacement pump, column of fluid, or other fluid pump, may also be used to pump samples through a device. The loss of sample due to dead volume issues related to positive pressure pumping may be overcome by chasing the residual sample with buffer. Pumps are typically interfaced to the device via hermetic seals, e.g., using silicone gaskets.

The flow rates of fluids in parallel channels in the device may be controlled in unison or separately. Variable and differential control of the flow rates in each of channels may be achieved, for example, by employing, a multi-channel individually controllable syringe manifold. In this embodiment, the input channel distribution will be modified to decouple all of the parallel networks. The output may collect the output from all channels via a single manifold connected to a suction (no requirements for an airtight seal) outputting to a collection vial or to another microfluidic device. Alternately, the output from each network can be collected separately for downstream processing. Separate inputs and outputs allow for parallel processing of multiple samples from one or more individuals.

Fabrication. A variety of techniques can be employed to fabricate a device of the invention, and the technique employed will be selected based in part on the material of choice. Exemplary materials for fabricating the devices of the invention include glass, silicon, steel, nickel, poly(methylmethacrylate) (PMMA), polycarbonate, polystyrene, polyethylene, polyolefins, silicones (e.g., poly(dimethylsiloxane)), and combinations thereof. Other materials are known in the art. Methods for fabricating channels in these materials are known in the art. These methods include, photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding is suitable. Conventional thermoplastic injection molding used for mass-fabrication of compact discs (which preserves fidelity of features in sub-microns) may also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) has the advantages of being compatible with high-molecular weight polymers, which are excellent for small structures, but is difficult to use in replicating high aspect ratio structures and has longer cycle times. Injection molding works well for high-aspect ratio structures but is most suitable for low molecular weight polymers.

A device may be fabricated in one or more pieces that are then assembled. In one embodiment, separate layers of the device contain channels for a single fluid, as in FIG. 1. Layers of a device may be bonded together by clamps, adhesives, heat, anodic bonding, or reactions between surface groups (e.g., wafer bonding). Alternatively, a device with channels in more than one plane may be fabricated as a single piece, e.g., using stereolithography or other three-dimensional fabrication techniques.

Figure 6A:
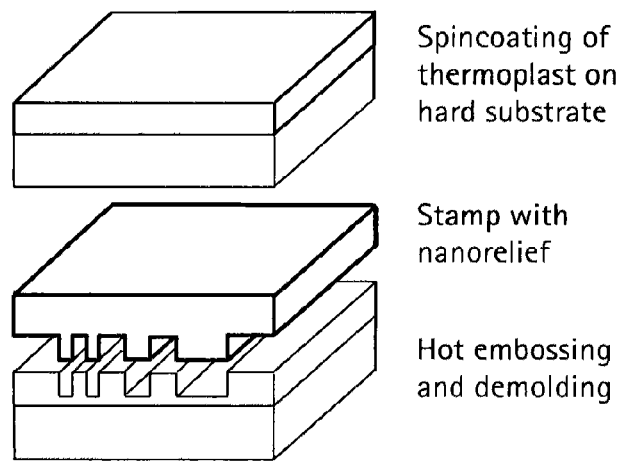
FIGS. 6A and 6B are illustrations of a method for the fabrication of a device of the invention.
Figure 6B:
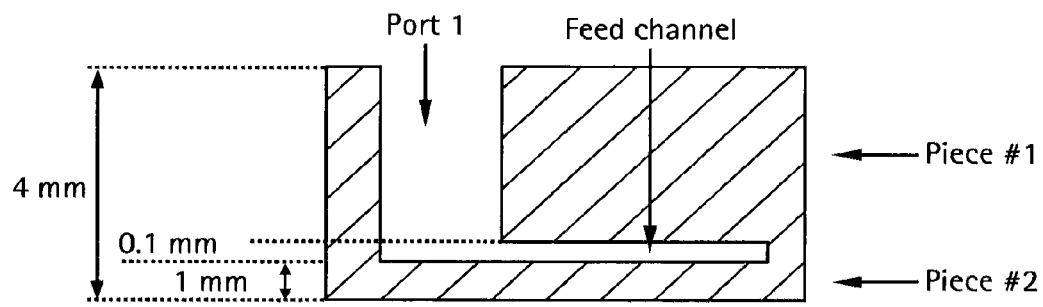

In one embodiment, the device is made of PMMA. The features, for example those shown in FIG. 1, are transferred onto an electroformed mold using standard photolithography followed by electroplating. The mold is used to hot emboss the features into the PMMA at a temperature near its glass transition temperature (105° C.) under pressure (5 to 20 tons) (pressure and temperature will be adjusted to account for high-fidelity replication of the deepest feature in the device) as shown schematically in FIG. 6A. The mold is then cooled to enable removal of the PMMA device. A second piece used to seal the device, composed of similar or dissimilar material, may be bonded onto the first piece using vacuum-assisted thermal bonding. The vacuum prevents formation of air-gaps in the bonding regions. FIG. 6B shows a cross-section of the two-piece device assembly at the junction of Port 1 (source for blood sample) and feed channel.

Chemical Derivitization. To reduce non-specific adsorption of cells or compounds released by lysed cells onto the channel walls, one or more channel walls may be chemically modified to be non-adherent or repulsive. The walls may be coated with a thin film coating (e.g., a monolayer) of commercial non-stick reagents, such as those used to form hydrogels. Additional examples chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls will depend on the nature of the species being repelled and the nature of the walls and the species being attached. Such surface modification techniques are well known in the art. The walls may be functionalized before or after the device is assembled.

The channel walls may also be coated in order to capture materials in the sample, e.g., membrane fragments or proteins.

Methods. In the present invention, a sample of cells, e.g., maternal blood, is introduced into one or more microfluidic channels. A lysis buffer containing reagents for the selective lysis for a population of cells in the sample is then mixed with the blood sample. Desirably, the mixing occurs by passive means, e.g., diffusion or chaotic advection, but active means may be employed. Additional passive and active mixers are known in the art. The lysis reaction is allowed to continue for a desired length of time. This length of time may be controlled, for example, by the length of the channels or by the rate of flow of the fluids. In addition, it is possible to control the volumes of solutions mixed in the channels by altering the relative volumetric flow rates of the solutions, e.g., by altering the channel size or velocity of flow. The flow may be slowed down, increased, or stopped for any desired period of time. After lysis has occurred, a diluent may be introduced into the channel in order to reduce the concentration of the lysis reagents and any potentially harmful species (e.g., endosomal enzymes) released by the lysed cells. The diluent may contain species that neutralize the lysis reagents or otherwise alter the fluid environment, e.g., pH or viscosity, or it may contain reagents for surface or intracellular labeling of cells. The diluent may also reduce the optical density of the solution, which may be important for certain detection schemes, e.g., absorbance measurements.

Exemplary cell types that may be lysed using the methods described herein include adult red blood cells, white blood cells (such as T cells, B cells, and helper T cells), infected white blood cells, tumor cells, and infectious organisms (e.g., bacteria, protozoa, and fungi). Lysis buffers for these cells may include cell specific IgM molecules and proteins in the complement cascade to initiate complement mediated lysis. Another kind of lysis buffer may include viruses that infect a specific cell type and cause lysis as a result of replication (see, e.g., Pawlik et al. Cancer 2002, 95:1171-81). Other lysis buffers are known in the art.

A device of the invention may be used for the selective lysis of maternal red blood cells (RBCs) in order to enrich a blood sample in fetal cells. In this example, a maternal blood sample, 10-20 ml, is processed within the first one to three hours after sample collection. If the processing is delayed beyond three hours, the sample may be stored at 4° C. until it is processed. The lysis device of the invention allows mixing of the lysis reagent ($NH_4Cl$ (0 to 150 mM)+$NaHCO_3$ (0.001 to 0.3 mM)+acetazolamide (0.1 to 100 µM)) with the maternal blood to enable selective lysis of the maternal red blood cells by the underlying principle of the Orskov-Jacobs-Stewart reaction (see, for example, Boyer et al. Blood 1976, 47:883-897). The high selective permeability of the carbonic anhydrase inhibitor, acetazolamide, into fetal cells enables selective hemolysis of the maternal red blood cells. Endogenous carbonic anhydrase in the maternal cells converts $HCO_3^-$ to carbon dioxide, which lyses the maternal red blood cells. The enzyme is inhibited in the fetal red blood cells, and those cells are not lysed. A diluent (e.g., phosphate buffered saline) may be added after a period of contact between the lysis reagents and the cell sample to reduce the risk that a portion of the fetal red bloods cells will be lysed after prolonged exposure to the reagents.

B. Cell Binding

Another device of the invention involves depletion of whole cells from a mixture by binding the cells to the surfaces of the device. The surfaces of such a device contain substances, e.g., antibodies or ligands for cell surface receptors, that bind a particular subpopulation of cells. This step in method may employ positive selection, i.e., the desired cells are bound to the device, or it may employ negative selection, i.e., the desired cells pass through the device. In either case, the population of cells containing the desired cells is collected for analysis or further processing.

Device. The device is a microfluidic flow system containing an array of obstacles of various shapes that are capable of binding a population of cells, e.g., those expressing a specific surface molecule, in a mixture. The bound cells may be directly analyzed on the device or be removed from the device, e.g., for further analysis or processing. Alternatively, cells not bound to the obstacles may be collected, e.g., for further processing or analysis.

Figure 7:
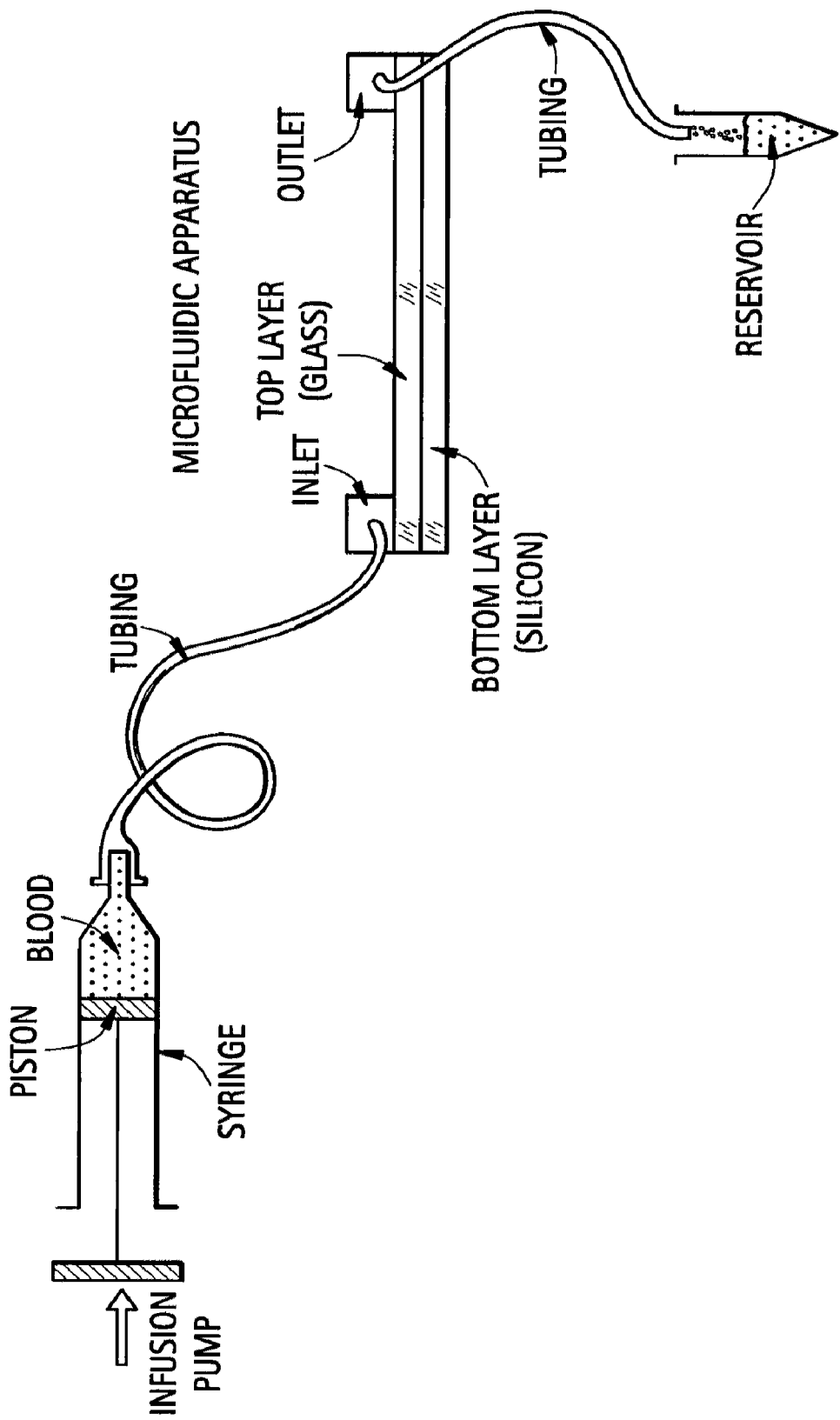
FIG. 7 is a schematic diagram of a cell binding device.
Figure 8:
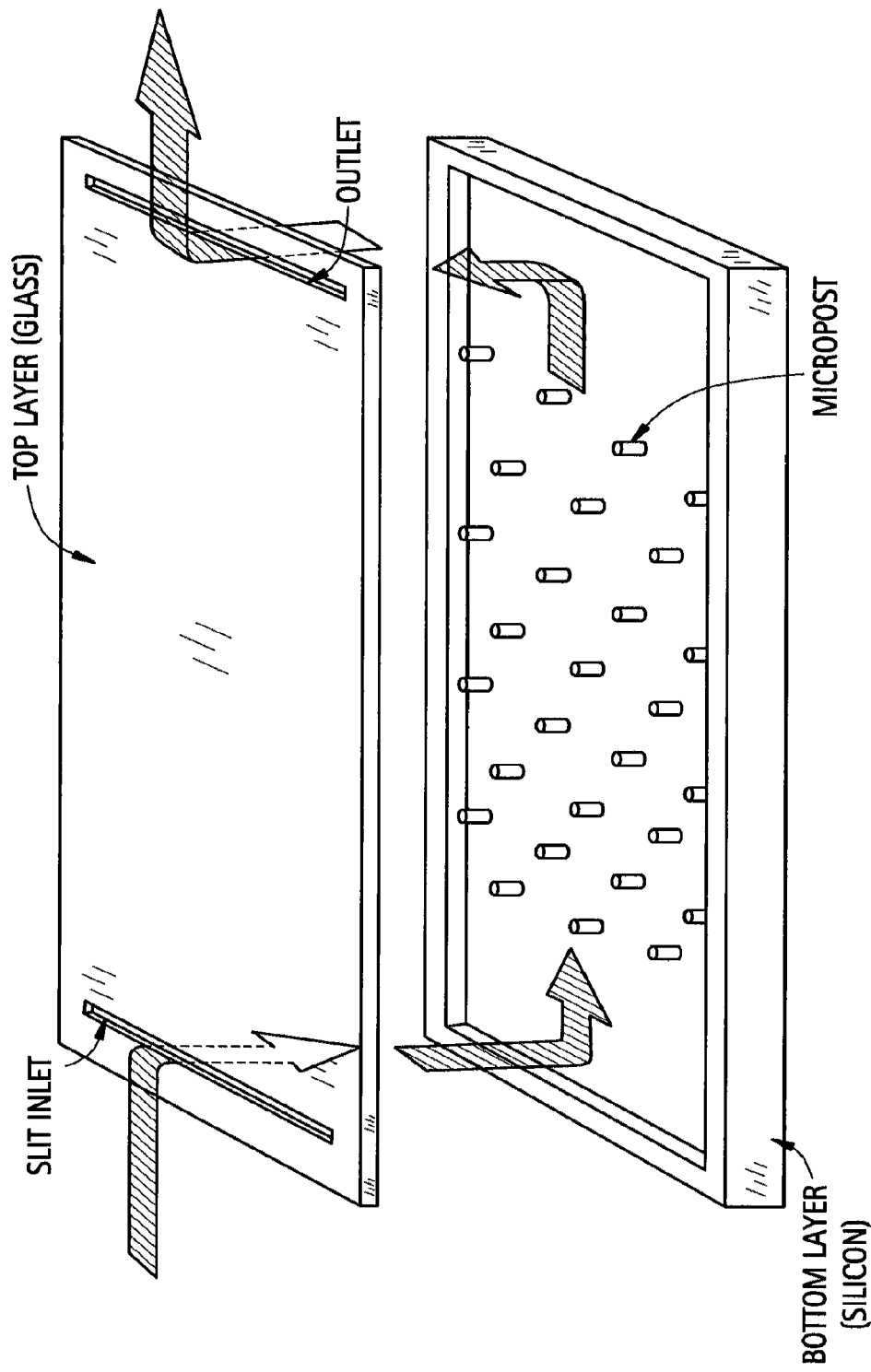
FIG. 8 is an exploded view of a cell binding device.

An exemplary device is a flow apparatus having a flat-plate channel through which cells flow; such a device is described in U.S. Pat. No. 5,837,115. FIG. 7 shows an exemplary system including an infusion pump to perfuse a mixture of cells, e.g., blood, through the microfluidic device. Other pumping methods, as described herein, may be employed. The device may be optically transparent, or have transparent windows, for visualization of cells during flow through the device. The device contains obstacles distributed, e.g., in an ordered array or randomly, throughout the flow chamber. The top and bottom surfaces of the device are desirably parallel to each other. This concept is depicted in FIG. 8. The obstacles may be either part of the bottom or the top surface and desirably define the height of the flow channel. It is also possible for a fraction of the obstacles to be positioned on the bottom surface, and the remainder on the top surface. The obstacles may contact both the top and bottom of the chamber, or there may be a gap between an obstacle and one surface. The obstacles may be coated with a binding moiety, e.g., an antibody, a charged polymer, a molecule that binds to a cell surface receptor, an oligo- or polypeptide, a viral or bacterial protein, a nucleic acid, or a carbohydrate, that binds a population of cells, e.g., those expressing a specific surface molecule, in a mixture. Other binding moieties that are specific for a particular type of cell are known in the art. In an alternative embodiment, the obstacles are fabricated from a material to which a specific type of cell binds. Examples of such materials include organic polymers (charged or uncharged) and carbohydrates. Once a binding moiety is coupled to the obstacles, a coating, as described herein, may also be applied to any exposed surface of the obstacles to prevent non-specific adhesion of cells to the obstacles.

Figure 9:
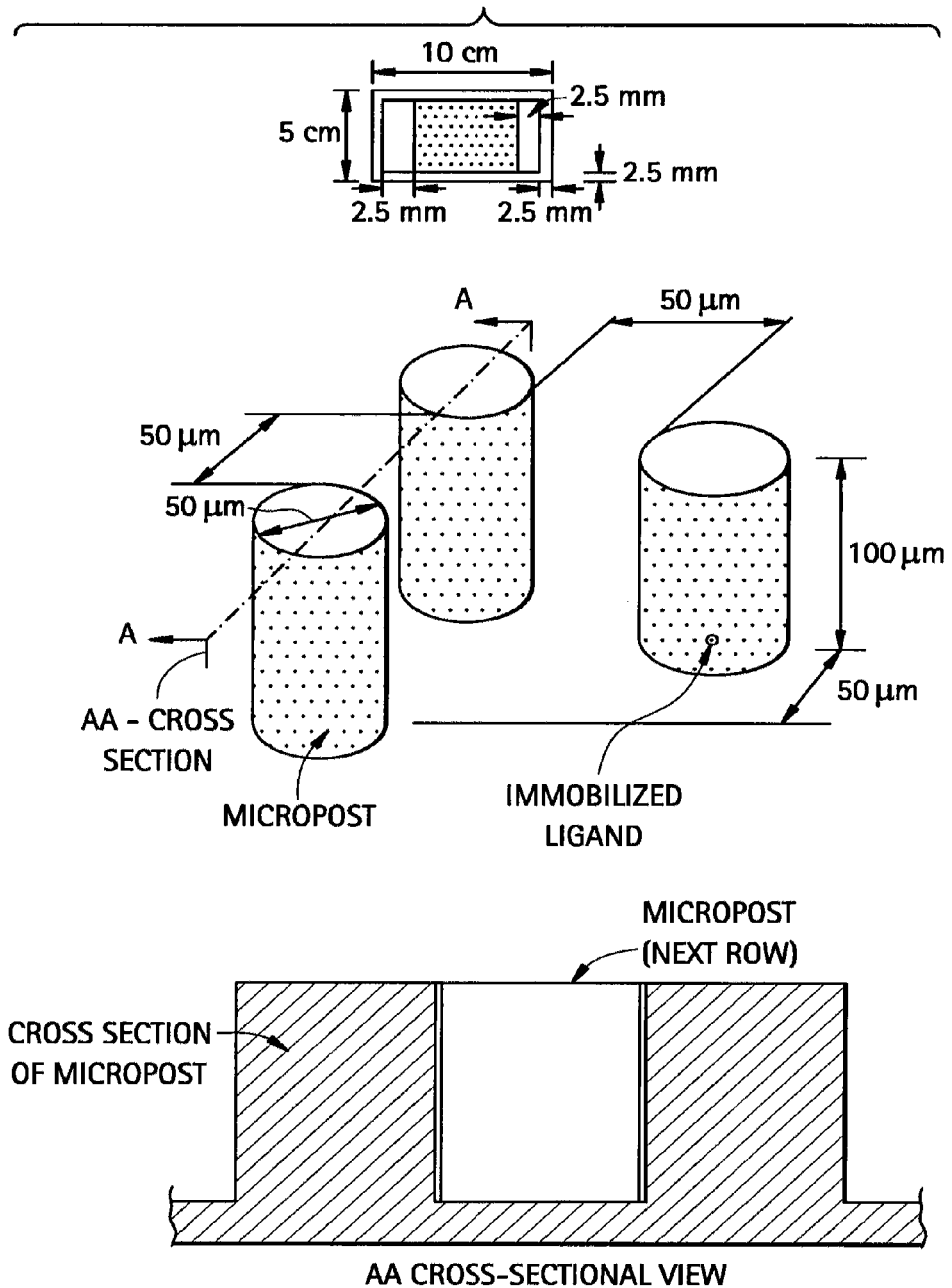
FIG. 9 is an illustration of obstacles in a cell binding device.

A geometry of obstacles is shown in FIG. 9. In one example, obstacles are etched on a surface area of 2 cm 7 cm on a substrate with overall dimensions of 2.5 cm 7.5 cm. A rim of 2 mm is left around the substrate for bonding to the top surface to create a closed chamber. In one embodiment, obstacle diameter is 50 µm with a height of 100 µm. Obstacles may be arranged in a two-dimensional array of rows with a 100 µm distance from center-to-center. This arrangement provides 50 µm openings for cells to flow between the obstacles without being mechanically squeezed or damaged. The obstacles in one row are desirably shifted, e.g., 50 µm with respect to the adjacent rows. This alternating pattern may be repeated throughout the design to ensure increased collision frequency between cells and obstacles. The diameter, width, or length of the obstacles may be at least 5, 10, 25, 50, 75, 100, or 250 µm and at most 500, 250, 100, 75, 50, 25, or 10 µm. The spacing between obstacles may be at least 10, 25, 50, 75, 100, 250, 500, or 750 µm and at most 1000, 750, 500, 250, 100, 75, 50, or 25 µm. Table 2 lists exemplary spacings based on the diameter of the obstacles.

TABLE 2

Exemplary spacings for obstacles.

| Obstacle diameter (µm) | Spacing between obstacles (µm) |
|---|---|
| 100 | 50 |
| 100 | 25 |
| 50 | 50 |
| 50 | 25 |
| 10 | 25 |
| 10 | 50 |
| 10 | 15 |

Figure 10:
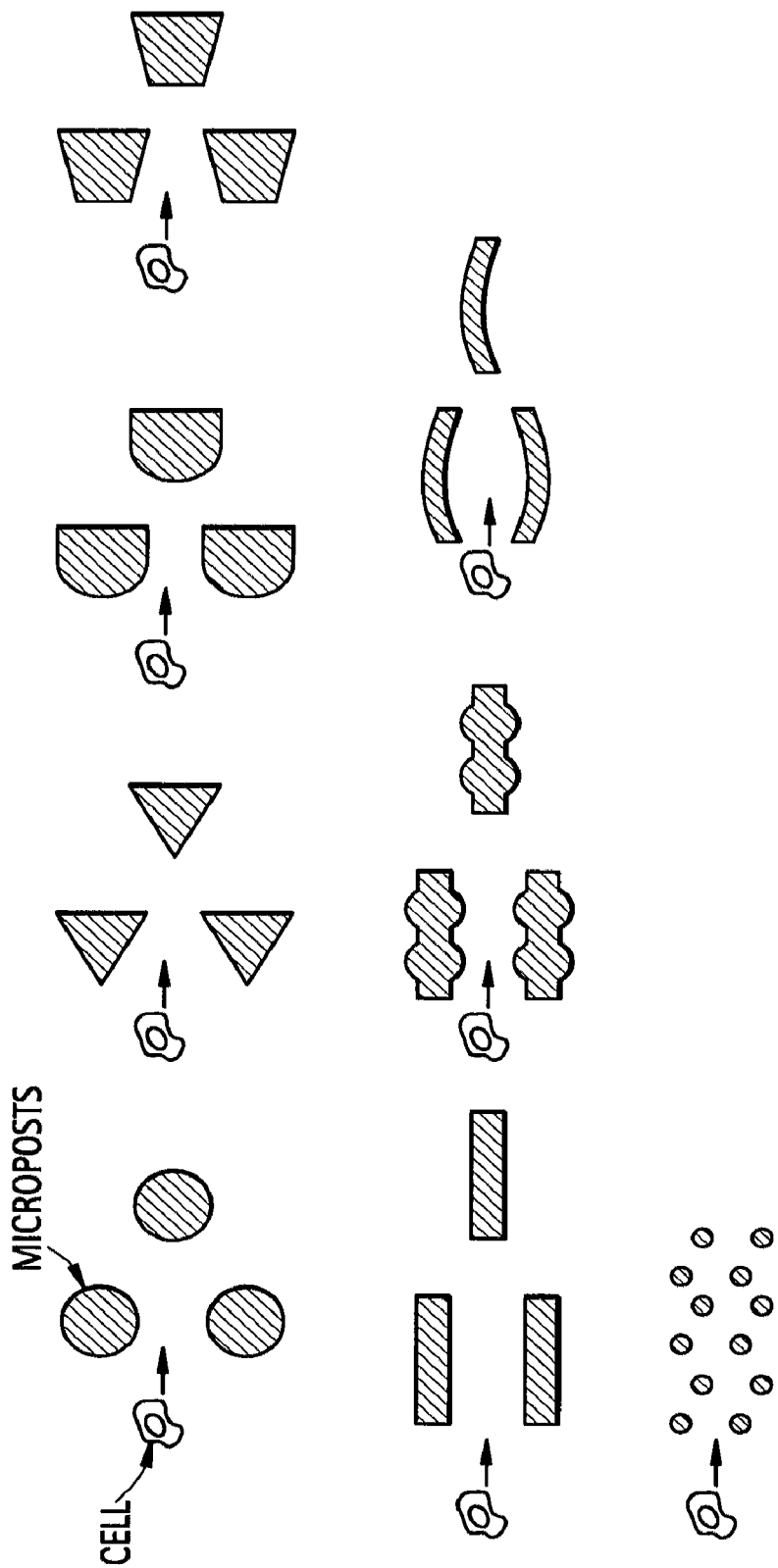
FIG. 10 is an illustration of types of obstacles.

The dimensions and geometry of the obstacles may vary significantly. For example, the obstacles may have cylindrical or square cross sections (FIG. 10). The distance between obstacles may also vary and may be different in the flow direction compared to the direction orthogonal to the flow. In some embodiments, the distance between the edges of the obstacles is slightly larger than the size of the largest cell in the mixture. This arrangements enables flow of cells without them being mechanically squeezed between the obstacles and thus damaged during the flow process, and also maximizes the numbers of collisions between cells and the obstacles in order to increase the probability of binding. The flow direction with respect to the orientation of the obstacles may also be altered to enhance interaction of cells with obstacles.

Figure 11A:
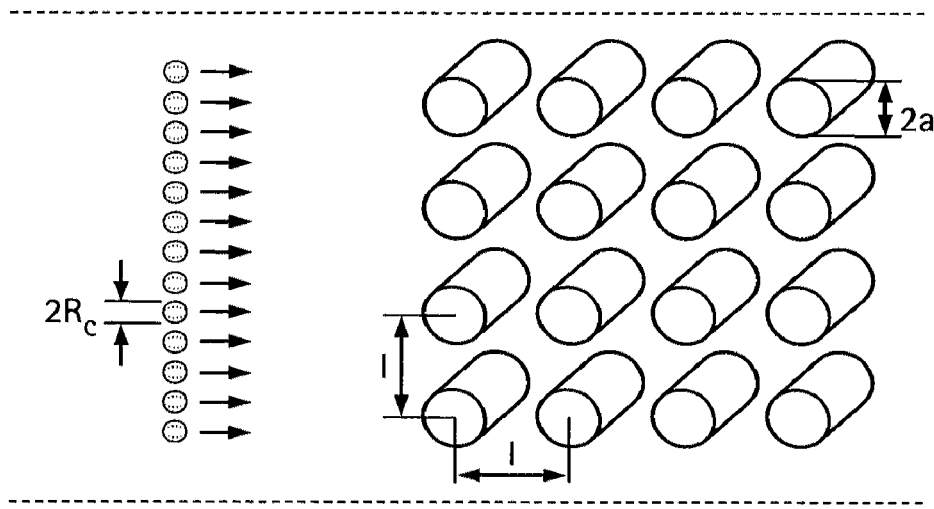
FIG. 11A is a schematic representation of a square array of obstacles. The square array has a capture efficiency of 40%.
Figure 11B:
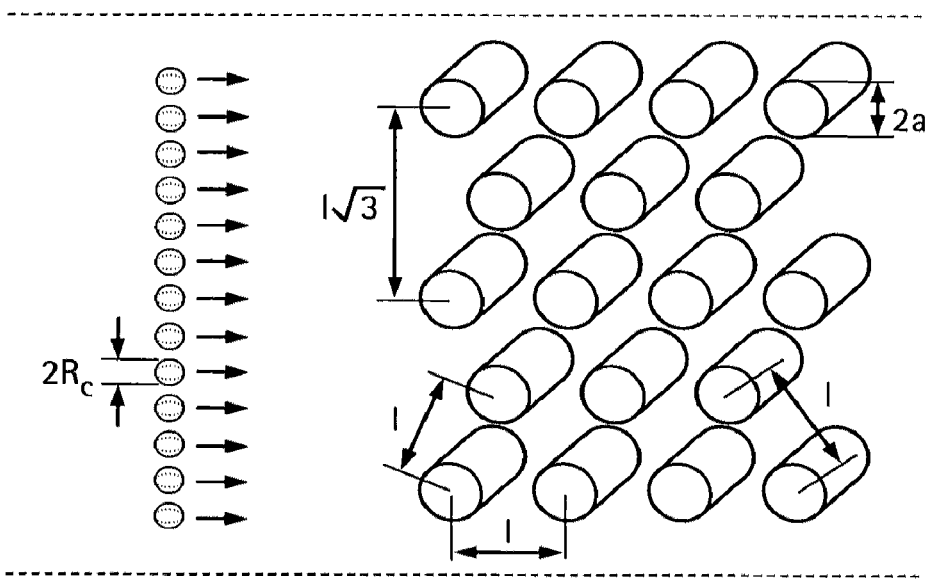
FIG. 11B is a schematic representation of an equilateral triangle array of obstacles. The equilateral triangle array has a capture efficiency of 56%.
Figure 12A:
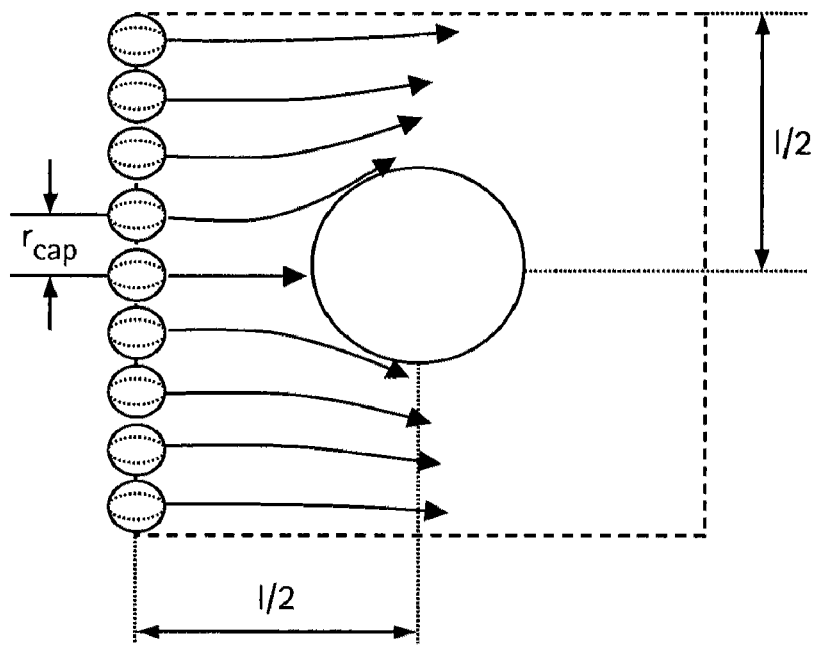
FIG. 12A is a schematic representation of the calculation of the hydrodynamic efficiency for a square array.
Figure 12B:
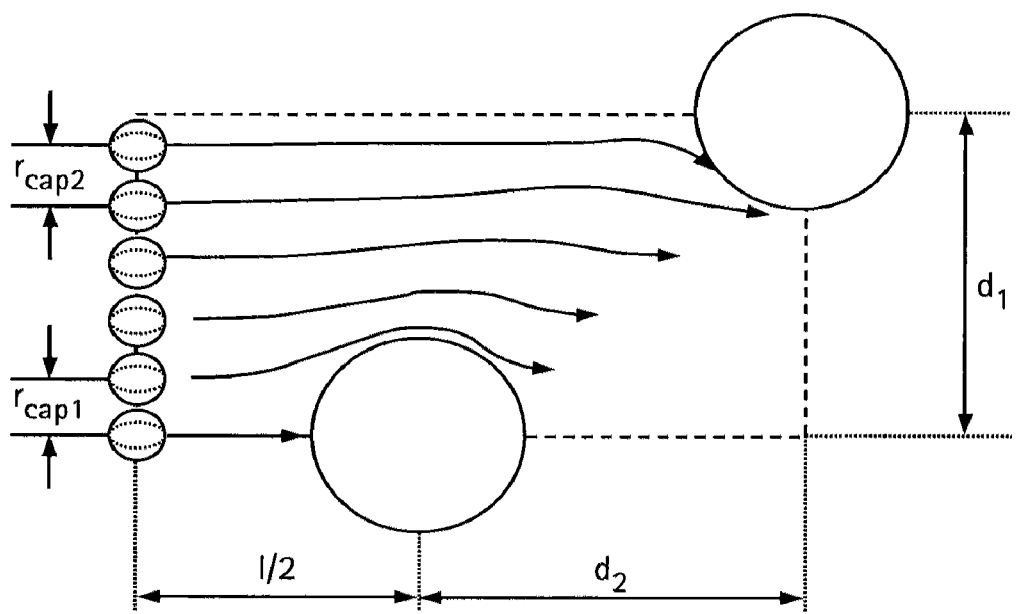
FIG. 12B is a schematic representation of the calculation of the hydrodynamic efficiency for a diagonal array

Exemplary arrangements of obstacles are shown in FIGS. 11A-11B. Each of these arrangements has a calculated capture efficiency. The calculation of cell attachment considered two different geometries: a square array (FIG. 11A), and an equilateral triangular array (FIG. 11B). Overall, results are presented in terms of the efficiency of adhesion. The calculations consist of two parts, computing the hydrodynamic efficiency ($\eta$) and the probability of adhesion. The hydrodynamic efficiency was determined as the ratio of the capture radius to the half-distance between the cylinders (FIGS. 12A and 12B). For the square array, $\eta=(2r_{cap}/l)*100\%$, and for other arrays, $\eta=((r_{cap1}+r_{cap2})/d_1)*100\%$, where $d_1=d_2=l/\sqrt{2}$ for a diagonal square array, and $d_1=l\sqrt{3}/2$, $d_2=l/2$ for a triangular array. The probability of adhesion represents the fraction of cells that can resist the applied force on the cell assuming an average of 1.5 bonds per cell and 75 pN per bond.

Figure 13A:
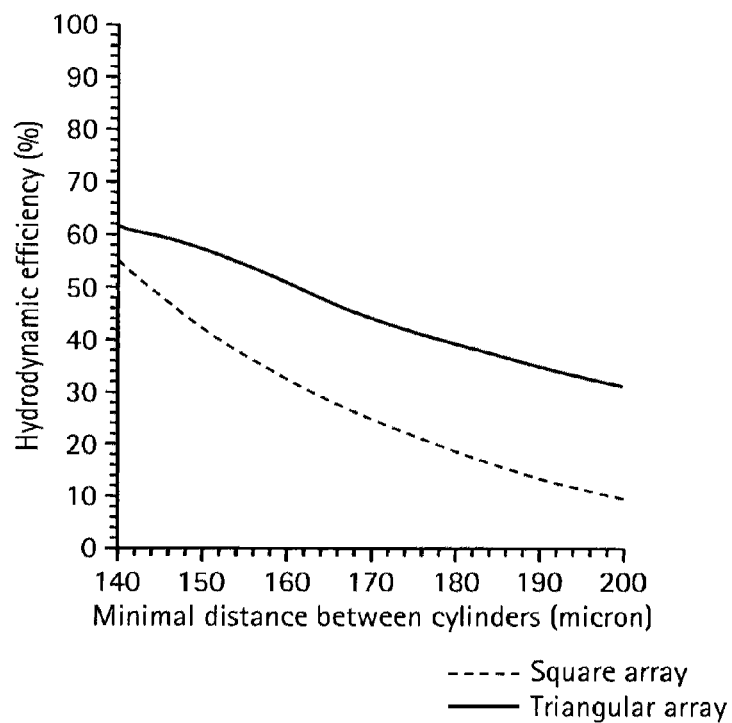
FIGS. 13A-13B are graphs of the hydrodynamic (13A) and overall efficiency (13B) for square array and triangular array for a pressure drop of 150 Pa/m. This pressure drop corresponds to a flow rate of 0.75 mL/hr in the planar geometry.
Figure 13B:
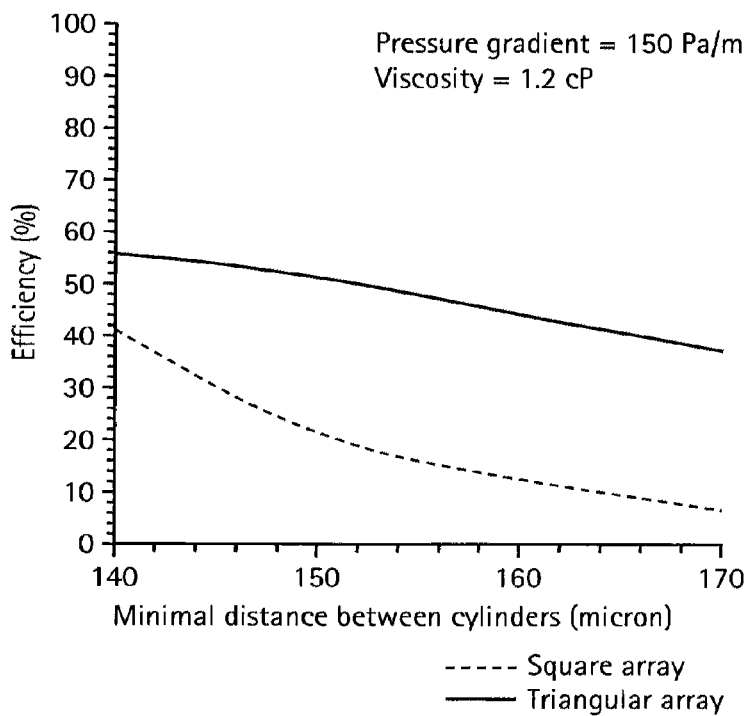

For the triangular array, more cells adhered to the second set of obstacles than the first set. FIGS. 13A-13B show that the efficiency declines as the spacing between obstacles increases. As the spacing increases there is a larger region outside the capture radius and the cells never contact the obstacles. Further, for the flow rates examined (0.25-1 mL/h), the overall probability of adhesion is high because the force pr cell is less than the force to break the bonds.

Figure 14A:
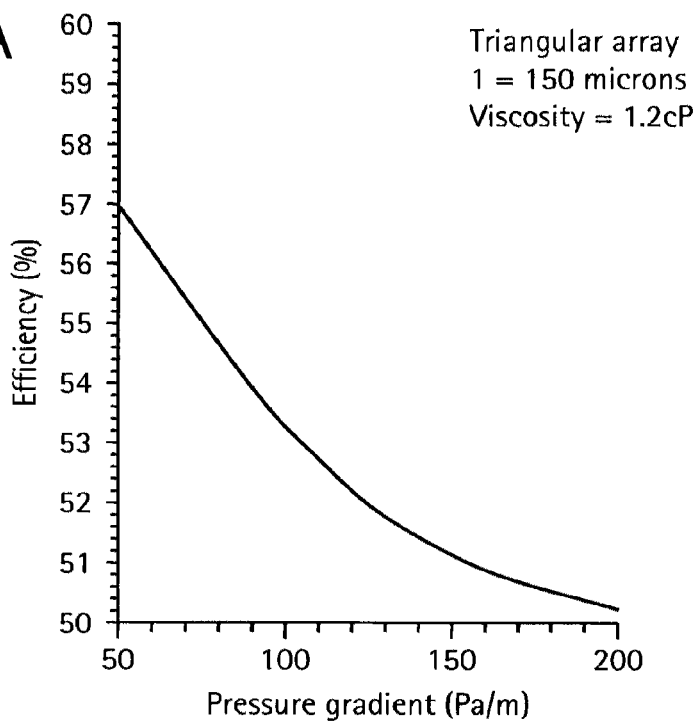
FIG. 14A is a graph of the overall efficiency as a function of pressure drop.
Figure 14B:
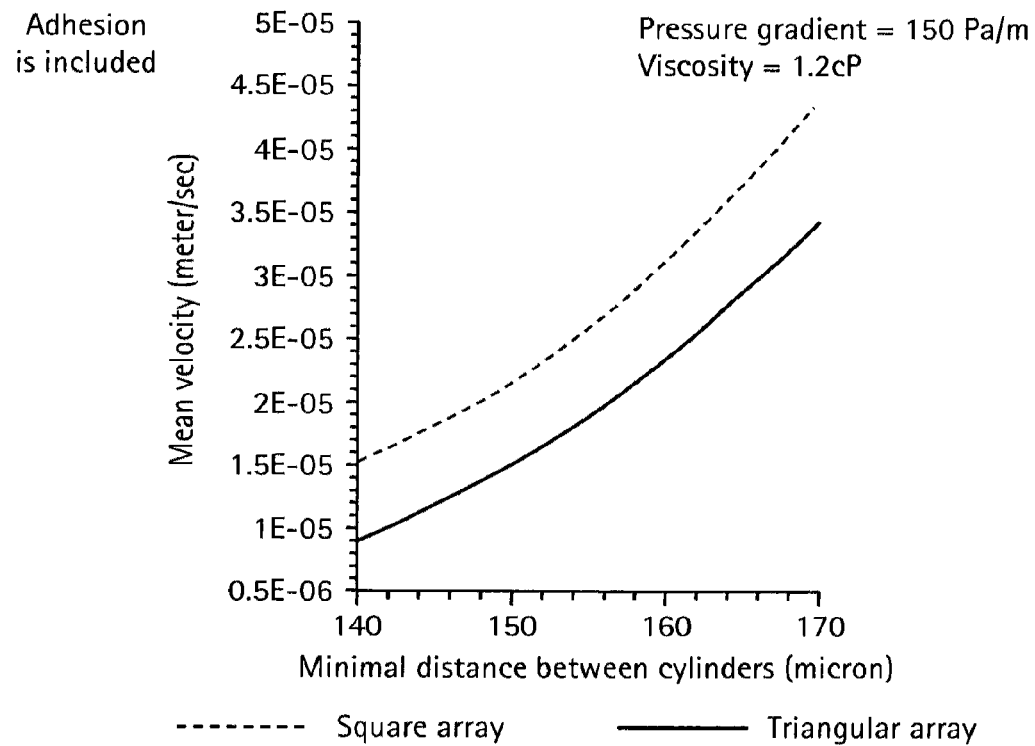
FIG. 14B is a graph of the effect of the obstacle separation on the average velocity.

For a triangular array and a spacing of 150 microns, the overall efficiency of capture drops 12% as the flow rate increases from 0.25 to 1 mL/h (FIGS. 14A-14B). Adhesion is not improved by going to lower flow rates since hydrodynamic capture is not improved. The mean velocity increases as the spacing between obstacles increases. The reason for this is that the calculations used a constant pressure drop. This differs from the experiments in which the flow rate is held fixed and the pressure drop varies. The results may be extrapolated from one case to another by one skilled in the art.

Figure 15:
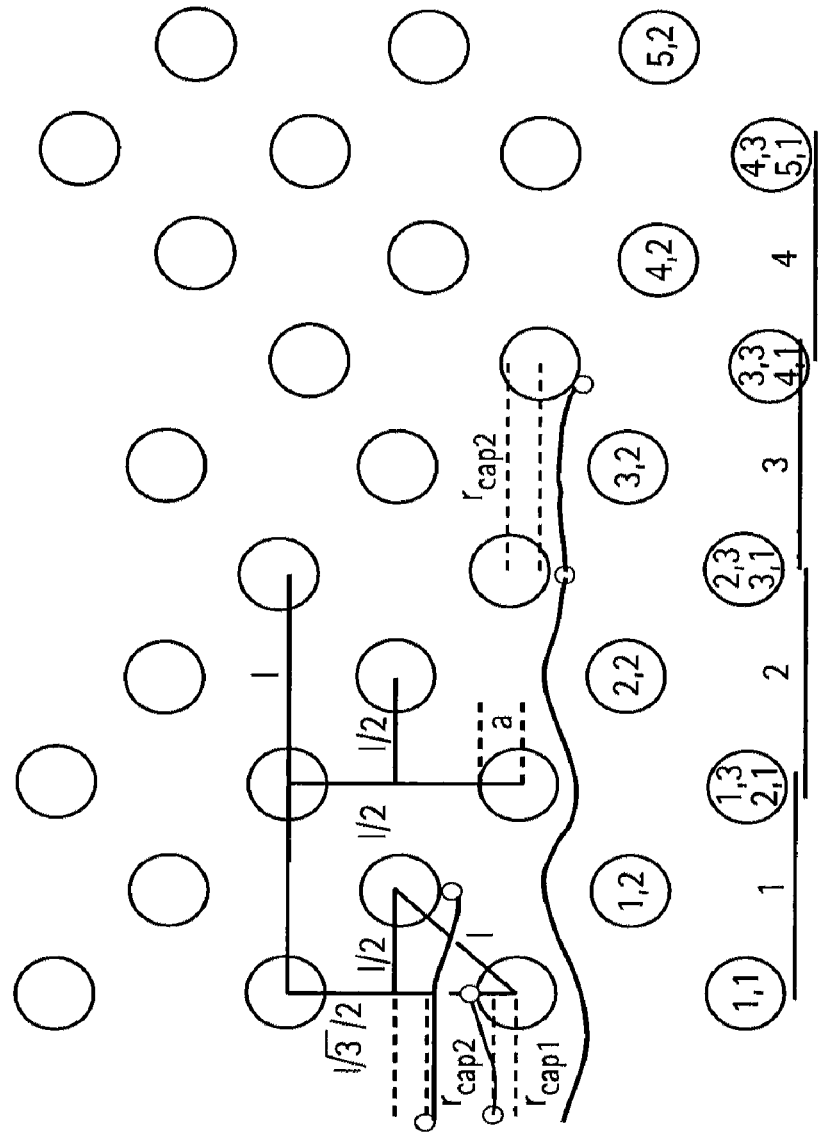
FIG. 15 is a schematic representation of the arrangement of obstacles for higher efficiency capture for an equilateral triangular array of obstacles in a staggered array. The capture radius $r_{cap_2}$=0.3391. The obstacles are numbered such that the first number refers to the triangle number and the second number refers to the triangle vertex. The staggered array has a capture efficiency of 98%.

A repeating triangular array provides limited capture of target cells because most of the capture occurs in the first few rows. The reason for this is that the flow field becomes established in these rows and repeats. The first capture radius does not produce much capture whereas most of the capture is within the second capture radius (FIG. 15). Once cells within the capture radii are captured, the only way in which capture could occur is through cell-cell collisions to shift cells off their streamlines or secondary capture. With reference to FIG.

Figure 16A:
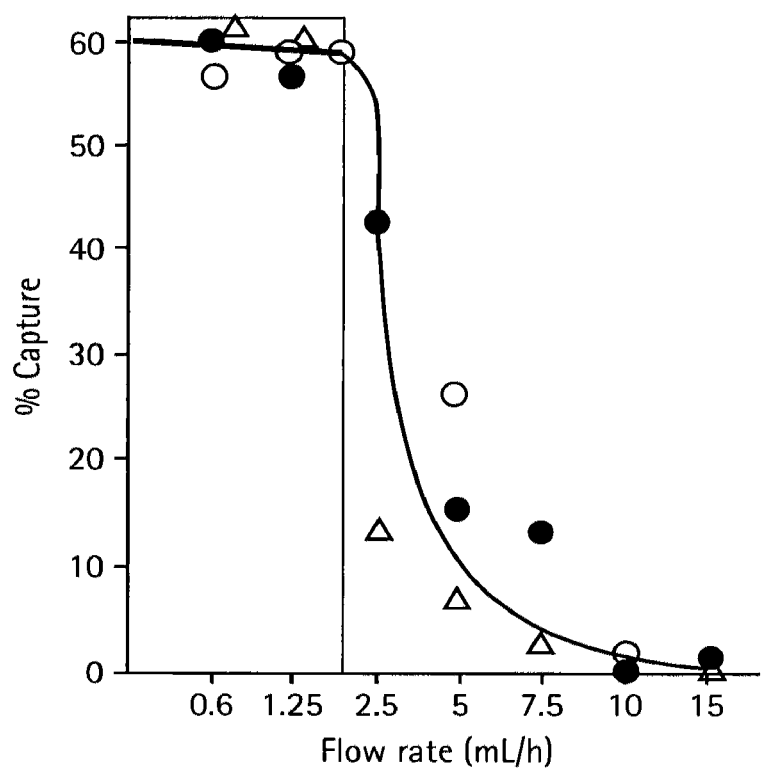
FIG. 16A is a graph of the percent capture of cells as a function of the flow rate for a 100 μm diameter obstacle geometry with a 50 μm edge-to-edge spacing. The operating flow regime was established across multiple cell types: cancer cells, normal connective tissue cells, and maternal and fetal samples. An optimal working flow regime is at 2.5 ml/hr.
Figure 16B:
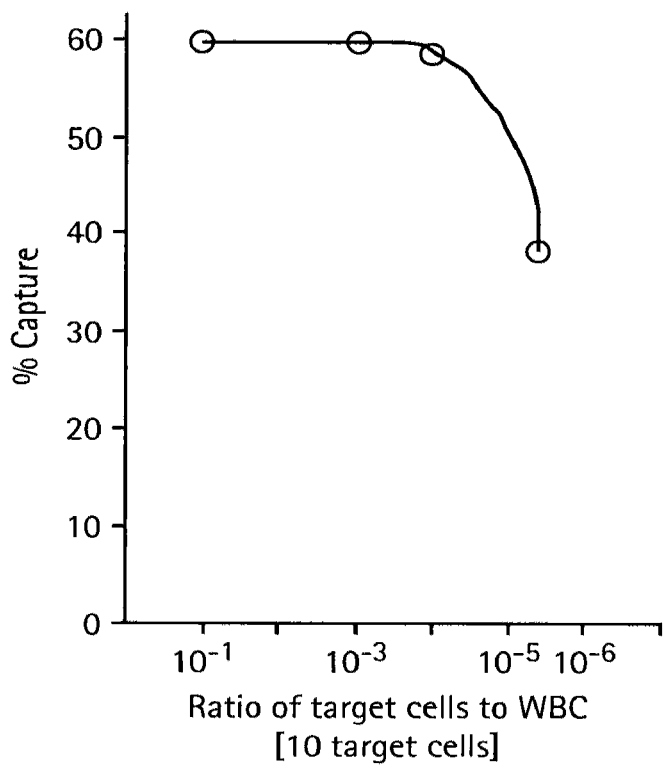
FIG. 16B is a graph of the percent capture of cells as a function of the ratio of targets cells to white blood cells. The model system was generated by spiking defined number of either cancer cells, normal connective tissue cells, or cells from cord blood into defined number of cells from buffy coat of adult blood. The ratio of the contaminating cells to target cells was incrementally increased 5 log with as few as 10 target cells in the mixture. Yield was computed as the difference between number of spiked target cells captured on posts and number of cells spiked into the sample.

15, in order to enhance capture, after the flow field is established, the rows are shifted by a distance in the vertical direction (normal to flow) by a distance equal to $r_{cap_2}$=0.339l. The first five columns form two regular regions of equilateral triangles. This allows the flow to be established and be consistent with the solution for an equilateral triangular array. To promote capture of cells that fall outside $r_{cap_2}$, the fourth column is shifted downward by a distance $r_{cap_2}$. All columns are separated by a distance equal to l/2. A cell which falls outside $r_{cap_2}$ is shown being captured by the first obstacle in the fourth triangle (seventh column). Triangles 4 and 5 would be equilateral. In triangle 6, the vertex 3 is shifted downward by a distance $r_{cap_2}$. This arrangement may be repeated every third triangle, i.e., the repeat distance is 2.5l. FIGS. 16A and 16B illustrate the efficiency of capture as a function of flow rate and relative population of the desired cells.

The top layer is desirably made of glass and has two slits drilled ultrasonically for inlet and outlet flows. The slit inlet/outlet dimensions are, for example, 2 cm long and 0.5 mm wide. FIG. 17 shows the details for the inlet/outlet geometry. A manifold may then be incorporated onto the inlet/outlet slits. The inlet manifold accepts blood cells from an infusion syringe pump or any other delivery vehicle, for example, through a flexible, biocompatible tubing. Similarly the outlet manifold is connected to a reservoir to collect the solution and cells exiting the device.

The inlet and outlet configuration and geometry may be designed in various ways. For example, circular inlets and outlets may be used. An entrance region devoid of obstacles is then incorporated into the design to ensure that blood cells are uniformly distributed when they reach the region where the obstacles are located. Similarly, the outlet is designed with an exit region devoid of obstacles to collect the exiting cells uniformly without damage.

The overall size of an exemplary device is shown in FIG. 9 (top inset). The length is 10 cm and the width is 5 cm. The area that is covered with obstacles is 9 cm 4.5 cm. The design is flexible enough to accommodate larger or smaller sizes for different applications.

The overall size of the device may be smaller or larger, depending on the flow throughput and the number of cells to be depleted (or captured). A larger device could include a greater number of obstacles and a larger surface area for cell capture. Such a device may be necessary if the amount of sample, e.g., blood, to be processed is large.

Figure 18:
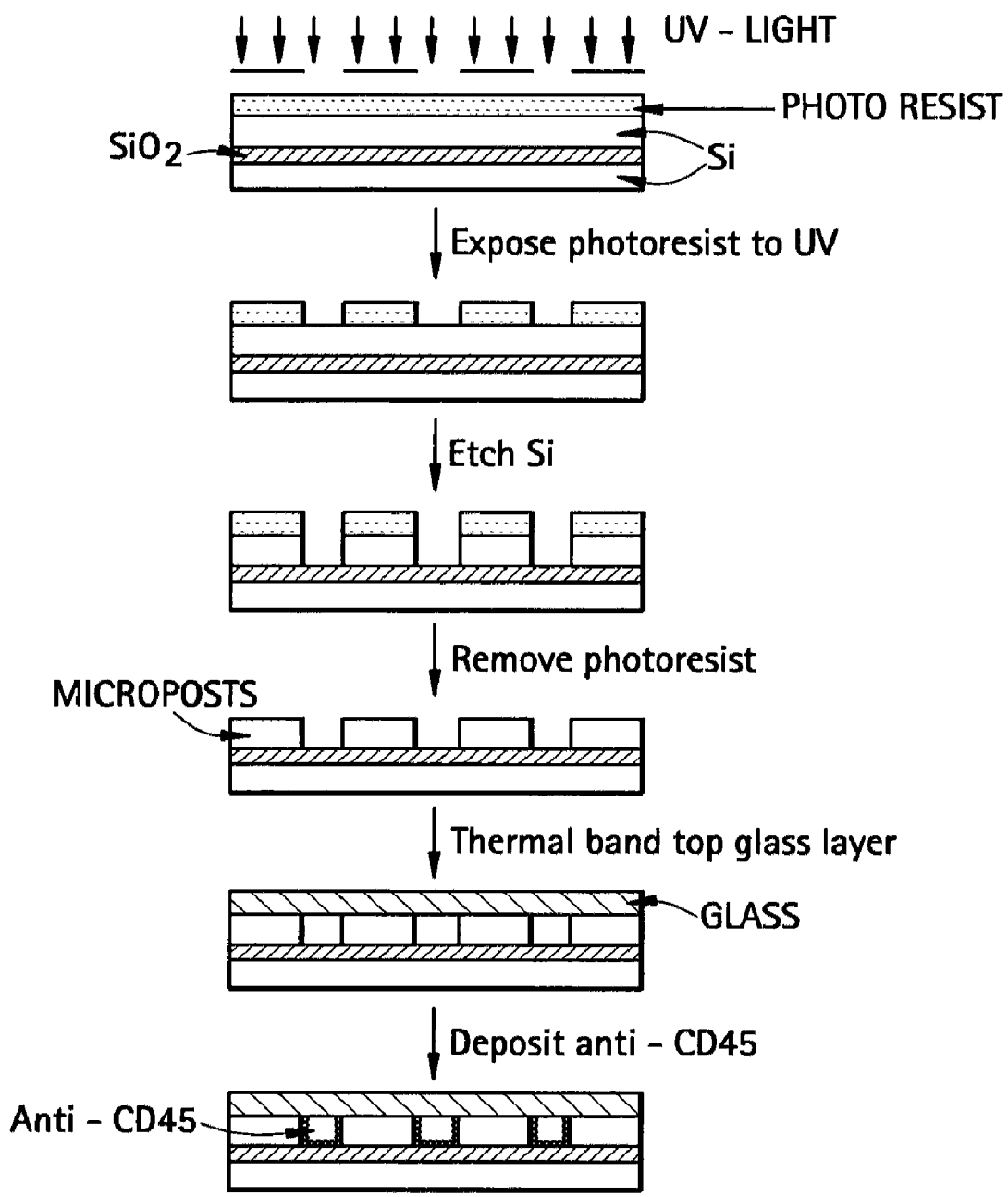
FIG. 18 is an illustration of a method of fabricating a cell binding device.

Fabrication. An exemplary method for fabricating a device of the invention is summarized in FIG. 18. In this example, standard photolithography is used to create a photoresist pattern of obstacles on a silicon-on-insulator (SOI) wafer. A SOI wafer consists of a 100 µm thick Si(100) layer atop a 1 µm thick $SiO_2$ layer on a 500 µm thick Si(100) wafer. To optimize photoresist adhesion, the SOI wafers may be exposed to high-temperature vapors of hexamethyldisilazane prior to photoresist coating. UV-sensitive photoresist is spin coated on the wafer, baked for 30 minutes at 90° C., exposed to UV light for 300 seconds through a chrome contact mask, developed for 5 minutes in developer, and post-baked for 30 minutes at 90° C. The process parameters may be altered depending on the nature and thickness of the photoresist. The pattern of the contact chrome mask is transferred to the photoresist and determines the geometry of the obstacles.

Upon the formation of the photoresist pattern that is the same as that of the obstacles, the etching is initiated. $SiO_2$ may serve as a stopper to the etching process. The etching may also be controlled to stop at a given depth without the use of a stopper layer. The photoresist pattern is transferred to the 100 µm thick Si layer in a plasma etcher. Multiplexed deep etching may be utilized to achieve uniform obstacles. For example, the substrate is exposed for 15 seconds to a fluorine-rich plasma flowing $SF_6$, and then the system is switched to a fluorocarbon-rich plasma flowing only $C_4F_8$ for 10 seconds, which coats all surfaces with a protective film. In the subsequent etching cycle, the exposure to ion bombardment clears the polymer preferentially from horizontal surfaces and the cycle is repeated multiple times until, e.g., the $SiO_2$ layer is reached.

To couple a binding moiety to the surfaces of the obstacles, the substrate may be exposed to an oxygen plasma prior to surface modification to create a silicon dioxide layer, to which binding moieties may be attached. The substrate may then be rinsed twice in distilled, deionized water and allowed to air dry. Silane immobilization onto exposed glass is performed by immersing samples for 30 seconds in freshly prepared, 2% v/v solution of 3-[(2-aminoethyl)amino]propyltrimethoxysilane in water followed by further washing in distilled, deionized water. The substrate is then dried in nitrogen gas and baked. Next, the substrate is immersed in 2.5% v/v solution of glutaraldehyde in phosphate buffered saline for 1 hour at ambient temperature. The substrate is then rinsed again, and immersed in a solution of 0.5 mg/mL binding moiety, e.g., anti-CD71, anti-CD36, anti-GPA, or anti-CD45, in distilled, deionized water for 15 minutes at ambient temperature to couple the binding agent to the obstacles. The substrate is then rinsed twice in distilled, deionized water, and soaked overnight in 70% ethanol for sterilization.

There are multiple techniques other than the method described above by which binding moieties may be immobilized onto the obstacles and the surfaces of the device. Simple physio-absorption onto the surface may be the choice for simplicity and cost. Another approach may use self-assembled monolayers (e.g., thiols on gold) that are functionalized with various binding moieties. Additional methods may be used depending on the binding moieties being bound and the material used to fabricate the device. Surface modification methods are known in the art. In addition, certain cells may preferentially bind to the unaltered surface of a material. For example, some cells may bind preferentially to positively charged, negatively charged, or hydrophobic surfaces or to chemical groups present in certain polymers.

The next step involves the creation of a flow device by bonding a top layer to the microfabricated silicon containing the obstacles. The top substrate may be glass to provide visual observation of cells during and after capture. Thermal bonding or a UV curable epoxy may be used to create the flow chamber. The top and bottom may also be compression fit, for example, using a silicone gasket. Such a compression fit may be reversible. Other methods of bonding (e.g., wafer bonding) are known in the art. The method employed may depend on the nature of the materials used.

The cell binding device may be made out of different materials. Depending on the choice of the material different fabrication techniques may also be used. The device may be made out of plastic, such as polystyrene, using a hot embossing technique. The obstacles and the necessary other structures are embossed into the plastic to create the bottom surface. A top layer may then be bonded to the bottom layer. Injection molding is another approach that can be used to create such a device. Soft lithography may also be utilized to create either a whole chamber made out of poly(dimethylsiloxane) (PDMS), or only the obstacles may be created in PDMS and then bonded to a glass substrate to create the closed chamber. Yet another approach involves the use of epoxy casting techniques to create the obstacles through the use of UV or temperature curable epoxy on a master that has the negative replica of the intended structure. Laser or other types of micromachining approaches may also be utilized to create the flow chamber. Other suitable polymers that may be used in the fabrication of the device are polycarbonate, polyethylene, and poly(methyl methacrylate). In addition, metals like steel and nickel may also be used to fabricate the device of the invention, e.g., by traditional metal machining. Three-dimensional fabrication techniques (e.g., stereolithography) may be employed to fabricate a device in one piece. Other methods for fabrication are known in the art.

Methods. The methods of the invention involve contacting a mixture of cells with the surfaces of a microfluidic device. A population of cells in a complex mixture of cells such as blood then binds to the surfaces of the device. Desirably, at least 60%, 70%, 80%, 90%, 95%, 98%, or 99% of cells that are capable of binding to the surfaces of the device are removed from the mixture. The surface coating is desirably designed to minimize nonspecific binding of cells. For example, at least 99%, 98%, 95%, 90%, 80%, or 70% of cells not capable of binding to the binding moiety are not bound to the surfaces of the device. The selective binding in the device results in the separation of a specific living cell population from a mixture of cells. Obstacles are present in the device to increase surface area for cells to interact with while in the chamber containing the obstacles so that the likelihood of binding is increased. The flow conditions are such that the cells are very gently handled in the device without the need to deform mechanically in order to go in between the obstacles. Positive pressure or negative pressure pumping or flow from a column of fluid may be employed to transport cells into and out of the microfluidic devices of the invention. In an alternative embodiment, cells are separated from non-cellular matter, such as non-biological matter (e.g., beads), non-viable cellular debris (e.g., membrane fragments), or molecules (e.g., proteins, nucleic acids, or cell lysates).

Figure 19:
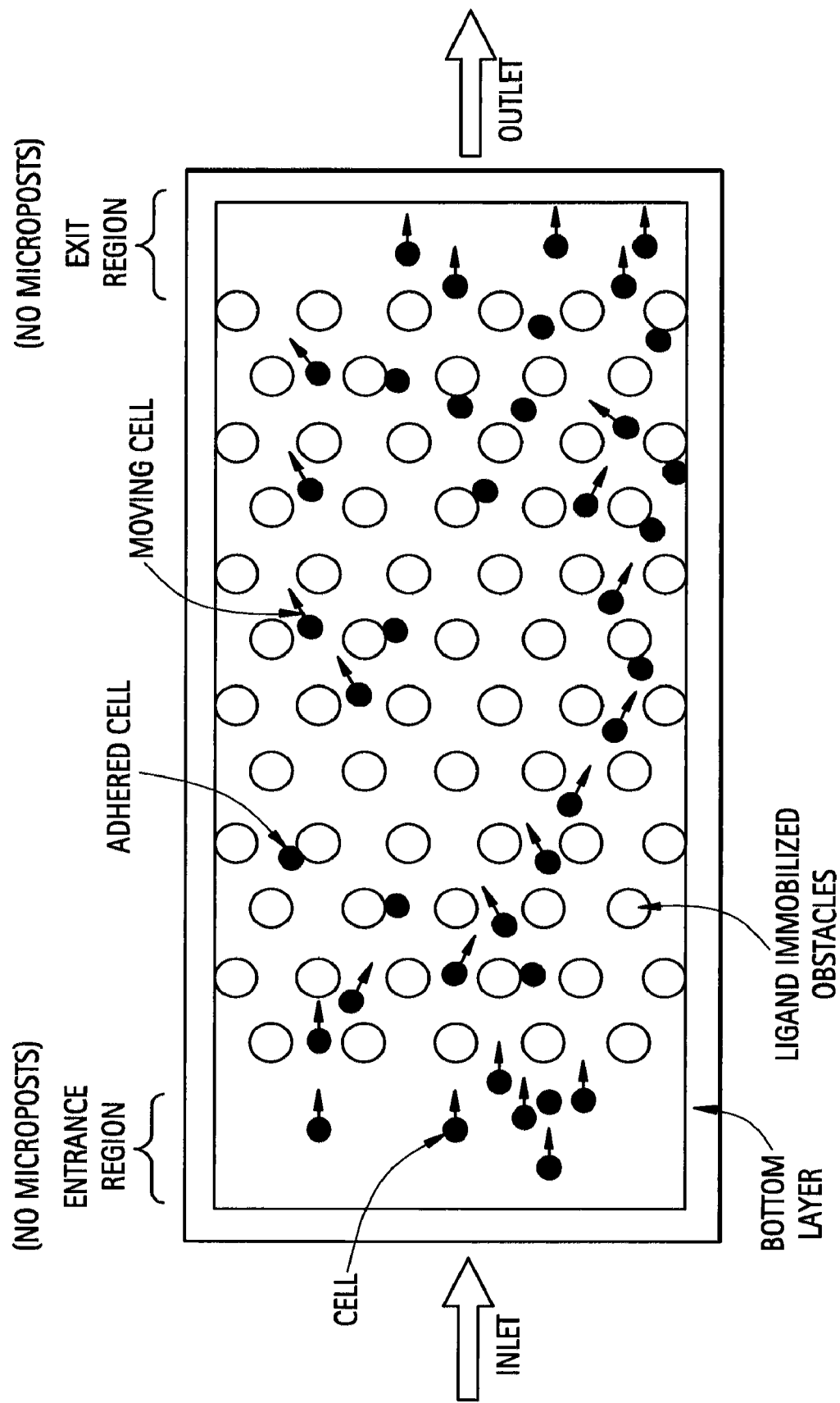
FIG. 19 is an illustration of a mixture of cells flowing through a cell binding device.

FIG. 19 shows cells expressing a specific surface antigen binding to a binding moiety coated onto obstacles, while other cells flow through the device (small arrow on cells depict the directionality of cells that are not bound to the surface). The top and bottom surfaces of the flow apparatus may also be coated with the same binding moiety, or a different binding moiety, to promote cell binding.

Exemplary cell types that may be separated using the methods described herein include adult red blood cells, fetal red blood cells, trophoblasts, fetal fibroblasts, white blood cells (such as T cells, B cells, and helper T cells), infected white blood cells, stem cells (e.g., CD34 positive hematopoeitic stem cells), epithelial cells, tumor cells, and infectious organisms (e.g., bacteria, protozoa, and fungi).

Figure 20:
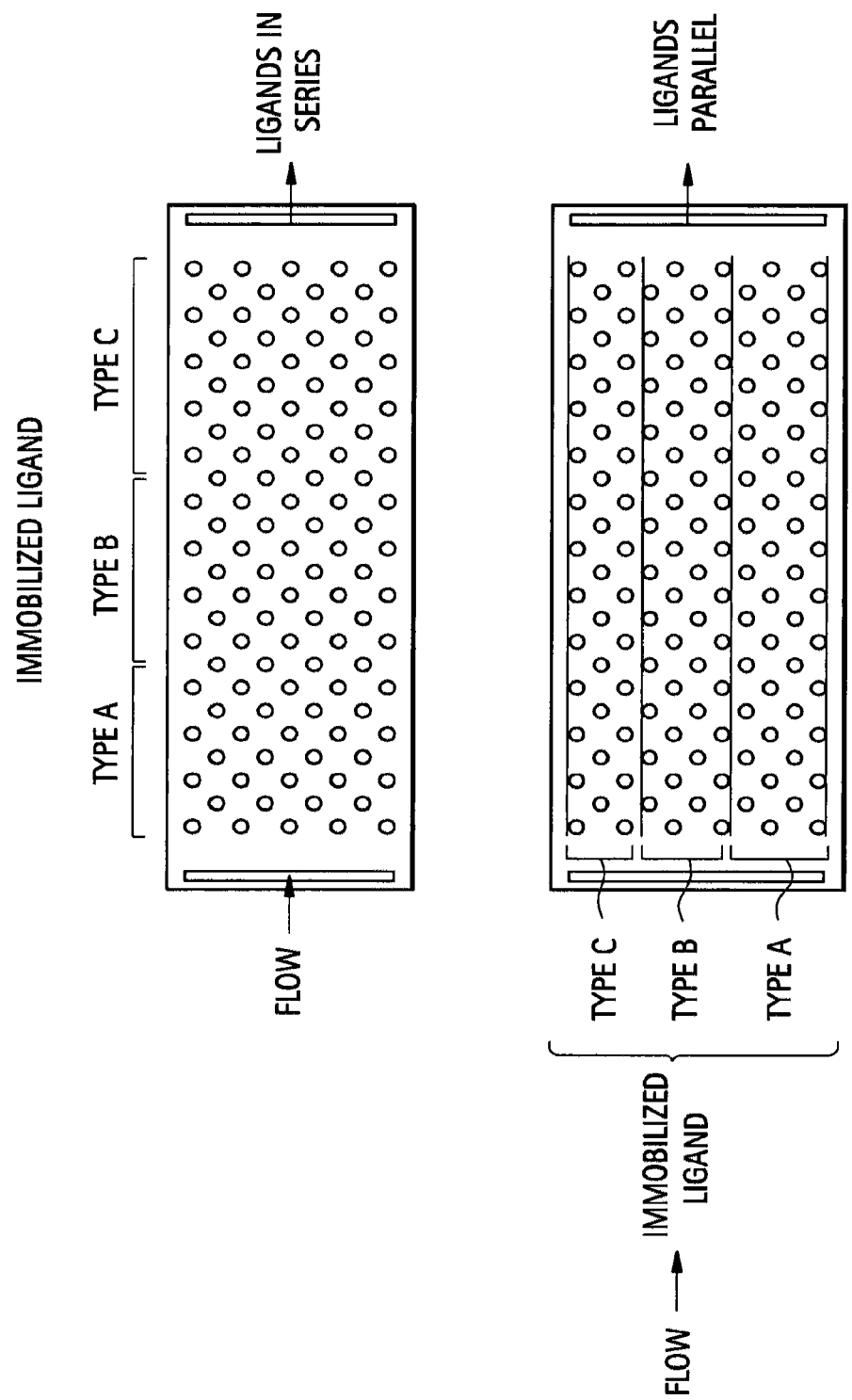
FIG. 20A is an illustration of a cell binding device for trapping different types of cells in series.
FIG. 20B is an illustration of a cell binding device for trapping different types of cells in parallel.

Samples may be fractionated into multiple homogeneous components using the methods described herein. Multiple similar devices containing different binding moieties specific for a population of cells may be connected in series or in parallel. Serial separation may be employed when one seeks to isolate rare cells. On the other hand, parallel separation may be employed when one desires to obtain differential distribution of various populations in blood. FIGS. 20A and 20B show parallel and serial systems for the separation of multiple populations of cells from blood. For parallel devices, two or more sets of obstacles that bind different types of cells may be located in distinct regions or they may be interspersed among each other, e.g., in a checkerboard pattern or in alternating rows. In addition, a set of obstacles may be attached to the top of the device and another set may be attached to the bottom of the device. Each set may then be derivatized to bind different populations of cells. Once a sample has passed through the device, the top and bottom may be separated to provide isolated samples of two different types of cells.

Figure 21:
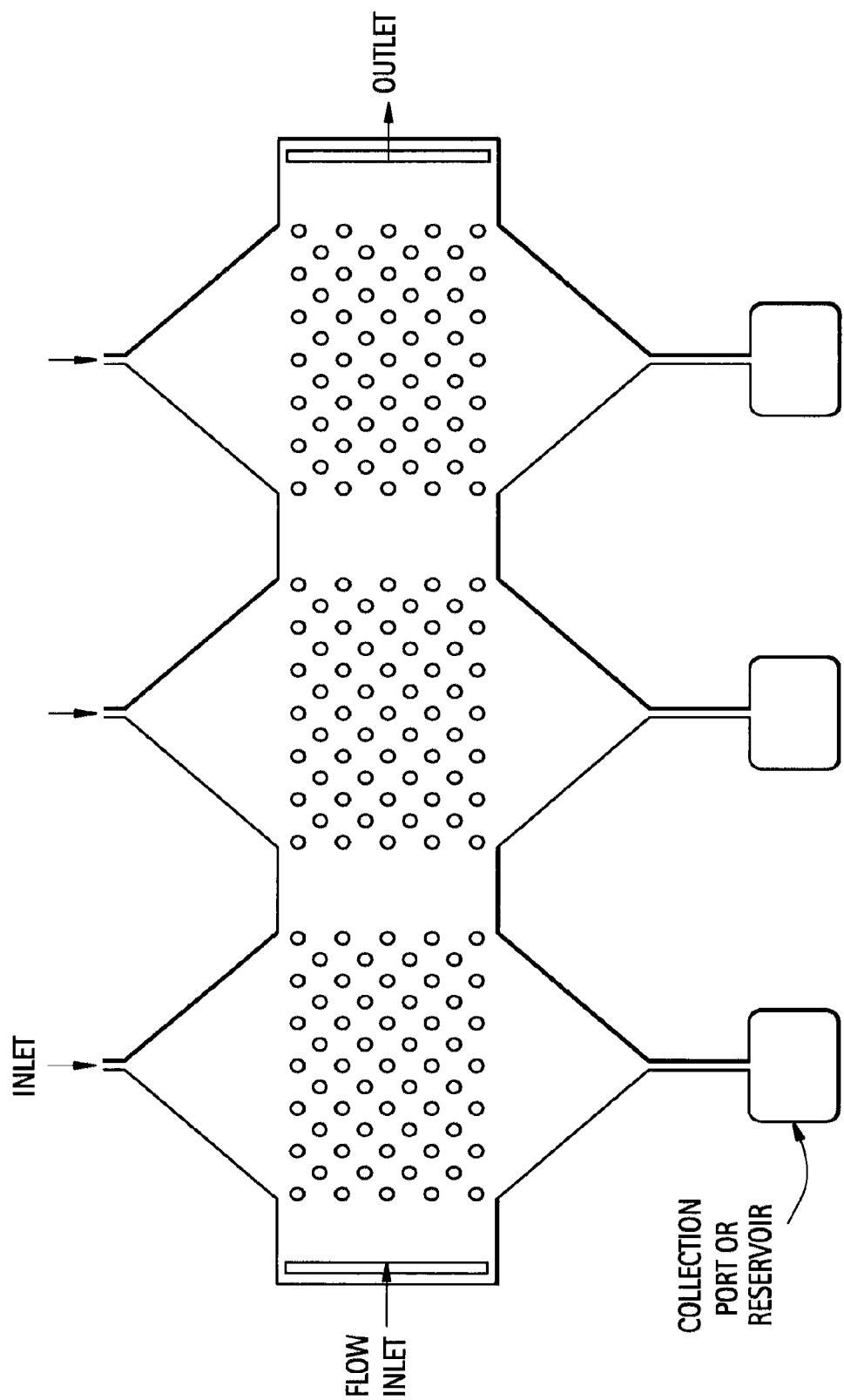
FIG. 21 is an illustration of a cell binding device that enables recovery of bound cells.

The cell binding device may be used to deplete the outlet flow of a certain population of cells, or to capture a specific population of cells expressing a certain surface molecule for further analysis. The cells bound to obstacles may be removed from the chamber for further analysis of the homogeneous population of cells (FIG. 21). This removal may be achieved by incorporating one or more additional inlets and exits orthogonal to the flow direction. Cells may be removed from the chamber by purging the chamber at an increased flow rate, that is higher shear force, to overcome the binding force between the cells and the obstacles. Other approaches may involve coupling binding moieties with reversible binding properties, e.g., that are actuated by pH, temperature, or electrical field. The binding moiety, or the molecule bound on the surface of the cells, may also be cleaved by enzymatic or other chemical means.

Figure 22A:
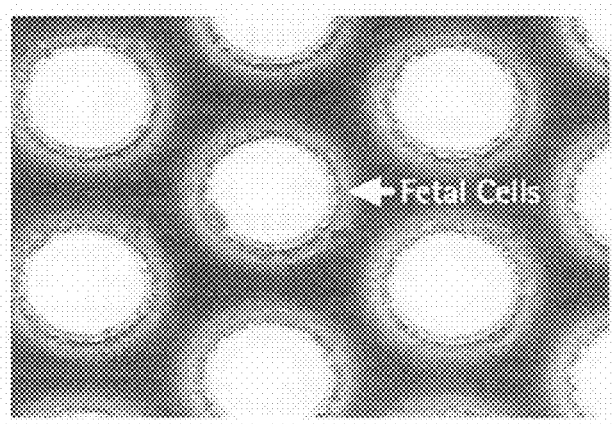
FIG. 22A is an optical micrograph of fetal red blood cells adhered to an obstacle of the invention.
Figure 22B:
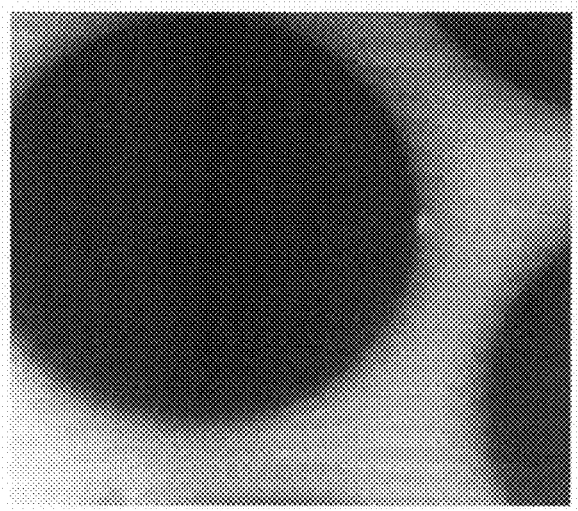
FIG. 22B is a fluorescent micrograph showing the results of a FISH analysis of a fetal red blood cell attached to an obstacle of the invention.
Figure 22C:
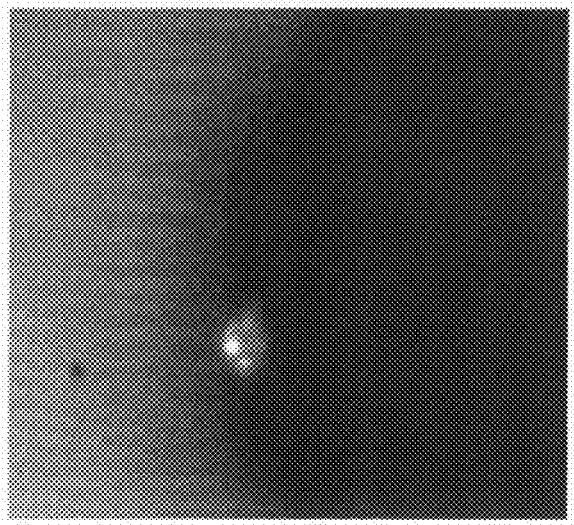
FIG. 22C is a close up micrograph of FIG. 22B showing the individual hybridization results for the fetal red blood cell.

In the example of fetal red blood cell isolation, a sample having passed through a lysis device is passed through a cell binding device, whose surfaces are coated with CD45. White blood cells expressing CD45 present in the mixture bind to the walls of the device, and the cells that pass through the device are enriched in fetal red blood cells. Alternatively, the obstacles and device surfaces are coated with anti-CD71 in order to bind fetal nucleated red blood cells (which express the CD71 cell surface protein) from a whole maternal blood sample. One percent of adult white blood cells also express CD71. A sample of maternal blood is passed through the device and both populations of cells that express CD71 bind to the device. This results in the depletion of fetal red blood cells from the blood sample. The fetal cells are then collected and analyzed. For example, cells are collected on a planar substrate for fluorescence in situ hybridization (FISH), followed by fixing of the cells and imaging. FIGS. 22A-22C show the use of FISH on a cell bound to an obstacle in a binding device of the invention. The cell, of fetal origin, is stained for X and Y chromosomes using fluorescent probes. These data show the feasibility of optical imaging of FISH stained cells on posts for detection and diagnosis of chromosomal abnormalities.

Figure 23:
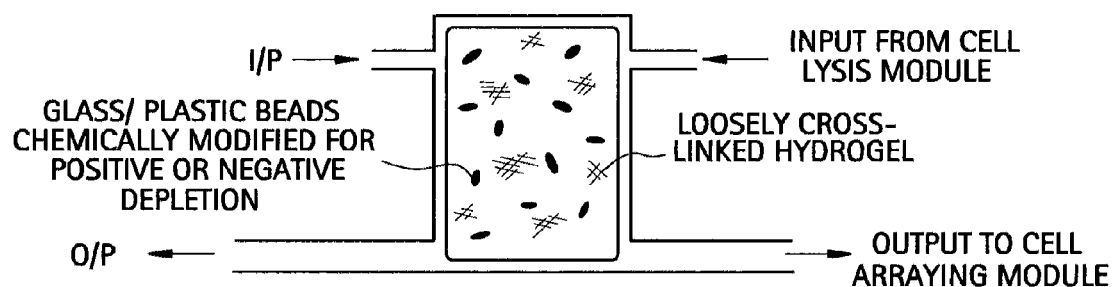
FIG. 23 is an illustration of a cell binding device in which beads trapped in a hydrogel are used to capture cells.

Alternative Embodiments. Another embodiment of the cell binding device utilizes chemically derivatized glass/plastic beads entrapped in a loosely cross-linked hydrogel, such as, but not limited to, poly(vinyl alcohol), poly(hydroxyl-ethyl methacrylate), polyacrylamide, or polyethylene glycol (FIG. 23). The chemically derivatized beads serve as the obstacles in this embodiment. A mixture of cells is directed into the cell depletion device via two diametrically opposed inputs. Positive pressure (e.g., from an infusion pump or column of fluid) or negative pressure (e.g., from a syringe pump in pull mode, a vacuum pump, or an aspirator) drives the liquid through the hydrogel. The interaction of the cells in the sample with the chemically derivatized beads dispersed in the three-dimensional volume of the hydrogel results in either depletion of cells, e.g., white blood cells, (negative selection) or capture of cells, e.g., fetal red blood cells, (positive selection). The molecular weight, cross-link density, bead density, and distribution and flow rates can be optimized to allow for maximal interaction and capture of relevant cells by the beads. The high-water content hydrogel provides a structure to trap the beads while allowing ease of flow through of the sample. The sample is then collected through two diametrically opposed outputs. The bifurcated input/output channel design assures maximal homogeneous distribution of the sample through the volume of the hydrogel.

In yet another embodiment, the beads are replaced by direct chemical derivatization of the side chains of the hydrogel polymer with the binding moiety (e.g., synthetic ligand or monoclonal antibody (mAb)). This approach can provide a very high density of molecular capture sites and thereby assure higher capture probability. An added advantage of this approach is a potential use of the hydrogel based cell depletion device as a sensor for fetal cell capture in the positive selection mode (select for fetal cells with specific mAb), for example, if the polymer backbone and side chain chemistry is designed to both capture the fetal cells and in the process further cross-link the hydrogel. The cells bind to numerous side chains via antigen-mAb interaction and thus serve as a cross-linker for the polymer chains, and the reduction in flow output over time due to increased polymer cross-link density can be mathematically equated to the number of fetal cells captured within the 3D matrix of the polymer. When the desired number of fetal cells is captured (measured by reduction in output flow rate), the device can stop further processing of the maternal sample and proceed to analysis of the fetal cells. The captured fetal cells can be released for analysis by use of a photoactive coupling agent in the side chain. The photoreactive agent couples the target ligand or mAb to the polymer backbone, and on exposure to a pulse of UV or IR radiation, the ligands or mAbs and associated cells are released.

C. Cell Arraying

In this device, a mixture of cells that has typically been depleted of unwanted cells is arrayed in a microfluidic device. An exemplary device for this step is described in International Publication No. WO 01/35071. The cells in the array are then assayed, e.g., by microscopy or colorimetric assay, to locate desired cells. The desired cells may then be analyzed on the array, e.g., by lysis followed by PCR, or the cells may be collected from the array by a variety of mechanisms, e.g., optical tweezers. In the exemplary device described in WO 01/35071, the cells are introduced into the arraying device and may passively settle into holes machined in the device. Alternatively, positive or negative pressure may be employed to direct the cells to the holes in the array. Once the cells have been deposited in the holes, selected cells may be individually released from the array by actuators, e.g., bubble actuated pumps. Other methods for immobilizing and releasing cells, e.g., dielectrophoretic trapping, may also be used in an arraying device. Once released from the array, cells may be collected and subjected to analysis. For example, a fetal red blood cell is identified in the array and then analyzed for genetic abnormalities. Fetal red blood cells may be identified morphologically or by a specific molecular marker (e.g., fetal hemoglobin, transferring receptor (CD71), thrombospondin receptor (CD36), or glycophorin A (GPA)).

D. Size-Based Separation

Another device is a device for the separation of particles based on the use of sieves that selectively allow passage of particles based on their size, shape, or deformability. The size, shape, or deformability of the pores in the sieve determines the types of cells that can pass through the sieve. Two or more sieves can be arranged in series or parallel, e.g., to remove cells of increasing size successively.

Device. In one embodiment, the sieve includes a series of obstacles that are spaced apart. A variety of obstacle sizes, geometries, and arrangements can be used in devices of the invention. Different shapes of obstacles, e.g., those with circular, square, rectangular, oval, or triangular cross sections, can be used in a sieve. The gap size between the obstacles and the shape of the obstacles may be optimized to ensure fast and efficient filtration. For example, the size range of the RBCs is on the order of 5-8 µm, and the size range of platelets is on the order of 1-3 µm. The size of all WBCs is greater than 10 µm. Large gaps between obstacles increase the rate at which the RBCs and the platelets pass through the sieve, but increased gap size also increases the risk of losing WBCs. Smaller gap sizes ensure more efficient capture of WBCs but also a slower rate of passage for the RBCs and platelets. Depending on the type of application different geometries can be used.

In addition to obstacles, sieves may be manufactured by other methods. For example, a sieve could be formed by molding, electroforming, etching, drilling, or otherwise creating holes in a sheet of material, e.g., silicon, nickel, or PDMS. Alternatively, a polymer matrix or inorganic matrix (e.g., zeolite or ceramic) having appropriate pore size could be employed as a sieve in the devices described herein.

One problem associated with devices of the invention is clogging of the sieves. This problem can be reduced by appropriate sieve shapes and designs and also by treating the sieves with non-stick coatings such as bovine serum albumin (BSA) or polyethylene glycol (PEG), as described herein. One method of preventing clogging is to minimize the area of contact between the sieve and the particles.

Figure 24A:
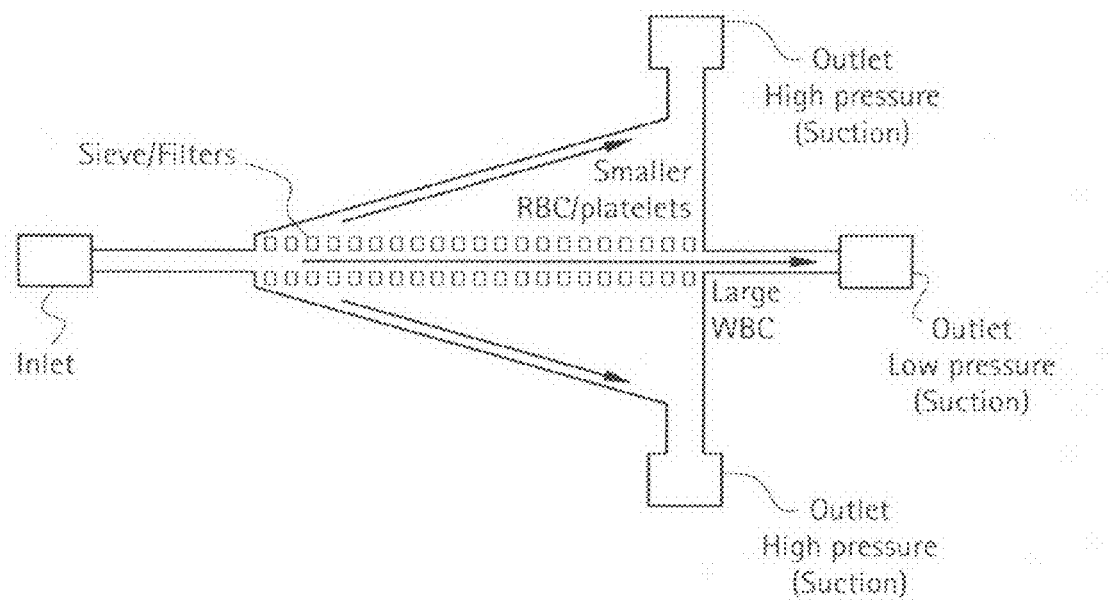
FIG. 24A is an illustration of a device for size based separation.
Figure 24B:
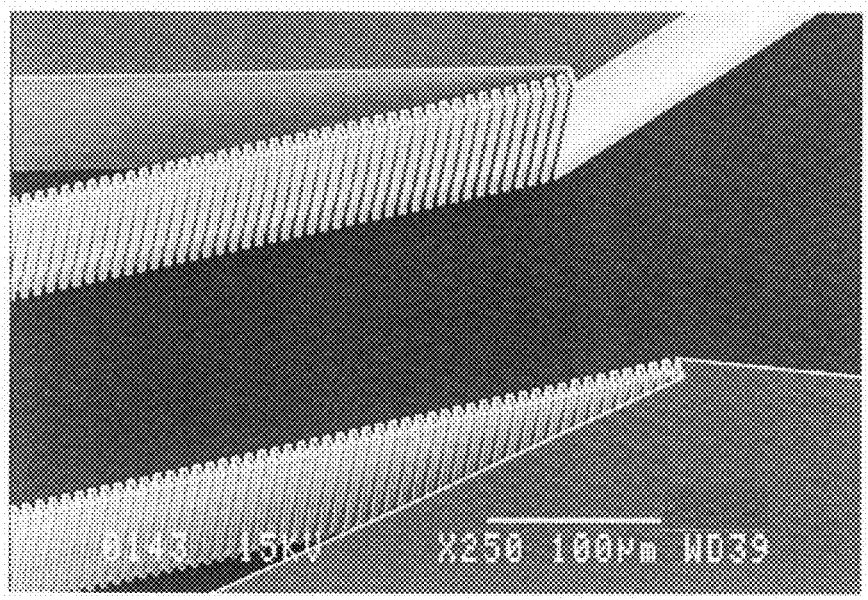
FIG. 24B is an electron micrograph of a device for size based separation.

The schematic of a low shear stress filtration device is shown in FIG. 24. The device has one inlet channel which leads into a diffuser, which is a widened portion of the channel. Typically, the channel widens in a V-shaped pattern. The diffuser contains two sieves having pores shaped to filter, for example, smaller RBCs and platelets from blood, while enriching the population of WBCs and fetal RBCs. The diffuser geometry widens the laminar flow streamlines forcing more cells to come in contact with the sieves while moving through the device. The device contains 3 outlets, two outlets collect cells that pass through the sieves, e.g., the RBCs and platelets, and one outlet collects the enriched WBCs and fetal RBCs.

The diffuser device typically does not ensure 100% depletion of RBCs and platelets. Initial RBC:WBC ratios of 600:1 can, however, be improved to ratios around 1:1. Advantages of this device are that the flow rates are low enough that shear stress on the cells does not affect the phenotype or viability of the cells and that the filters ensure that all the large cells (i.e., those unable to pass through the sieves) are retained such that the loss of large cells is minimized or eliminated. This property also ensures that the population of cells that pass through sieve do not contain large cells, even though some smaller cells may be lost. Widening the diffuser angle will result in a larger enrichment factor. Greater enrichment can also be obtained by the serial arrangement of more than one diffuser where the outlet from one diffuser feeds into the inlet of a second diffuser. Widening the gaps between the obstacles might expedite the depletion process at the risk of losing large cells through the larger pores in the sieves. For separating maternal red blood cells from fetal nucleated red blood cells, an exemplary spacing is 2-4 µm.

Method. The device of the invention is a continuous flow cell sorter, e.g., that filters larger WBCs and fetal RBCs from blood. The location of the sieves in the device is chosen to ensure that the maximum number of particles come into contact with the sieves, while at the same time avoiding clogging and allowing for retrieval of the particles after separation. In general, particles are moved across their laminar flow lines which are maintained because of extremely low Reynolds number in the channels in the device, which are typically micrometer sized.

Fabrication. Simple microfabrication techniques like poly (dimethylsiloxane) (PDMS) soft lithography, polymer casting (e.g., using epoxies, acrylics, or urethanes), injection molding, polymer hot embossing, laser micromachining, thin film surface micromachining, deep etching of both glass and silicon, electroforming, and 3-D fabrication techniques such as stereolithography can be used for the fabrication of the channels and sieves of devices of the invention. Most of the above listed processes use photomasks for replication of micro-features. For feature sizes of greater than 5 µm, transparency based emulsion masks can be used. Feature sizes between 2 and 5 µm may require glass based chrome photomasks. For smaller features, a glass based E-beam direct write mask can be used. The masks are then used to either define a pattern of photoresist for etching in the case of silicon or glass or define negative replicas, e.g., using SU-8 photoresist, which can then be used as a master for replica molding of polymeric materials like PDMS, epoxies, and acrylics. The fabricated channels and may then be bonded onto a rigid substrate like glass to complete the device. Other methods for fabrication are known in the art. A device of the invention may be fabricated from a single material or a combination of materials.

Example. In one example, a device for size based separation of smaller RBCs and platelets from the larger WBCs was fabricated using simple soft lithography techniques. A chrome photomask having the features and geometry of the device was fabricated and used to pattern a silicon wafer with a negative replica of the device in SU-8 photoresist. This master was then used to fabricate PDMS channel and sieve structures using standard replica molding techniques. The PDMS device was bonded to a glass slide after treatment with $O_2$ plasma. The diffuser geometry is used to widen the laminar flow streamlines to ensure that the majority of the particles or cells flowing through the device will interact with the sieves. The smaller RBC and platelets pass through the sieves, and the larger WBCs are confined to the central channel.

Combination of Devices

Figure 25:
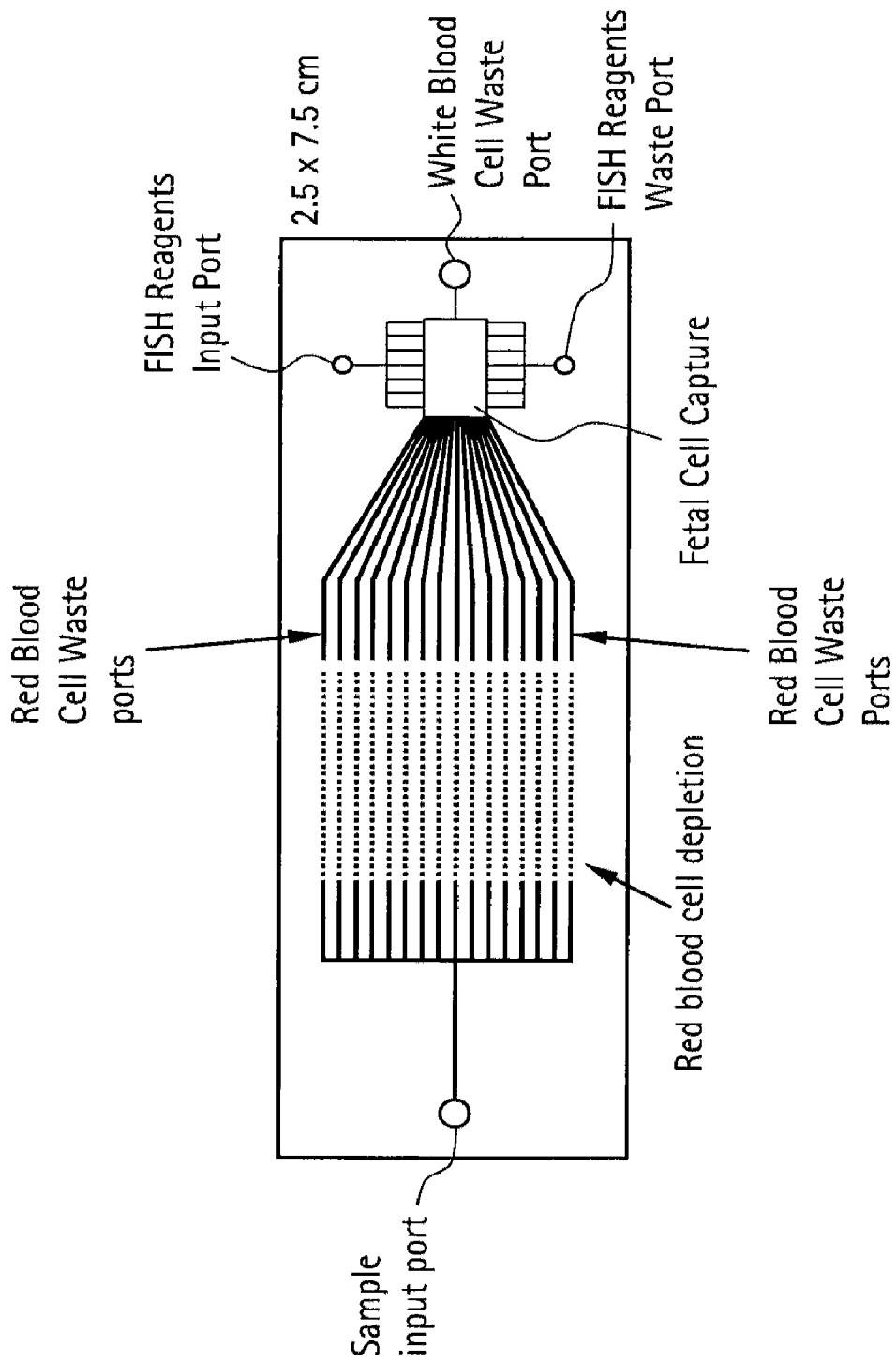
FIG. 25 is a schematic representation of a device of the invention for isolating and analyzing fetal red blood cells.

The devices of the invention may be used alone or in any combination. In addition, the steps of the methods described herein may be employed in any order. A schematic representation of a combination device for detecting and isolating fetal red blood cells is shown in FIG. 25. In one example, a sample may be processed using the cell lysis step, and then desired cells may be trapped in a cell binding device. If the cells trapped are sufficiently pure, no further processing step is needed. Alternatively, only one of the lysis or binding steps may be employed prior to arraying. In another example, a mixture of cells may be subjected to lysis, size based separation, binding, and arraying.

The methods of the invention may be carried out on one integrated device containing regions for cell lysis, cell binding, arraying, and size based separation. Alternatively, the devices may be separate, and the populations of cells obtained from each step may be collected and manually transferred to devices for subsequent processing steps.

Positive or negative pressure pumping may be used to transport cells through the microfluidic devices of the invention.

Analysis

After being enriched by one or more of the devices of the invention, cells may be collected and analyzed by various methods, e.g., nucleic acid analysis. The sample may also be further processed prior to analysis. In one example, cells may be collected on a planar substrate for fluorescence in situ hybridization (FISH), followed by fixing of the cells and imaging. Such analysis may be used to detect fetal abnormalities such as Down syndrome, Edwards' syndrome, Patau's syndrome, Klinefelter syndrome, Turner syndrome, sickle cell anemia, Duchenne muscular dystrophy, and cystic fibrosis. The analysis may also be performed to determine a particular trait of a fetus, e.g., sex.

OTHER EMBODIMENTS

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A flow-through device for enriching tumor cells or epithelial cells, or both, in a blood sample, the device comprising
a flow chamber through which the blood sample flows along a flow path;
an array of obstacles distributed in the flow chamber, wherein the obstacles in the array are arranged in at least two rows aligned normal to the flow path, wherein the obstacles are equally spaced within each row in the array, and each successive row of obstacles is shifted in a direction normal to the flow path relative to the obstacles in the preceding row;
wherein (i) a distance between the obstacles varies in the flow direction and (ii) the obstacles have the same shape; and
wherein the array of obstacles forms a network of microfluidic channels disposed to selectively enrich tumor cells or epithelial cells, or both in a blood sample flowed through the device by a factor of at least 1000.

2. The device of claim 1, wherein the device selectively enriches tumor cells.

3. The device of claim 1, wherein the device retains at least 60% of the tumor cells or epithelial cells present in the blood sample.

4. The device of claim 1, wherein a row of obstacles in the array is shifted by a distance equal to a radius of capture of the tumor cells or epithelial cells.

5. The device of claim 1, wherein said device enriches tumor cells or epithelial cells, or both, from said blood sample from said patient by a factor of at least 100,000.

6. The device of claim 1, wherein the array is configured to enable flow of cells without mechanically damaging them.

7. The device of claim 1, wherein the obstacles in each of the rows in the array are spaced apart by at most 100 µm, and wherein the obstacles in a given row of obstacles in the array are shifted in a direction normal to the flow path by a distance of at most 50 µm-with respect to obstacles in an adjacent row.

8. The device of claim 1, wherein the array of obstacles is coated with a binding moiety that selectively binds to epithelial cells.

9. The device of claim 1, wherein the array of obstacles is coated with a binding moiety that selectively binds to tumor cells.

10. The device of claim 1, wherein a distance between edges of two adjacent obstacles in the array of obstacles is larger than a size of a largest cell in the blood sample.

11. The device of claim 1, wherein the obstacles are circular in cross-section.

12. The device of claim 1, wherein a diameter of an obstacle is 5 µm, 10 µm, 25 µm, 50 µm, 75 µm, 100 µm, or 250 µm.

13. The device of claim 1, wherein each obstacle is 5 µm, 10 µm, 25 µm, 50 µm, 75 µm, or 250 µm at a widest point of the obstacle.

14. The device of claim 1, wherein a spacing between the obstacles is 10 µm, 25 µm, 50 µm, 75 µm, 100 µm, 250 µm, 500 µm, or 750 µm.

15. The device of claim 8, wherein the binding moiety is an antibody.

16. The device of claim 15, wherein the binding moiety is an antibody to a cell surface receptor.

17. The device of claim 1, wherein the obstacles in the array are spaced at most 100 µm center to center.

18. The device of claim 1, wherein the obstacles in the array are spaced at least 10 µm apart.

19. The device of claim 1, wherein the obstacles in the array are spaced at most 500 µm apart.

20. The device of claim 1, wherein said device is composed of plastic.

21. The device of claim 1, wherein the array of obstacles is an ordered array of obstacles.

22. The device of claim 1, wherein the obstacles contact both the top and bottom of the chamber.

23. The device of claim 1, wherein there is a gap between the obstacles and one surface of the flow chamber.

24. The device of claim 1, coupled to a positive pressure pump.

25. The device of claim 1, coupled to a negative pressure pump.

26. The device of claim 1, coupled to an imaging system.

27. The device of claim 1, wherein a spacing between obstacles is at least 10 µm.

28. The device of claim 1, wherein a spacing between obstacles is at most 100 µm.

29. A device comprising
a flow chamber comprising an inlet and an outlet and a flow path from the inlet to the outlet in which a fluid sample may flow;
a substrate that forms a bottom of the flow chamber;
a plurality of obstacles arranged in a first array and a second array on the substrate,
wherein the first array comprises a plurality of obstacles arranged in two or more rows aligned normal to the flow path and forming a plurality of equilateral triangular arrays of obstacles, wherein each obstacle has an equal center-to-center distance to any adjacent obstacle,
wherein the second array comprises a plurality of obstacles arranged in two or more rows aligned normal to the flow path and forming a plurality of triangular arrays of obstacles, wherein one or more of the obstacles in the second array are shifted to have a first center-to-center distance to a first adjacent obstacle that is different than a second center-to-center distance to a second adjacent obstacle
and further wherein at least the first or second array of obstacles, or both, is coated with a binding moiety that selectively binds to a first type of cell in the sample, wherein the first type of cell is a tumor cell or epithelial cell.

30. The device of claim 29, wherein the obstacles shifted in the second array are shifted by a distance equal to a radius of capture of the first type of cell.

31. The device of claim 29, wherein the binding moiety is an antibody.

32. The device of claim 31, wherein the binding moiety is an antibody to a cell surface receptor.

* * * * *